US010675009B2

(12) United States Patent
Hess et al.

(10) Patent No.: US 10,675,009 B2
(45) Date of Patent: Jun. 9, 2020

(54) MULTI-HEAD REPOSITORY FOR USE WITH A SURGICAL DEVICE

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Ryan A. Bledsoe, Cincinnati, OH (US); Jeffrey L. Savage, West Chester, OH (US); Craig T. Gates, West Chester, OH (US); Douglas E. Withers, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 419 days.

(21) Appl. No.: 14/930,952

(22) Filed: Nov. 3, 2015

(65) Prior Publication Data

US 2017/0119360 A1    May 4, 2017

(51) Int. Cl.
  *A61B 17/00* (2006.01)
  *A61B 17/34* (2006.01)
  *A61B 90/00* (2016.01)

(52) U.S. Cl.
  CPC .............. *A61B 17/00* (2013.01); *A61B 17/34* (2013.01); *A61B 17/3423* (2013.01);
  (Continued)

(58) Field of Classification Search
  CPC ........ A61B 17/3421; A61B 2017/3445; A61B 2017/3449; A61B 1/00087; A61B 1/00101; A61B 2017/00362; A61B 2017/2931
  See application file for complete search history.

(56) References Cited

U.S. PATENT DOCUMENTS 3,043,309 A    7/1962   McCarthy
3,358,676 A   12/1967   Frei et al.
(Continued)

FOREIGN PATENT DOCUMENTS

DE    101 49 421 A1    4/2003
EP    1 709 900 A1    10/2006
(Continued)

OTHER PUBLICATIONS

International Search Report dated Mar. 21, 2011; International Application No. PCT/US2010/051812 (7 pages).
(Continued)

*Primary Examiner* — Katherine M Shi
*Assistant Examiner* — Lindsey Bachman
(74) *Attorney, Agent, or Firm* — Mintz Levin Cohn Ferris Glovsky and Popeo, P.C.

(57) ABSTRACT

Devices and methods for organizing a plurality of end effectors and selectively delivering them through surgical trocars are described herein. In one embodiment, a surgical end effector loading device is provided that includes at least one mating element to interface with a surgical trocar, a deployment lumen positioned to align with a working channel of a surgical trocar, an end effector repository having a plurality of end effector lumens formed therein to receive end effectors, the repository being configured to selectively align any of the plurality of end effector lumens with the deployment lumen, and an advancer coupled to the repository and configured to advance an end effector from the repository through the deployment lumen.

18 Claims, 43 Drawing Sheets

(52) U.S. Cl.
CPC .... *A61B 90/08* (2016.02); *A61B 2017/00362* (2013.01); *A61B 2017/00486* (2013.01)

(56) References Cited

U.S. PATENT DOCUMENTS

| | | | |
|---|---|---|---|
| 3,710,399 A | 1/1973 | Hurst | |
| 3,893,448 A | 7/1975 | Brantigan | |
| 3,906,217 A | 9/1975 | Lackore | |
| 3,988,535 A | 10/1976 | Hickman et al. | |
| 4,047,136 A | 9/1977 | Satto | |
| 4,063,561 A | 12/1977 | McKenna | |
| 4,099,192 A | 7/1978 | Aizawa et al. | |
| 4,278,077 A | 7/1981 | Mizumoto | |
| 4,384,584 A | 5/1983 | Chen | |
| 4,585,282 A | 4/1986 | Bosley | |
| 4,597,390 A | 7/1986 | Mulhollan et al. | |
| 4,655,746 A | 4/1987 | Daniels et al. | |
| 5,052,402 A | 10/1991 | Bencini et al. | |
| 5,201,743 A | 4/1993 | Haber et al. | |
| 5,282,806 A | 2/1994 | Haber et al. | |
| 5,286,255 A | 2/1994 | Weber | |
| 5,308,357 A | 5/1994 | Lichtman | |
| 5,314,424 A | 5/1994 | Nicholas | |
| 5,330,502 A | 7/1994 | Hassler et al. | |
| 5,352,219 A | 10/1994 | Reddy | |
| 5,392,917 A | 2/1995 | Alpern et al. | |
| 5,417,203 A | 5/1995 | Tovey et al. | |
| 5,441,059 A | 8/1995 | Dannan | |
| 5,468,250 A | 11/1995 | Paraschac et al. | |
| 5,502,698 A | 3/1996 | Mochizuki | |
| 5,507,297 A | 4/1996 | Slater et al. | |
| 5,540,648 A | 7/1996 | Yoon | |
| 5,562,655 A | 10/1996 | Mittelstadt et al. | |
| 5,578,052 A | 11/1996 | Koros et al. | |
| 5,593,402 A | 1/1997 | Patrick | |
| 5,613,937 A | 3/1997 | Garrison et al. | |
| 5,618,303 A | 4/1997 | Marlow et al. | |
| 5,716,326 A | 2/1998 | Dannan | |
| 5,762,255 A | 6/1998 | Chrisman et al. | |
| 5,792,165 A | 8/1998 | Klieman et al. | |
| 5,810,877 A | 9/1998 | Roth et al. | |
| 5,881,615 A | 3/1999 | Dahl et al. | |
| 5,928,263 A | 7/1999 | Hoogeboom | |
| 5,980,455 A | 11/1999 | Daniel et al. | |
| 6,024,748 A | 2/2000 | Manzo et al. | |
| 6,059,719 A | 5/2000 | Yamamoto et al. | |
| 6,099,537 A | 8/2000 | Sugai et al. | |
| 6,159,200 A | 12/2000 | Verdura et al. | |
| 6,309,397 B1 | 10/2001 | Julian et al. | |
| 6,315,789 B1 | 11/2001 | Cragg | |
| 6,332,384 B1 * | 12/2001 | Cluthe | B25G 1/085 81/439 |
| 6,419,688 B1 | 7/2002 | Bacher et al. | |
| 6,471,172 B1 | 10/2002 | Lemke et al. | |
| 6,589,211 B1 | 7/2003 | MacLeod | |
| 6,595,984 B1 | 7/2003 | DeGuillebon | |
| 6,626,824 B2 | 9/2003 | Ruegg et al. | |
| 6,635,071 B2 | 10/2003 | Boche et al. | |
| 6,656,198 B2 | 12/2003 | Tsonton et al. | |
| 6,723,043 B2 | 4/2004 | Kleeman et al. | |
| 6,770,081 B1 | 8/2004 | Cooper et al. | |
| 6,776,165 B2 | 8/2004 | Jin | |
| 6,827,712 B2 | 12/2004 | Tovey et al. | |
| 6,860,878 B2 | 3/2005 | Brock | |
| 6,869,395 B2 | 3/2005 | Page et al. | |
| 6,884,213 B2 | 4/2005 | Raz et al. | |
| 6,936,003 B2 | 8/2005 | Iddan | |
| 6,942,674 B2 | 9/2005 | Belef et al. | |
| 6,986,738 B2 | 1/2006 | Glukhovsky et al. | |
| 6,994,708 B2 | 2/2006 | Manzo | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,083,579 B2 | 8/2006 | Yokoi et al. | |
| 7,122,028 B2 | 10/2006 | Looper et al. | |
| 7,125,403 B2 | 10/2006 | Julian et al. | |
| 7,169,104 B2 | 1/2007 | Ueda et al. | |
| 7,199,545 B2 | 4/2007 | Oleynikov et al. | |
| 7,211,094 B2 | 5/2007 | Gannoe et al. | |
| 7,241,290 B2 | 7/2007 | Doyle et al. | |
| 7,297,142 B2 * | 11/2007 | Brock | A61B 5/0086 348/65 |
| 7,331,967 B2 | 2/2008 | Lee et al. | |
| 7,429,259 B2 | 9/2008 | Cadeddu et al. | |
| 7,448,993 B2 | 11/2008 | Yokoi et al. | |
| 7,559,887 B2 | 7/2009 | Dannan | |
| 7,566,331 B2 | 7/2009 | Looper et al. | |
| 7,604,642 B2 | 10/2009 | Brock | |
| 7,651,471 B2 | 1/2010 | Yokoi et al. | |
| 7,665,391 B2 * | 2/2010 | Beauchamp | B25G 1/085 81/177.1 |
| 7,666,181 B2 | 2/2010 | Abou El Kheir | |
| 7,678,043 B2 | 3/2010 | Gilad | |
| 7,691,103 B2 | 4/2010 | Fernandez et al. | |
| 7,691,126 B2 | 4/2010 | Bacher | |
| 7,699,835 B2 | 4/2010 | Lee et al. | |
| 7,722,599 B2 | 5/2010 | Julian et al. | |
| 7,862,553 B2 | 1/2011 | Ewaschuk | |
| 7,894,882 B2 | 2/2011 | Mullick et al. | |
| 7,901,398 B2 | 3/2011 | Stanczak et al. | |
| 8,021,358 B2 | 9/2011 | Doyle et al. | |
| 8,034,032 B2 | 10/2011 | Voegele et al. | |
| 8,038,612 B2 | 10/2011 | Paz | |
| 8,052,636 B2 | 11/2011 | Moll et al. | |
| 8,057,502 B2 | 11/2011 | Maliglowka et al. | |
| 8,088,062 B2 | 1/2012 | Zwolinski | |
| 8,128,643 B2 | 3/2012 | Aranyi et al. | |
| 8,182,414 B2 | 5/2012 | Handa et al. | |
| 8,187,166 B2 | 5/2012 | Kuth et al. | |
| 8,377,044 B2 | 2/2013 | Coe et al. | |
| 8,397,335 B2 | 3/2013 | Gordin et al. | |
| 8,398,544 B2 | 3/2013 | Altamirano | |
| 8,409,076 B2 | 4/2013 | Pang et al. | |
| 8,475,361 B2 | 7/2013 | Barlow et al. | |
| 8,518,024 B2 | 8/2013 | Williams et al. | |
| 8,623,011 B2 | 1/2014 | Spivey | |
| 8,636,648 B2 | 1/2014 | Gazdzinski | |
| 8,721,539 B2 | 5/2014 | Shohat et al. | |
| 8,764,735 B2 | 7/2014 | Coe et al. | |
| 8,845,661 B2 | 9/2014 | D'Arcangelo et al. | |
| 9,142,527 B2 | 9/2015 | Lee et al. | |
| 9,282,879 B2 | 3/2016 | Farin et al. | |
| 9,308,011 B2 | 4/2016 | Chao et al. | |
| 9,408,628 B2 | 8/2016 | Altamirano | |
| 9,451,937 B2 | 9/2016 | Parihar | |
| 2001/0051766 A1 | 12/2001 | Gazdzinski | |
| 2003/0060702 A1 | 3/2003 | Kuth et al. | |
| 2003/0114731 A1 | 6/2003 | Cadeddu et al. | |
| 2004/0093039 A1 | 5/2004 | Schumert | |
| 2004/0133235 A1 | 7/2004 | Bacher | |
| 2004/0152941 A1 | 8/2004 | Asmus et al. | |
| 2005/0033354 A1 | 2/2005 | Montalvo et al. | |
| 2005/0070943 A1 * | 3/2005 | Hueil | A61B 17/34 606/167 |
| 2005/0085697 A1 | 4/2005 | Yokoi et al. | |
| 2005/0119640 A1 | 6/2005 | Sverduk et al. | |
| 2005/0131396 A1 | 6/2005 | Stanczak et al. | |
| 2005/0165449 A1 | 7/2005 | Cadeddu et al. | |
| 2005/0215983 A1 | 9/2005 | Brock | |
| 2005/0250984 A1 | 11/2005 | Lam et al. | |
| 2005/0272972 A1 | 12/2005 | Iddan | |
| 2005/0272974 A1 | 12/2005 | Iddan | |
| 2005/0273139 A1 | 12/2005 | Krauss et al. | |
| 2005/0288555 A1 | 12/2005 | Binmoeller | |
| 2006/0079933 A1 | 4/2006 | Hushka et al. | |
| 2006/0149135 A1 | 7/2006 | Paz | |
| 2006/0184161 A1 | 8/2006 | Maahs et al. | |
| 2006/0190035 A1 | 8/2006 | Hushka et al. | |
| 2006/0195015 A1 | 8/2006 | Mullick et al. | |
| 2006/0229592 A1 | 10/2006 | Yokoi et al. | |
| 2006/0258905 A1 | 11/2006 | Kaji et al. | |
| 2007/0010709 A1 | 1/2007 | Reinschke | |
| 2007/0049966 A1 | 3/2007 | Bonadio et al. | |
| 2007/0073247 A1 | 3/2007 | Ewaschuk | |

(56) References Cited

U.S. PATENT DOCUMENTS

| | | |
|---|---|---|
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0093833 A1 | 4/2009 | Smith |
| 2009/0209947 A1 | 8/2009 | Gordin et al. |
| 2010/0147921 A1* | 6/2010 | Olson .................. A61B 17/072 227/175.1 |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0118756 A1 | 5/2011 | Brock |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0089176 A1 | 4/2012 | Sigmon, Jr. et al. |
| 2012/0095298 A1 | 4/2012 | Stefanchik et al. |
| 2012/0259325 A1 | 10/2012 | Houser et al. |
| 2012/0316575 A1 | 12/2012 | Farin et al. |
| 2013/0138091 A1 | 5/2013 | Coe et al. |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0194685 A1* | 7/2014 | Riek .................. A61B 17/3421 600/109 |
| 2014/0243799 A1 | 8/2014 | Parihar |
| 2014/0243800 A1 | 8/2014 | Parihar |
| 2014/0275791 A1 | 9/2014 | Lambrecht et al. |
| 2014/0277018 A1 | 9/2014 | Parihar |
| 2014/0378953 A1 | 12/2014 | Coe et al. |
| 2015/0088191 A1 | 3/2015 | Coe et al. |
| 2017/0119361 A1 | 5/2017 | Hess et al. |

FOREIGN PATENT DOCUMENTS

| | | |
|---|---|---|
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/081702 A1 | 7/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |
| WO | WO-2015025178 A1 | 2/2015 |

OTHER PUBLICATIONS

International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed Oct. 9, 2009 for U.S. Appl. No. 12/576,529 (18 pages).
European Search Report for European Application No. 16196867.2, dated Apr. 3, 2017.

* cited by examiner

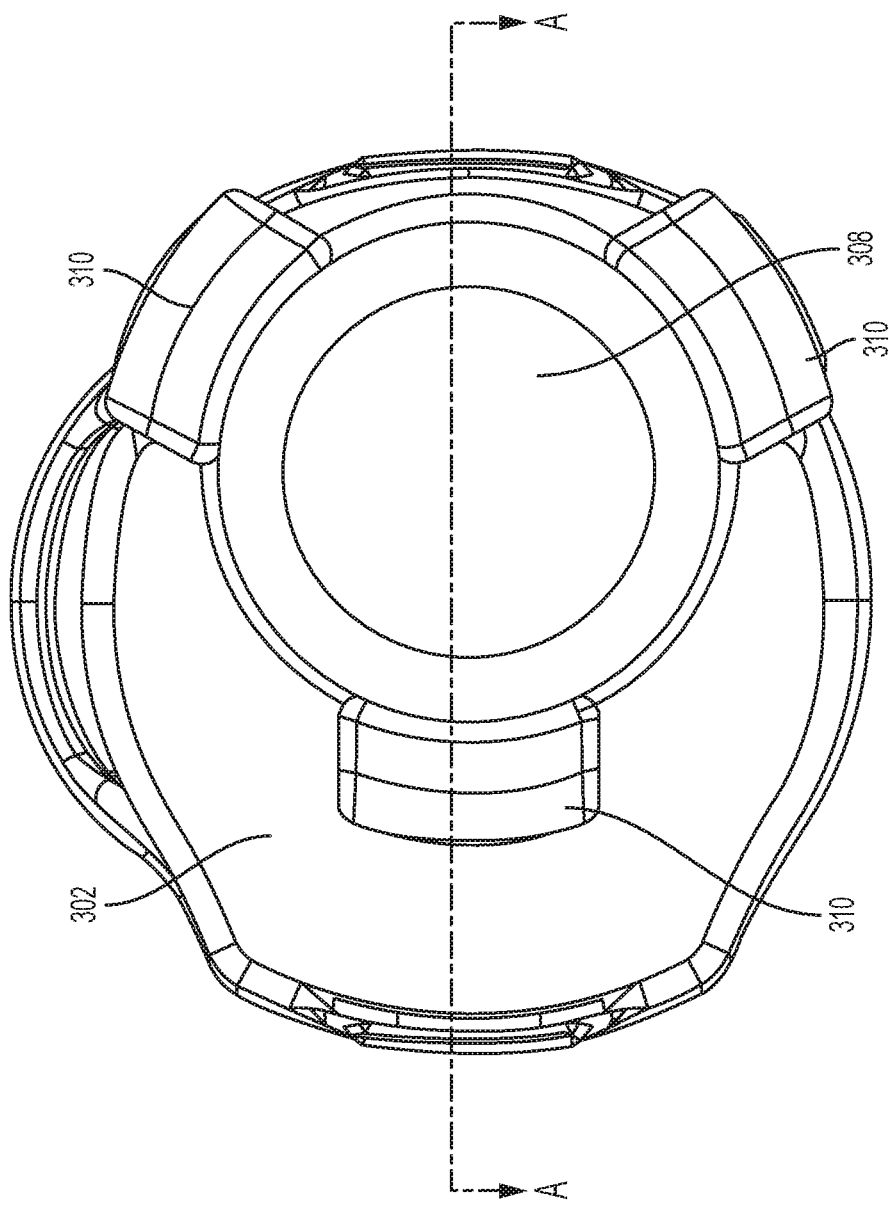

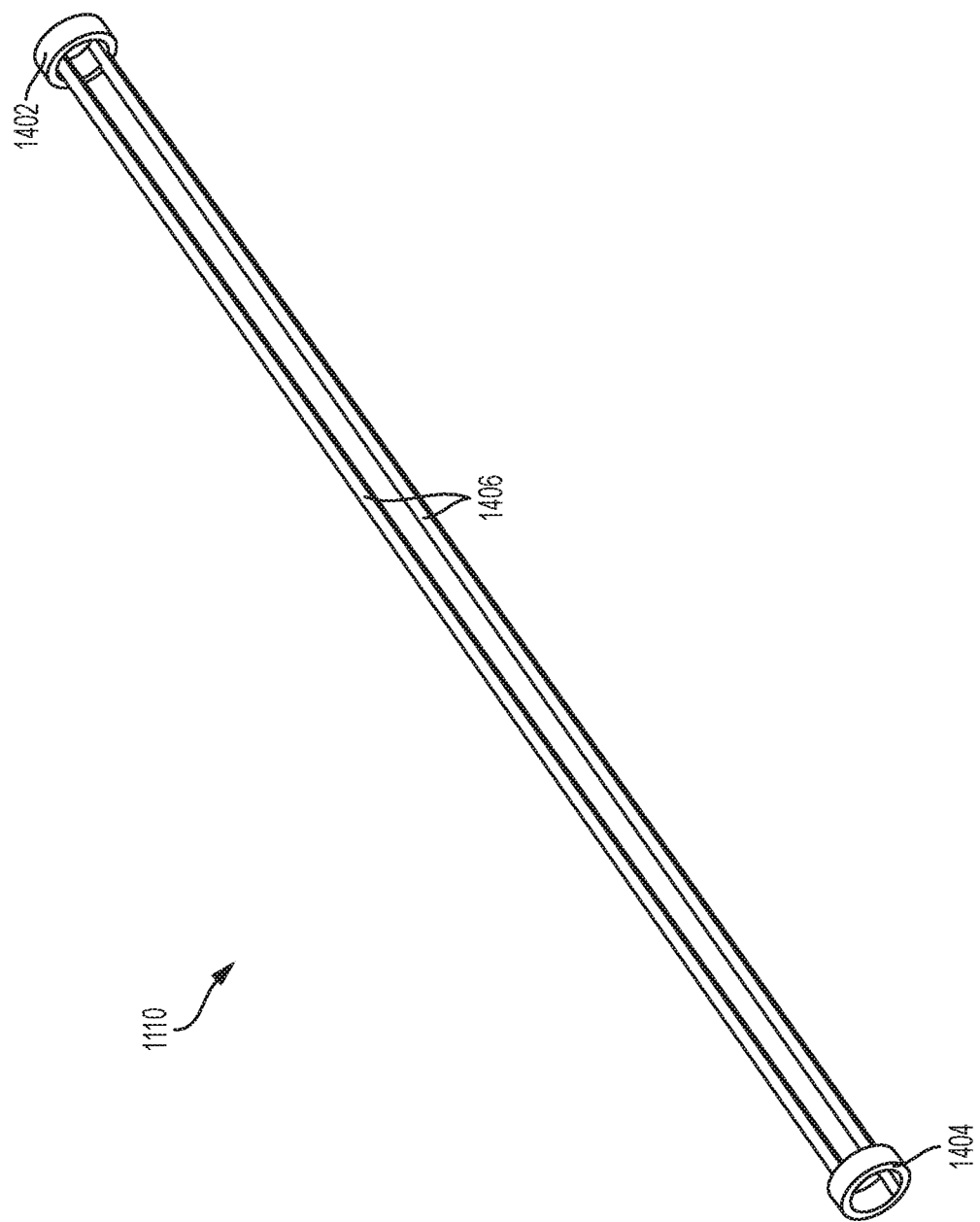

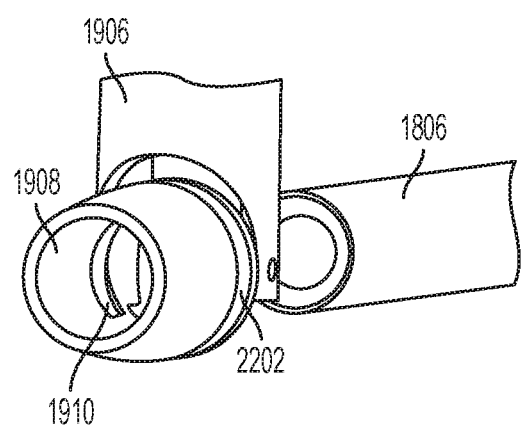 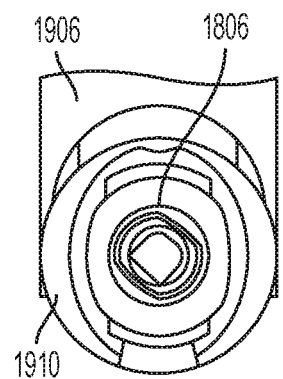
FIG. 23A      FIG. 23B
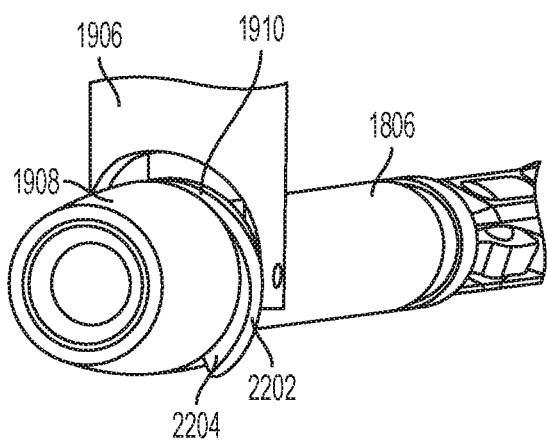 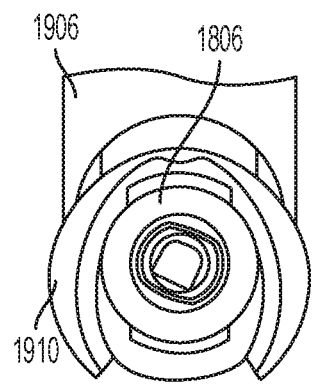
FIG. 24A      FIG. 24B

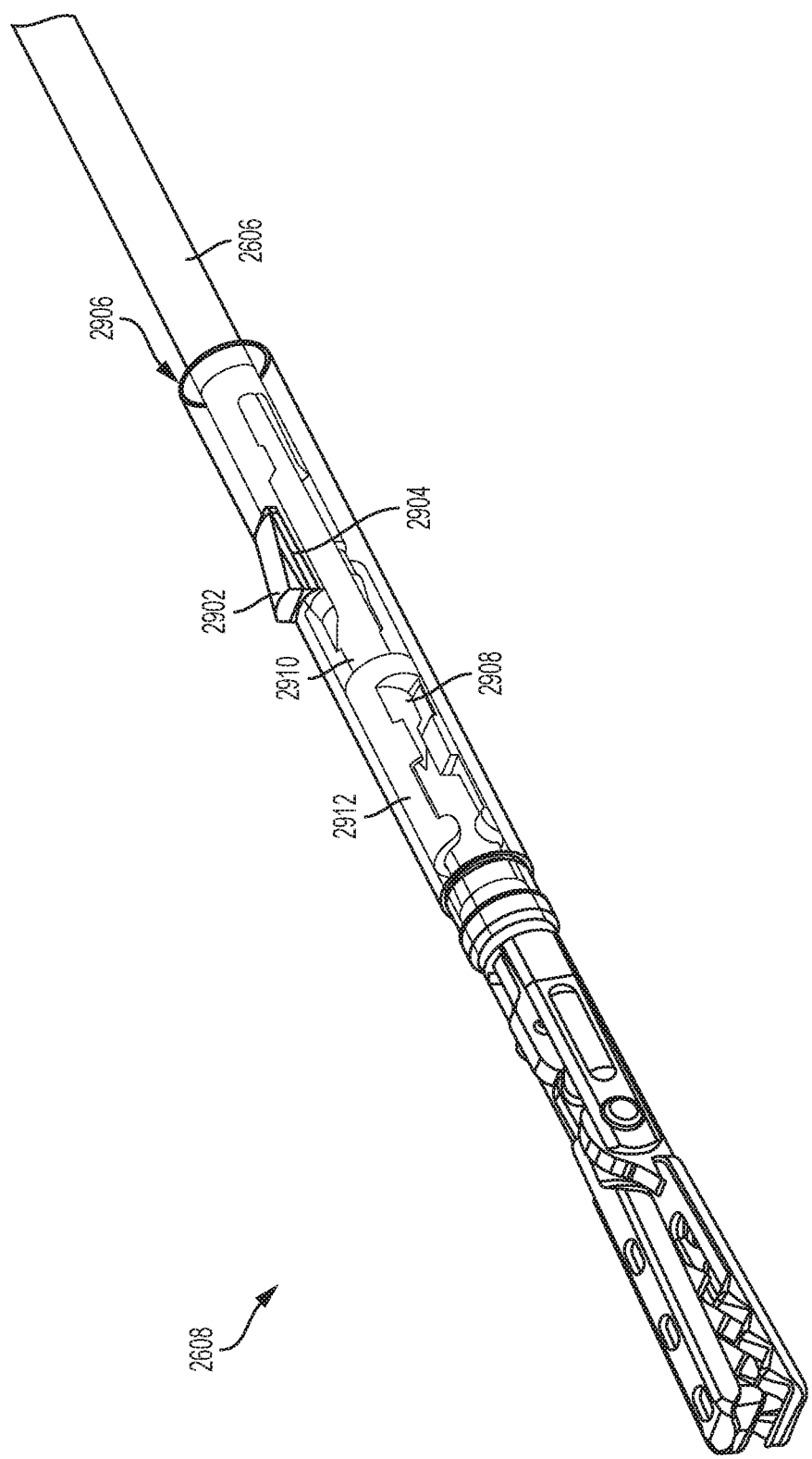

MULTI-HEAD REPOSITORY FOR USE WITH A SURGICAL DEVICE

FIELD OF INVENTION

This disclosure relates generally to surgical instruments and, more particularly, to devices that deliver end effectors to a surgical site.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

In many minimally invasive procedures, the abdominal cavity is insufflated with carbon dioxide gas to provide adequate space to perform a procedure. The insufflated cavity is generally under pressure and is sometimes referred to as being in a state of pneumoperitoneum. Surgical access devices are often used to facilitate surgical manipulation of internal tissue while maintaining pneumoperitoneum. For example, during a surgical procedure the abdominal wall can be pierced and a cannula or trocar (such as the trocar shown in FIGS. 1A-2) can be inserted into the abdominal cavity. The trocar can provide a port through which other surgical instruments can be passed into a patient's body to perform a variety of procedures.

Development in minimally invasive surgery has resulted in increasingly complex procedures that require multiple instruments and precise manipulations within the body. Because of the limited access space afforded by a trocar and the relatively larger wound size associated therewith, one solution has been the use of percutaneous surgical instruments inserted directly into a body cavity and used to supplement instruments introduced through one or more trocars. For example, procedures have been developed that involve additional percutaneous instruments to aid in retracting organs and structures. In some procedures, one or more percutaneous instruments having removable end effectors are utilized in combination with a trocar that can accommodate the passage of various end effectors for connection with the instrument in vivo. Inserting surgical instruments percutaneously, i.e., passing directly through tissue without an access device, can further reduce trauma and scarring to the patient by reducing the size of the wound created. Additional details on such instruments can be found, for example, in U.S. Patent Application Publication No. 2011/0087267 to Spivey et al., entitled "Method For Exchanging End Effectors In Vivo," which is hereby incorporated by reference.

The increasing use of percutaneously-inserted surgical instruments is not without challenges, however. For example, the use of percutaneously-inserted surgical instruments can require a large operating staff to simultaneously manipulate the percutaneously-inserted instrument, the trocar providing access to pass an end effector, and a loading device used to deliver the end effector through the trocar and attach it to the distal end of the instrument. The complexity of this operation is compounded when several end effectors are used in sequence to accomplish different tasks (e.g., grasping, cutting, etc.). In such a case, a surgeon or other user is forced to juggle the plurality of end effectors along with at least one loading device, trocar, and percutaneous instrument.

In addition, it can be difficult to successfully attach or remove an end effector from a percutaneously-inserted instrument inside a patient's body. There are a number of reasons for this, not the least of which is the confined and remote environment in which the instrument shaft and end effector are being manipulated. Surgeons can struggle to ensure that the straight shaft of the surgical trocar and the straight shaft of the percutaneous instrument are in alignment when coupling or decoupling an end effector. Moreover, it can be difficult in this confined environment to determine when an end effector is completely and successfully coupled to a percutaneous instrument and/or a loading device. Making this determination can be important, however, because prematurely releasing an end effector from one instrument before coupling it to another can drop the end effector within the body cavity, necessitating further time and action to retrieve it.

One attempted solution to these challenges has been to utilize the trocar as a means for passing the distal end of a percutaneously-inserted instrument back out of a patient's body in order to exchange end effectors. Passing the instrument (either with or without an end effector attached) through the trocar in the "wrong" direction (i.e., from its distal end toward its proximal end) can damage the one or more seals present in the trocar that help maintain pneumoperitoneum. This is because trocar seals are often designed with a "duckbill" or other shape that is oriented for proximal-to-distal instrument passage.

Accordingly, there is a need for improved devices and methods that assist users in managing a number of modular surgical end effectors and passing them into a patient's body for attachment to a surgical instrument positioned inside the body. There is also a need for improved devices and methods that provide better feedback to a user regarding the coupling (or lack thereof) between an end effector and another instrument.

SUMMARY OF THE INVENTION

The present invention generally provides devices and methods for managing and delivering surgical end effectors into a patient's body for attachment to another surgical instrument in vivo. The devices and methods described herein can reduce the complexity of this type of operation by providing a loading device having an end effector repository capable of housing a plurality of end effectors and selectively deploying any such end effector into a patient's body. Further, the devices and methods described herein can couple to a surgical trocar in the same manner that an obturator is typically coupled to a trocar. This coupling can effectively combine the loading device and trocar into a single component that can be more easily manipulated by a user. This single component provides for organizing and deploying a plurality of surgical end effectors. The devices and methods described herein can also include features designed to ease the process of aligning and coupling an end effector to a percutaneous instrument, such as the ability to pivot an end effector within the patient's body for easier alignment, or the inclusion of one or more features that provide feedback when an end effector is securely coupled or not.

In one aspect, a surgical end effector loading device is provided that includes at least one mating element configured to interface with at least one complementary mating element of a surgical trocar to restrict movement of the loading device relative to the trocar, as well as a deployment lumen formed in a distal end of the loading device and positioned to align with a working channel of the surgical trocar when the at least one mating element is interfaced with the at least one complementary mating element of the trocar. The device further includes an end effector repository having a plurality of end effector lumens formed therein that are each configured to receive a surgical end effector, the end effector repository being further configured to selectively align any of the plurality of end effector lumens with the deployment lumen. The device also includes at least one advancer coupled to the end effector repository and configured to advance a surgical end effector from an end effector lumen of the end effector repository through the deployment lumen.

The devices and methods described herein can have a number of additional features and/or variations, all of which are within the scope of the present disclosure. In some embodiments, for example, the end effector repository can be a rotatable carousel. In such an embodiment, the carousel can rotate to align any of a plurality of end effector lumens formed therein with a deployment lumen of the loading device and/or a working channel of a surgical trocar. In other embodiments, however, the end effector repository can have alternative shapes, such as a rectangular cartridge that translates to align various end effector lumens with a deployment lumen and/or trocar working channel. Regardless of its shape, the end effector repository can have any number of end effector lumens formed therein and, in certain embodiments, can have three or more end effector lumens.

In some embodiments, the end effector repository can include a plurality of viewing ports positioned to permit visualization of the contents of each end effector lumen. Such ports can permit a user to quickly determine which end effector lumens have end effectors loaded therein and what type of end effector is in each lumen.

In certain embodiments, the at least one advancer can be slidably disposed within an end effector lumen of the end effector repository and configured to translate the surgical end effector along a longitudinal axis of the end effector lumen. In addition, the at least one advancer can be coupled to an actuator that extends beyond an outer diameter of the end effector lumen. In such an embodiment, a user can advance an end effector by translating the actuator distally along a length of the loading device.

Other configurations of the at least one advancer are possible as well. For example, in some embodiments the at least one advancer can include a worm drive mechanism to effect movement of an end effector along a longitudinal axis of the device. The worm drive mechanism can include, for example, an end effector retainer that couples to an end effector and translates along a length of the loading device as the worm drive mechanism is rotated. Note that in some embodiments a combination of a translating advancer and a worm drive mechanism or other configuration can be employed together, e.g., with one advancer carrying the end effector over a first distance and another advancer carrying the end effector over a second distance.

As noted above, in certain embodiments the loading device can include an end effector retainer disposed within the deployment lumen and configured to couple to a surgical end effector. The end effector retainer can, in some embodiments, pivot relative to the loading device in order to pivot the end effector relative to the loading device after the end effector is advanced through the deployment lumen. Pivoting the end effector in this manner can aid in aligning the end effector with a percutaneously-inserted surgical instrument to ease the coupling process.

In still other embodiments, the end effector retainer or other portion of the loading device can include one or more features to indicate when an end effector is coupled thereto. These can include, for example, pivoting or pop-up/out indicators that are actuated by an end effector mating completely with the end effector retainer. These indicators can provide helpful feedback to a user.

In another aspect, a surgical instrument kit is provided that includes a loading device having at least one mating element, a deployment lumen formed in a distal end thereof, an end effector repository having a plurality of end effector lumens formed therein, the end effector repository being configured to selectively align any of the plurality of end effector lumens with the deployment lumen, and at least one advancer coupled to the end effector repository. The kit further includes a trocar having a proximal end, a distal end, at least one mating element, and a working channel extending therethrough from the proximal end to the distal end, as well as a plurality of surgical end effectors. Further, the plurality of surgical end effectors are received within the plurality of end effector lumens of the end effector repository, the at least one mating element of the loading device interfaces with the at least one mating element of the trocar, and the deployment lumen of the loading device aligns with the working channel of the trocar.

As with the device described above, a number of variations and additional features are possible. For example, in some embodiments the end effector repository can be a rotatable carousel. Moreover, in certain embodiments the end effector repository can include a plurality of viewing ports positioned to permit visualization of the contents of each end effector lumen.

Also similar to the device described above, in some embodiments the at least one advancer can be slidably disposed within an end effector lumen of the end effector repository and configured to translate the surgical end effector along a longitudinal axis of the end effector lumen. Further, the at least one advancer can be coupled to an actuator that extends beyond an outer diameter of the end effector lumen.

In certain embodiments, the loading device of the kit can further include an end effector retainer positioned within the deployment lumen and configured to selectively couple to one of the plurality of surgical end effectors. Moreover, in some embodiments the end effector retainer can pivot relative to the loading device in order to pivot a surgical end effector coupled thereto relative to the loading device after the surgical end effector is advanced through the deployment lumen.

In another aspect, a surgical method is provided that includes coupling a loading device with a surgical trocar such that a deployment lumen formed in the loading device coaxially aligns with a working channel of the surgical trocar and complementary mating features on the loading device and the surgical trocar restrict relative motion therebetween. The method further includes actuating an end effector repository of the loading device to align one of a plurality of end effector lumens formed therein with the deployment lumen of the loading device, and advancing a surgical end effector housed within the end effector lumen through the deployment lumen of the loading device and the working channel of the surgical trocar.

In some embodiments, advancing the surgical end effector can include rotating a worm drive mechanism to effect distal advancement of the surgical end effector. In other embodiments, however, advancing the surgical end effector can include translating an advancer distally within the end effector lumen. In still other embodiments, advancing the surgical end effector can include a combination of translating and rotating various components of the loading device.

In certain embodiments, the method can further include pivoting the surgical end effector relative to the loading device after the end effector has been advanced through the working channel of the surgical trocar. This can, for example, ease the process of aligning the end effector with a surgical instrument for coupling thereto.

Any of the features or variations described above can be applied to any particular aspect or embodiment of the invention in a number of different combinations. The absence of explicit recitation of any particular combination is due solely to the avoidance of repetition in this summary.

BRIEF DESCRIPTION OF THE DRAWINGS

FIG. 3C is a top view of the device of FIG. 3A;

FIG. 14 is a perspective view of an end effector retainer guide of the device of FIG. 9A;

FIG. 23A is a perspective view of the end effector retainer and the end effector of FIG. 18A in an uncoupled configuration;

FIG. 23B is a side view of the end effector retainer and the end effector of FIG. 23A;

FIG. 24A is a perspective view of the end effector retainer and the end effector of FIG. 18A in a coupled configuration;

FIG. 24B is a side view of the end effector retainer and end effector of FIG. 24A;

FIG. 29B is a partially-transparent view of the portion of the device of FIG. 29A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, sizes and shapes of the devices, and the components thereof, can depend at least on the anatomy of the subject in which the devices will be used, the size and shape of components with which the devices will be used, and the methods and procedures in which the devices will be used.

Surgical devices and methods are described herein that provide for improved organization and delivery of surgical instrument end effectors into a patient's body through a surgical trocar. The devices and methods provided for include an end effector repository capable of housing a plurality of modular end effectors and selectively delivering any of the end effectors through a deployment lumen. Furthermore, features are included for mating an end effector loading device to a surgical trocar such that a surgeon or other user no longer needs to manipulate two devices separately. By combining an end effector loading device and a surgical trocar into a single device, and providing the capability to organize and deploy a plurality of end effectors, complexity of procedures involving the end effectors can be significantly reduced. Moreover, certain embodiments of the devices and methods described herein can provide other features, such as the ability to pivot an end effector relative to the loading device or coupling feedback indicators, to further improve a surgical procedure.

Figure 1A:
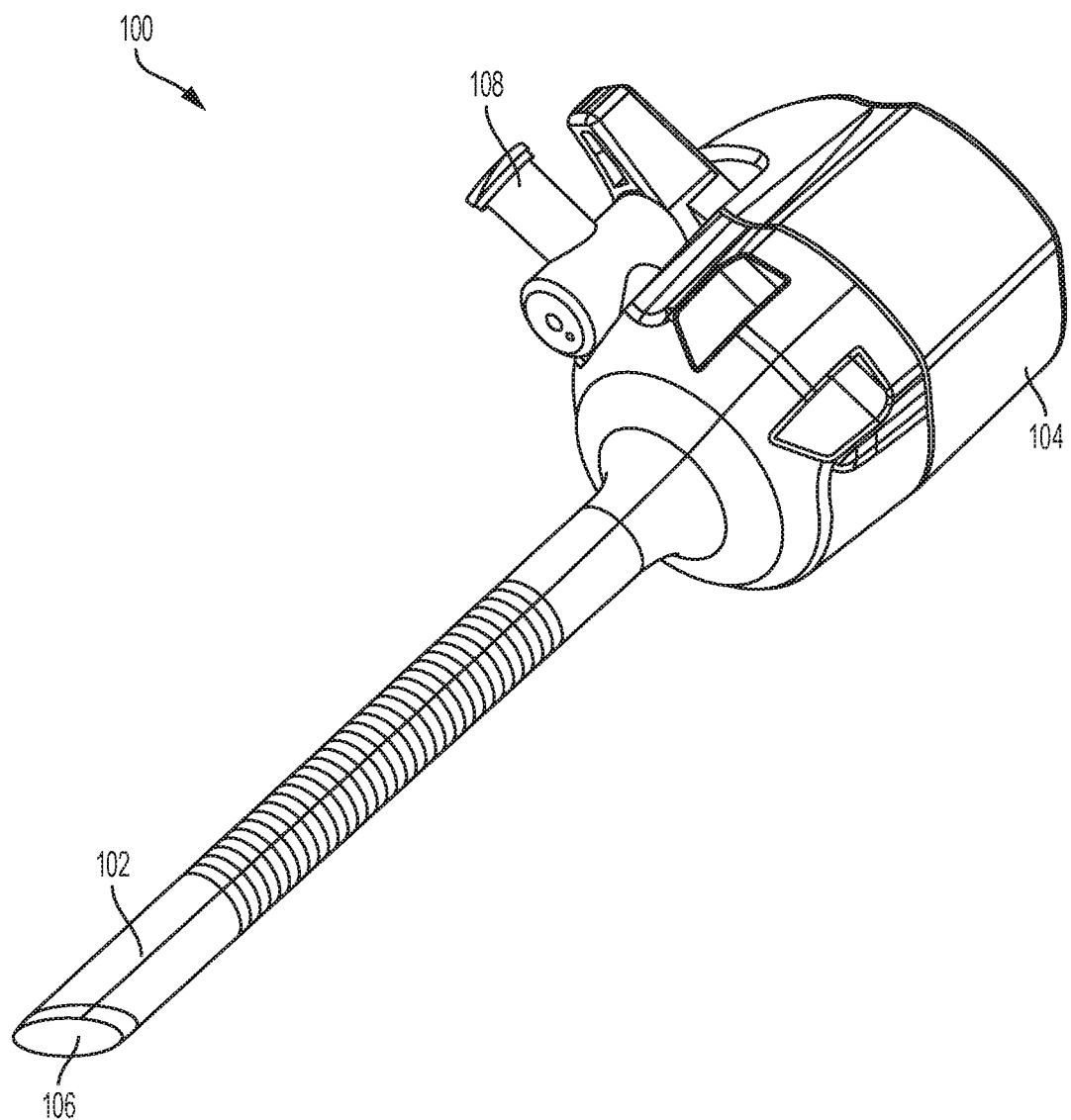
FIG. 1A is a perspective view of one embodiment of a prior art surgical trocar.
Figure 1B:
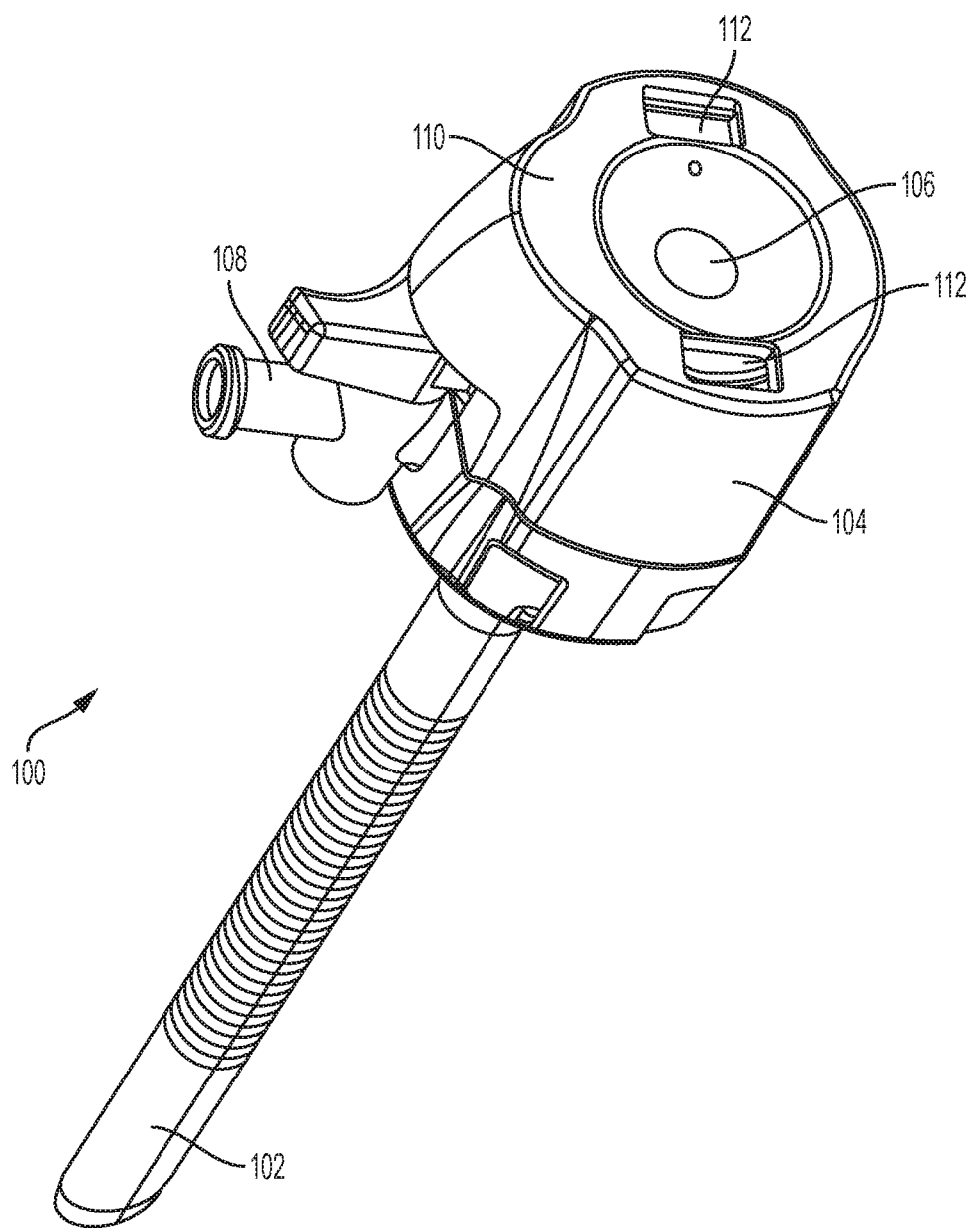
FIG. 1B is an alternative perspective view of the surgical trocar of FIG. 1A.
Figure 2:
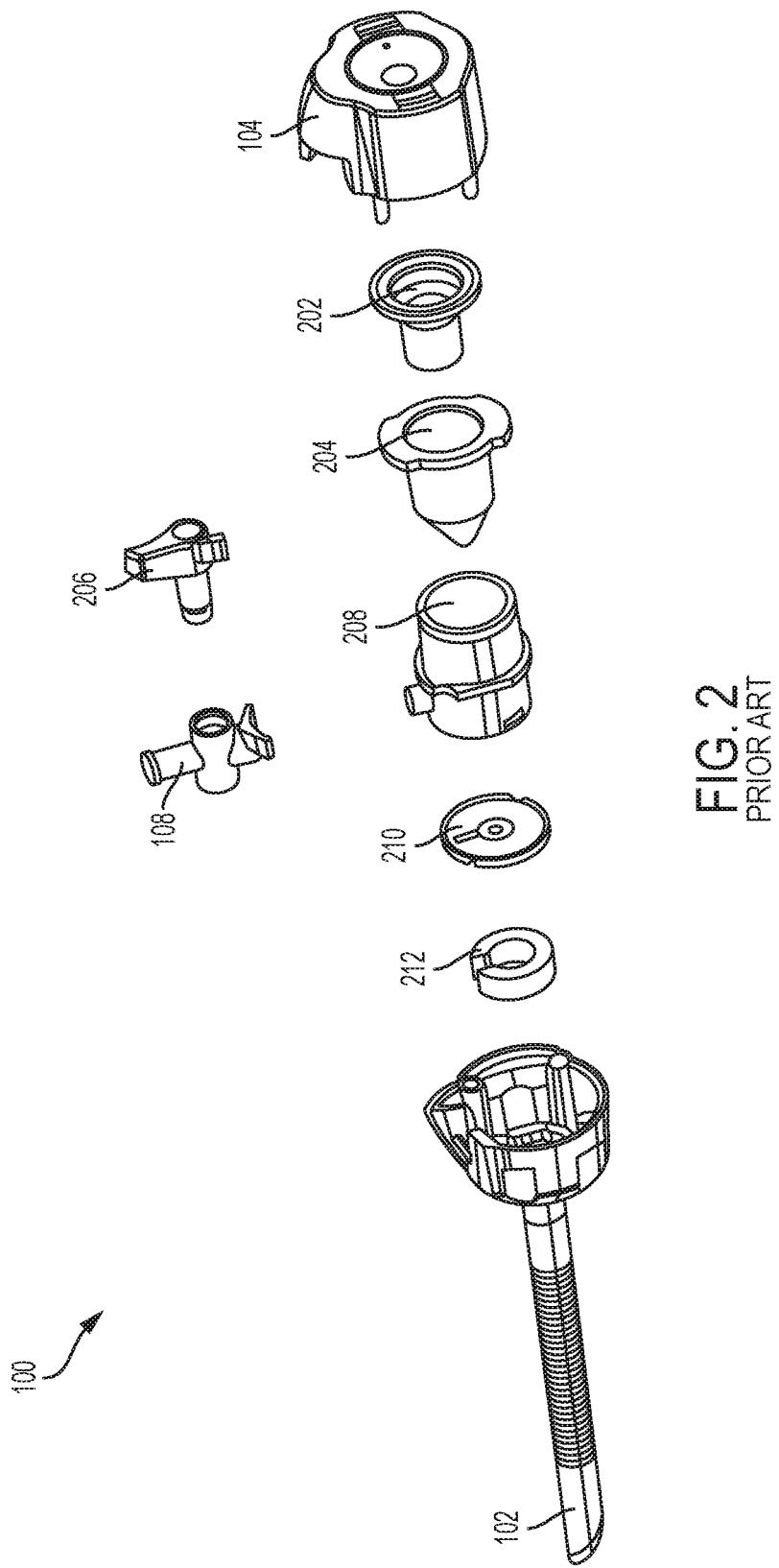
FIG. 2 is an exploded view of the surgical trocar of FIG. 1A.

FIGS. 1A-2 illustrate one embodiment of a surgical trocar 100 known in the art that can be used in connection with the devices and methods described herein. The illustrated trocar 100 is similar to trocars sold under the trade name ENDOPATH XCEL® by Ethicon Endo-Surgery, Inc. of Cincinnati, Ohio, though any other trocar known in the art can also be employed with, or easily adapted to be employed with, the devices and methods described herein. The trocar 100 generally includes a distal trocar sleeve 102 that is coupled to a proximal trocar housing 104.

The trocar 100 can have a lumen or working channel 106 extending therethrough and one or more seals (see FIG. 2) can be disposed across the working channel between the distal sleeve 102 and proximal housing 104. Further, an insufflation port 108 can be included to permit the introduction of insufflating gas, such as carbon dioxide, to help maintain pneumoperitoneum during a procedure.

The trocar housing 104 can include a proximal surface 110 configured to couple with, for example, an obturator (not shown) that can be utilized to help pass the trocar 100 through tissue. The trocar housing 104 can also include at least one mating element configured to aid in coupling the obturator to the trocar 100. In the illustrated embodiment, for example, the at least one mating element includes a plurality of recesses 112 configured to receive corresponding protrusions formed on the obturator (not shown). Further details on an exemplary coupling between an obturator and a trocar can be found in U.S. Pat. No. 8,034,032 to Voegele et al., entitled "Multi-Angled Duckbill Seal Assembly," which is hereby incorporated by reference.

Trocars are made in a variety of sizes and are typically denoted by a diameter of the working channel 106. This measure represents the largest width or diameter instrument that can be passed into a patient's body through the trocar. In the case of ENDOPATH XCEL® trocars, for example, the working channel is typically 5 mm or 12 mm in diameter. The smaller of the two sizes is typically utilized to introduce end effectors and other surgical instruments, while a visual scope is often introduced through the larger size working channel. Of course, these are not limitations on the size and intended use of a trocar, but merely examples.

Beyond the basic components described above, the various seals of a trocar are important for maintaining pneumoperitoneum and can be somewhat complex. FIG. 2 illustrates an exploded view of the trocar 100 including its various internal components in this non-limiting exemplary embodiment. From the proximal end of the trocar 100, a first instrument seal 202 is shown. The instrument seal 202 commonly has a round aperture in its center that is coaxially aligned with the working channel 106. The instrument seal 202 is configured to form a seal around, for example, a round-shape scope or instrument being passed through the trocar working channel. In some embodiments, when no instrument is present the aperture can remain open, i.e., it does not completely collapse to seal off proximal and distal portions of the working channel 106.

The instrument seal 202 can be located proximal to a "duckbill" seal 204 that is configured to seal the working channel 106 when no instrument is present. The shape of the duckbill seal 204, having opposed sidewalls that form a straight lip, can be effective to seal the channel in the absence of an instrument, but often fails to form a tight seal around an instrument. This is one reason for including two seals in series that have different shapes and purposes. Of course, a number of other seal shapes, numbers, and configurations are known in the art and can be employed with the devices and methods described herein.

The illustrated trocar 100 also includes an insufflation port valve 206 and inner housing 208 that surrounds the seals 202, 204. Finally, the illustrated embodiment includes a fluid remover assembly formed by a scraper 210 and a sorbent member 212. The fluid remover assembly is configured to remove bodily or other fluids that might be present on an instrument as it is retracted back through the working channel of the trocar proximally. In particular, the scraper 210, which can be formed from a molded polyisoprene and has a central opening coaxially aligned with the working channel 106, presses against an instrument and removes fluid as the instrument is moved relative thereto. The scraper 210 can include a series of radial channels (not shown) formed therein and extending from the central opening. The channels will have a capillary effect and allow fluid to flow radially outward away from the central opening of the scraper 210. This fluid will then be absorbed by the sorbent member 212 that is in contact with an outer portion of the scraper 210. The sorbent member 212 can be formed from, e.g., a polyolefin or other sorbent material.

As noted above, the trocar 100 and other embodiments thereof are often used during minimally invasive procedures to provide a means of accessing the interior of a patient's body. Further, they are commonly used in connection with percutaneously-inserted instruments in order to pass modular end effectors into the patient's body. These end effectors can then be coupled to the narrow distal end of the percutaneous instrument to allow the instrument to perform a variety of tasks. For example, one embodiment of a modular end effector can include a pair of jaws that can be actuated by relative movement of two concentric shafts of a percutaneously-inserted instrument. The shafts can easily be passed through tissue without the use of a trocar or other access device, and the jaws can be coupled thereto in vivo to turn the shafts into a useful tool for grasping and manipulating tissue.

Challenges with using these types of instruments typically arise in connection with the process of coupling, decoupling, or exchanging the modular end effectors with the distal end of the percutaneously-inserted instrument. The process typically involves a separate loading device that grasps the end effector and is used to introduce the end effector into the patient's body by passing it through the working channel of the trocar 100. The loading device and instrument must then be properly aligned to insert the shaft of the instrument into a socket formed in the end effector. Completing this coupling process can require manipulating the loading device, the trocar it is passed through, and the percutaneously-inserted instrument simultaneously. Moreover, as the number of end effectors used increases, so does the complexity of the procedure and demands on the surgical team, as the end effectors must be tracked and organized, and each exchange requires the simultaneous manipulation of the components listed above.

Beyond the difficulty of manipulating multiple components simultaneously or managing a set of modular end effectors, it can also be difficult to achieve a desired alignment between the various components or to discern when a modular end effector is coupled to a given component (and can therefore be released from another component) in the confined and remote environment where the procedure takes place. In an attempt to address these issues, some surgeons and other users opt to pass the percutaneously-inserted instrument back out of the body through the trocar 100. This can allow the surgeon to directly manipulate the end effector and distal end of the instrument. However, passing the instrument through the trocar 100 from its distal end to its proximal end can damage the trocar seals. As shown in FIG. 2, the trocar seals (as well as the fluid removal assembly if present) are designed to accept instruments moving in a proximal-to-distal direction. Retraction of instruments initially passed in this manner is not problematic because the instrument shaft maintains the seal in an open position and prevents inadvertent deformation of the seals during proximal retraction. When an instrument is initially passed in a distal-to-proximal direction, however, the instrument can deform or destroy the trocar seals 202, 204.

Figure 3A:
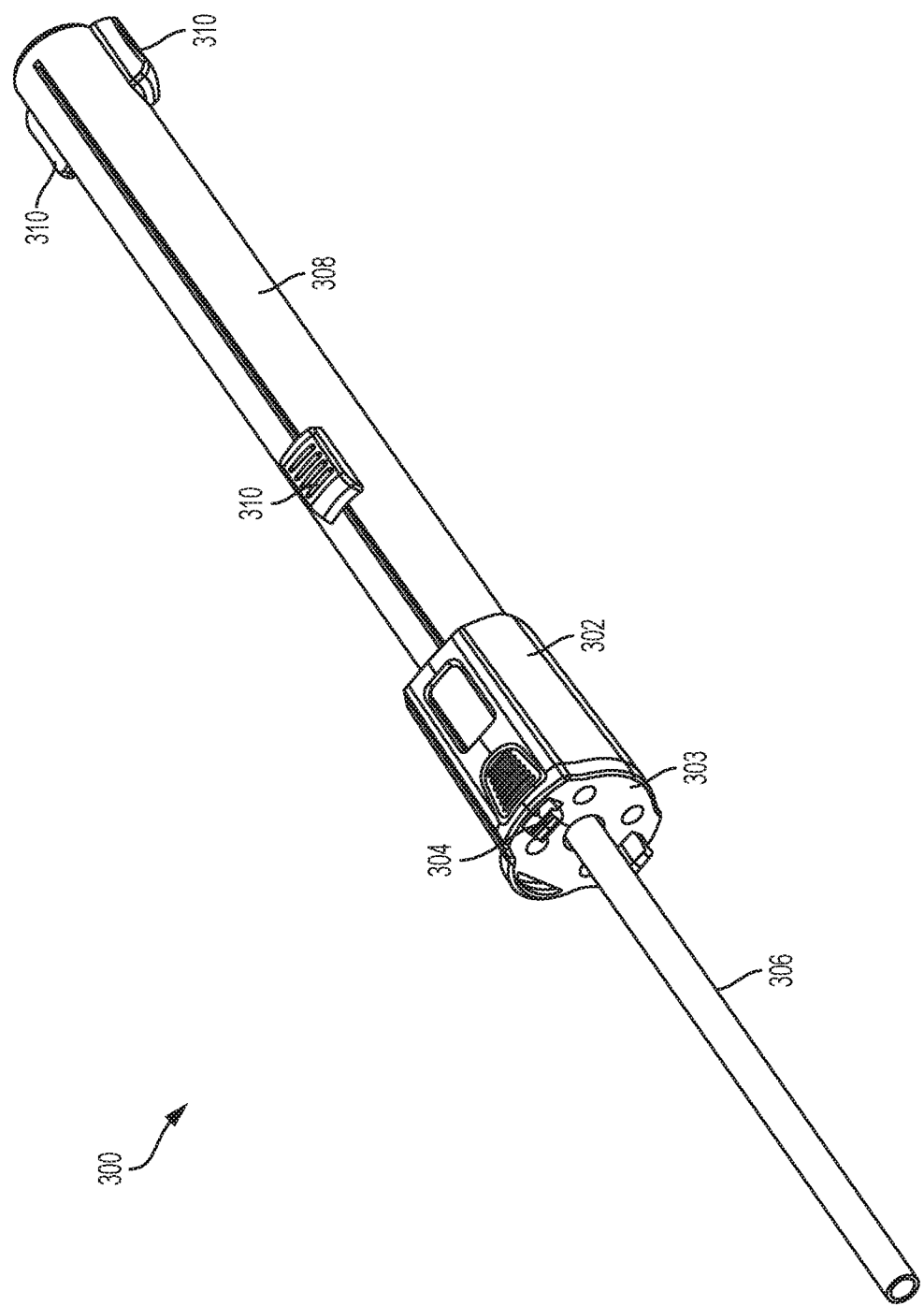
FIG. 3A is a perspective view of one embodiment of a surgical end effector loading device.
Figure 3B:
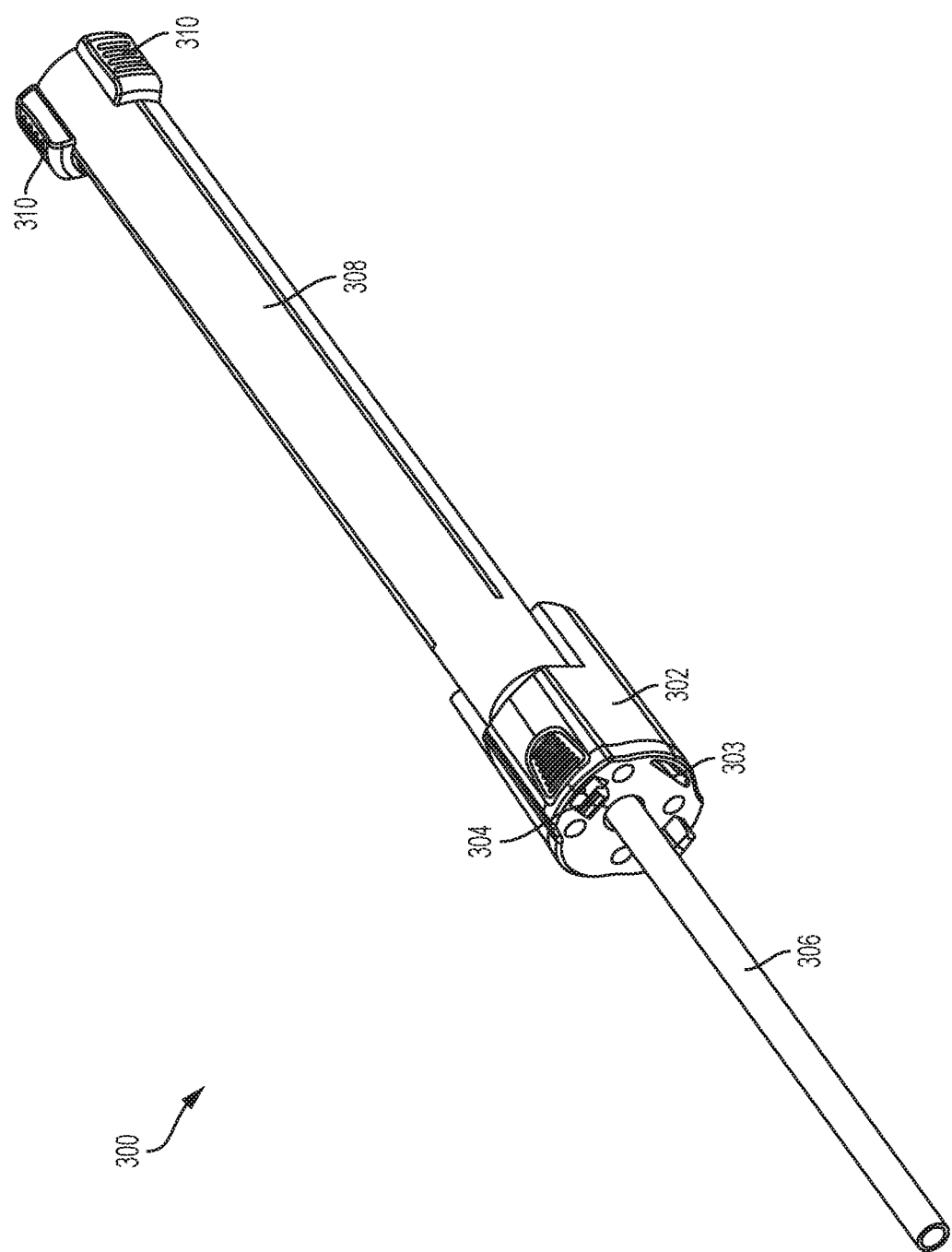
FIG. 3B is an alternative perspective view of the device of FIG. 3A.

FIG. 3A-3C illustrate one embodiment of a surgical end effector loading device 300 that addresses these and other challenges. The device 300 generally includes a housing 302 with a distal portion 303 that is configured to abut against a proximal end of a surgical trocar. The device 300 also includes at least one mating element 304 that is coupled to the housing 302 and configured to interface with a complementary mating element of a surgical trocar (e.g., mating elements 112 of trocar 100) to restrict movement of the housing relative to the trocar. A deployment lumen 306 extends from the distal portion 303 of the housing 302 and is configured to align with and extend into a working channel of a surgical trocar. Proximal to the deployment lumen 306 is an end effector repository 308 that includes a plurality of end effector lumens formed therein that can house a modular surgical end effector. The repository 308 in the illustrated embodiment is a carousel that can be rotated to align any of the end effector lumens with the deployment lumen 306. An advancer 310 can then be used to move a surgical end effector from the repository 308 into the deployment lumen 306 for delivery into a patient's body through a surgical trocar.

Figure 4A:
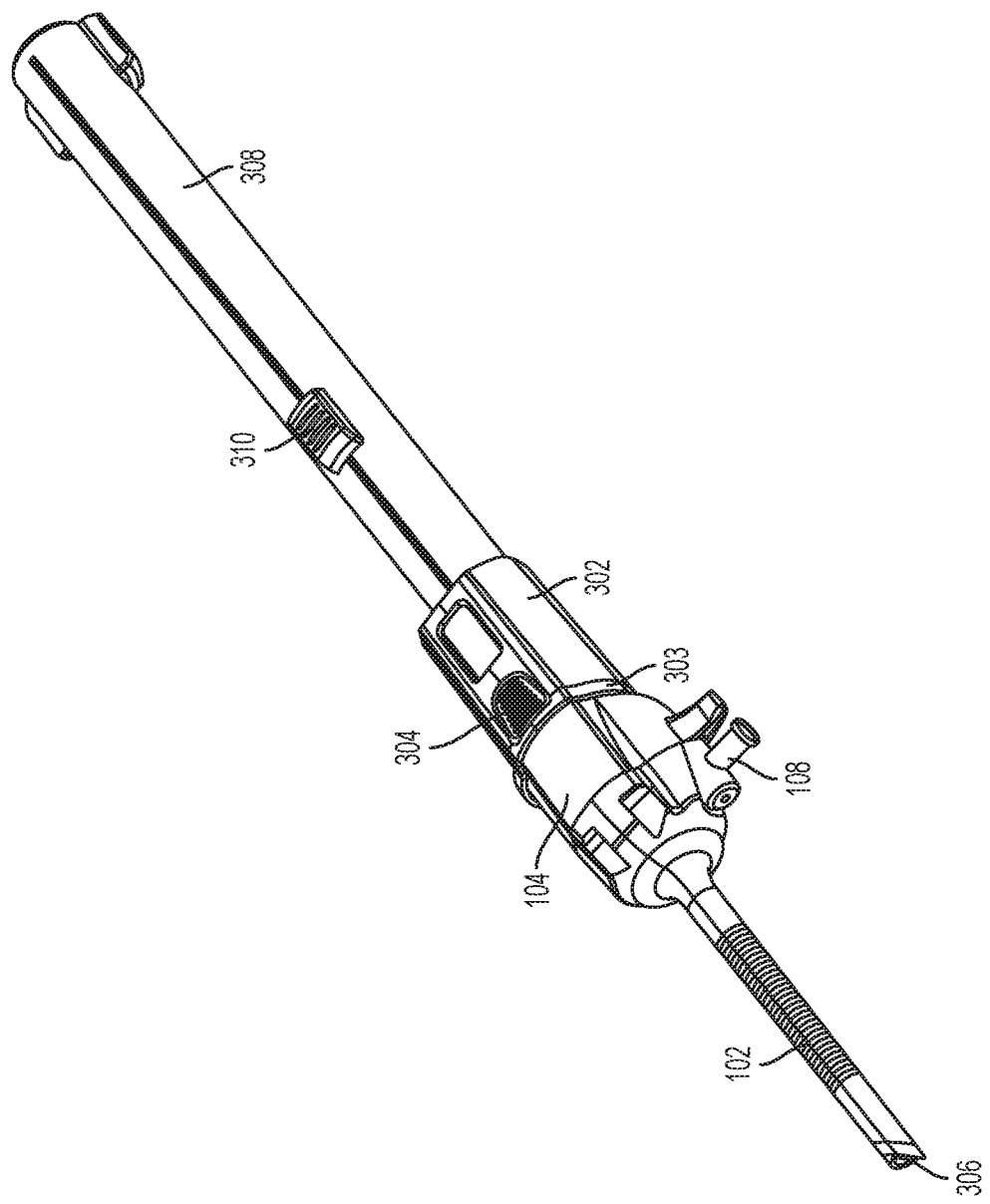
FIG. 4A is a perspective view of an assembly that includes the device of FIG. 3A coupled to the trocar of FIG. 1A.
Figure 4B:
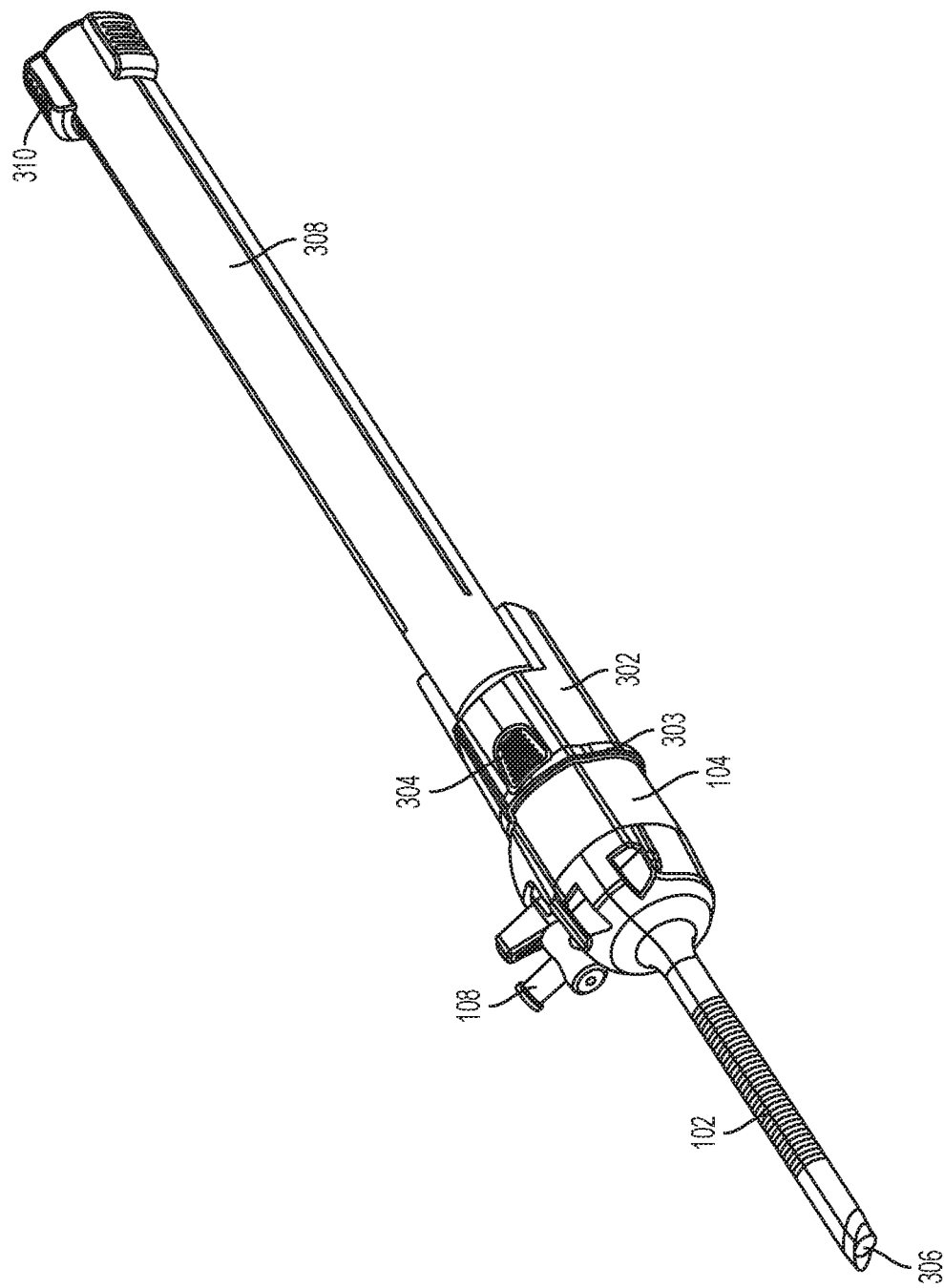
FIG. 4B is an alternative perspective view of the assembly of FIG. 4A.

FIGS. 4A and 4B illustrate views of the loading device 300 coupled to the trocar 100. As shown in the figures, the distal-facing first portion 303 of the housing 302 can abut against the proximal surface 110 of the trocar 100. Further, the deployment lumen 306 can extend through the working channel 106 of the trocar 100 such that a surgical end effector can be delivered out of a distal end of the trocar sleeve 102. Although a distal end of the deployment lumen 306 is shown extending from a distal end of the working channel 106 of the trocar 100, other configurations are possible in which the distal end of the deployment lumen 306 remains proximal of the working channel distal end, or extends farther distally than shown.

Figure 4C:
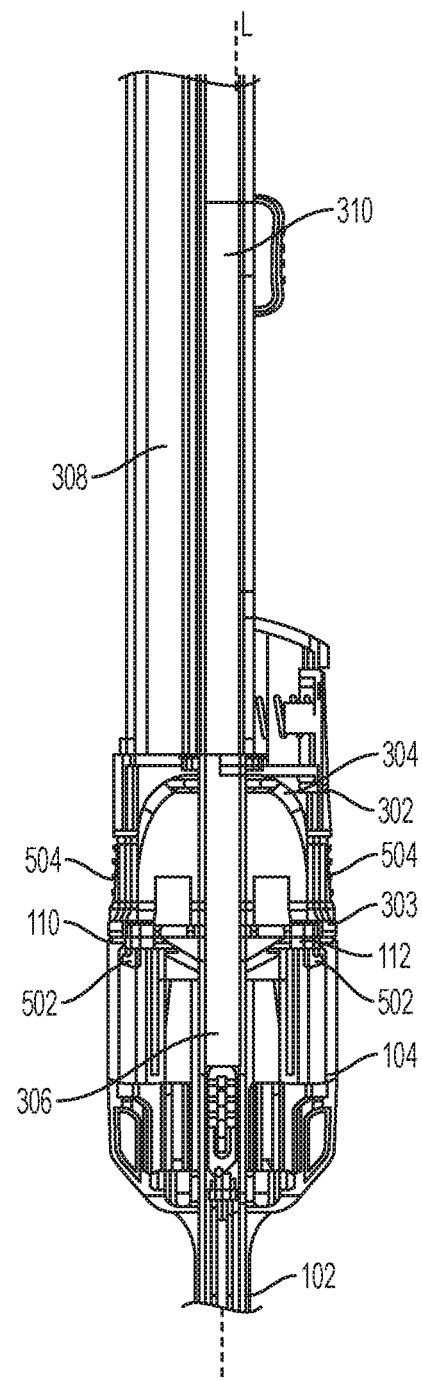
FIG. 4C is side cross-sectional view of the assembly of FIG. 4A taken along line A-A shown in FIG. 3C.
Figure 4D:
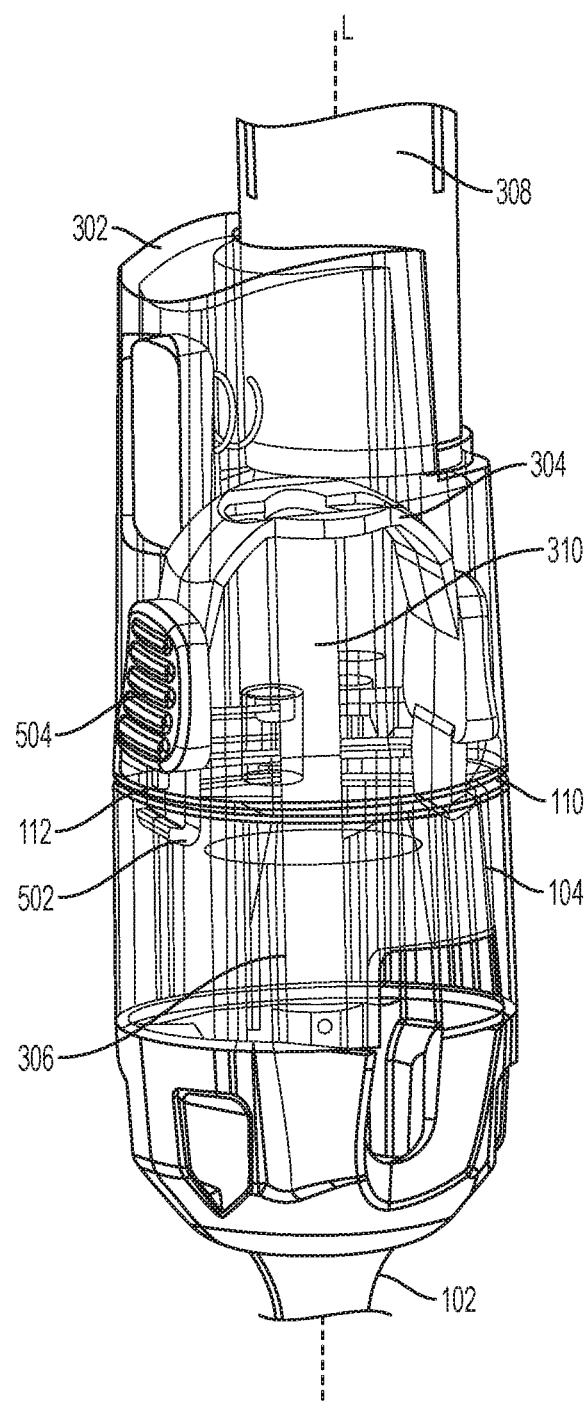
FIG. 4D is a partially-transparent perspective view of the assembly of FIG. 4A
Figure 5:
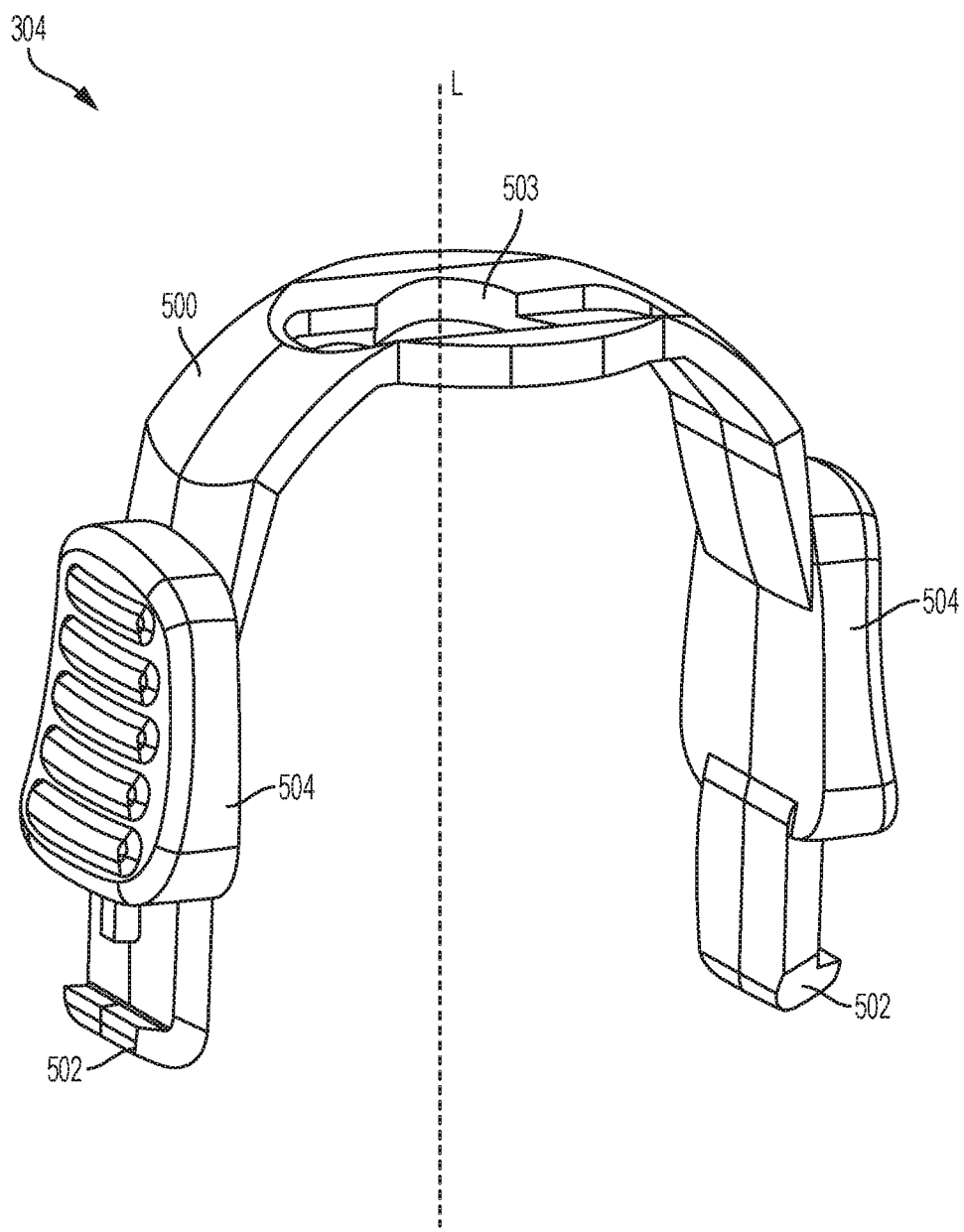
FIG. 5 is a perspective view of one embodiment of a mating element of the surgical end effector loading device of FIG. 3A.

The loading device 300 can be coupled to the trocar 100 via one or more mating elements formed on the device that interface with complementary mating elements formed on the trocar. FIGS. 4C-4D illustrate the coupling between the loading device 300 and the trocar 100 in more detail. As shown in the detail view of the mating element 304 in FIG. 5, the mating element can be in the form of a U-shaped frame 500 having hooks, barbs, or clips 502 formed on distal ends thereof. The U-shaped frame 500 can also include a central lumen 503 formed therein that is configured to receive the deployment lumen 306. The mating element 304 can be formed from a resilient material, such as an elastically deformable polymer or metal, and can be biased away from a longitudinal axis L of the mating element 304, and of the loading device 300. This biasing can aid the mating element 304 in interfacing with a recess formed in the trocar 100. The mating element 304 can also include opposed actuating surfaces 504 that can be depressed by a surgeon or other user in order to selectively decouple or release the loading device 300 from the trocar 100 when desired. The actuating surfaces 504 can include ridges or other surface features formed thereon to aid a user in grasping and depressing them. While the mating element 304 is illustrated as a single U-shaped frame 500 with opposed distal end features 502, in other embodiments a plurality of separate mating elements can be employed at various positions around the deployment lumen 306 that is configured to extend into a working channel of the surgical trocar 100, or a differently-shaped frame can be employed, e.g., a T-shaped or cross-shaped frame having four distal mating features.

Referring back to the cross-sectional and partially transparent views of FIGS. 4C and 4D, the interaction between the mating element 304 of the loading device 300 and the complementary mating elements 112 of the trocar 100 can be observed. In particular, the hooks 502 formed at the distal ends of the U-shaped mating element 304 extend into the recesses 112 formed in the proximal surface 110 of the trocar 100. Further, due to the outward bias of the mating element 304, the hooks 502 engage an underside of the proximal surface 110 of the trocar 100 and prevent the loading device 300 from being drawn away from the trocar axially (i.e., along a longitudinal axis L). In addition, the generally rectangular cross-sectional shape of the mating element 304 can substantially fill the generally rectangular recesses 112, thereby preventing the loading device 300 from rotating or otherwise moving radially relative to the longitudinal axis L. Accordingly, the mating element 304 of the loading device 300 can be configured to restrict movement of the loading device 300 relative to the trocar 100 in all degrees of freedom.

To release the loading device 300 from the trocar 100 (e.g., at the conclusion of a surgical procedure, or if a different loading device with a different set of surgical end effectors is to be passed through the trocar working channel 106), a surgeon or other user can depress the opposed actuating surfaces 504 of the mating element 304 in order to move the distal hooks 502 against any biasing force towards the longitudinal axis L. This movement of the hooks 502 can allow the hooks to disengage from the underside of the proximal surface 110 of the trocar 100 and pass through the recesses 112 formed therein. Accordingly, the loading device 300 can be selectively coupled to the trocar 100.

The illustrated mating element 304 is just one embodiment of a mating element, however, and a variety of other configurations are also possible. For example, the configuration of distally-protruding hooks 502 on the loading device 300 and recesses 112 formed in the trocar 100 can be reversed such that hooks protruding from the trocar proximal surface can be received within recesses formed in a distal-facing portion 303 of the loading device housing 302. In still other embodiments, the bias and orientation of the hooks 502 can be reversed such that they are biased radially inward toward a longitudinal axis L, rather than radially outward as shown. Moreover, the hooks 502 can be positioned on an outer surface of the loading device 300 and configured to engage with recesses, shelves, or other surface features formed on an outer surface of a proximal portion of the trocar 100. There are a variety of other known coupling mechanisms in the art that can also be employed. Regardless of the particular configuration of the mating elements, the loading device 300 can include at least one mating element that is complementary to at least one mating element formed on the trocar 100. In many cases, the at least one mating element on the trocar can be pre-existing and utilized to attach other trocar accessories, such as an obturator.

Still further, certain embodiments of the at least one mating element 304 can be configured to permit at least some relative movement between the loading device 300 and the trocar 100. For example, in some embodiments the at least one mating element 304 can include at least one cylindrical rod or other projection that extends into a recess formed in the trocar 100 without utilizing a hook or other feature to positively latch on to the trocar. In such an embodiment, the loading device 300 can be prevented from moving radially with respect to, or rotating about, a longitudinal axis L, but can be permitted to move axially relative to the longitudinal axis L. In still other embodiments, a distal-facing portion 303 of the loading device housing 302 can include an outer wall configured to extend over a proximal portion of the trocar 100, and one or more splines can be formed on both the loading device 300 and trocar 100 to prevent relative rotation or radial movement with respect to the longitudinal axis L. In still other embodiments, rotation about the longitudinal axis L can be permitted while movement in other directions can be restricted. Of course, any combination of various mating elements can be utilized as known in the art, and need not conform to the specific examples provided herein.

Figure 6:
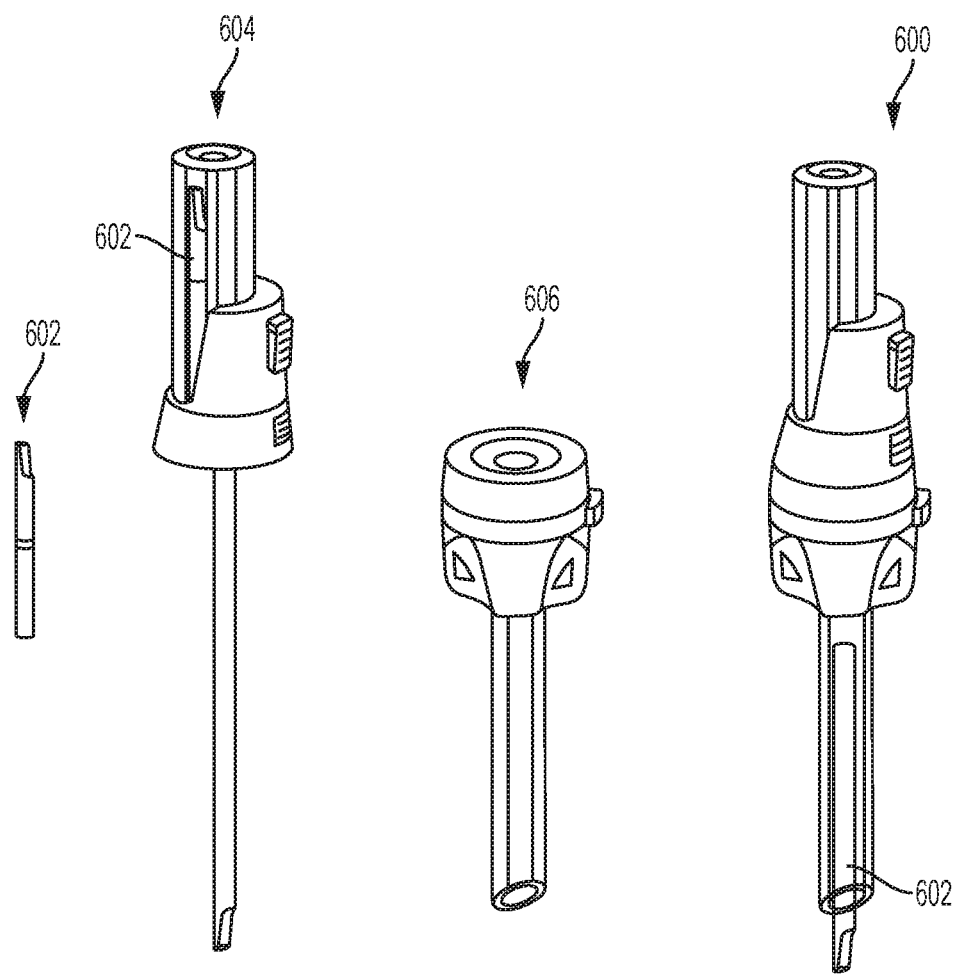
FIG. 6 is a perspective view of components of one embodiment of a surgical kit.

FIG. 6 illustrates various components that can form a surgical instrument kit according to the teachings of the present disclosure. The kit can include a modular surgical end effector 602 (or a plurality thereof), an end effector loading device 604 similar to the device 300 described above, and a surgical trocar 606 similar to the trocar 100 described above. In use, one or more surgical end effectors 602 can be loaded within an end effector repository of the loading device 604. Loading the end effectors in this manner can aid in keeping the end effectors organized for easy selection and deployment during a surgical procedure. To this end, the walls of the end effector repository can be formed from a transparent material, or can include one or more viewports formed therein, to allow a user to observe which end effector lumens of the repository have end effectors loaded therein, and what type of end effector is available for deployment. The loaded end effector loading device 604 can then be coupled to the surgical trocar 606 in the same manner as an obturator or other trocar accessory. The end result is a single device that can be easily manipulated with one hand during a procedure (as opposed to a more traditional set-up where a separate trocar and loading device have to be simultaneously manipulated using at least two hands). Further, the end effector repository can selectively align any of its end effector lumens with a main deployment lumen in order to deliver any loaded end effector into a patient's body through the trocar 606. In the illustrated embodiment, this can be accomplished by rotating the carousel repository until the desired end effector lumen is aligned with the deployment lumen. Of course, the procedure can be reversed as well to return an end effector into an empty end effector lumen after use.

FIGS. 7A-7D illustrate the various components of the loading device 300 discussed above in greater detail. As shown in the figures, the housing 302 and deployment lumen 306 are an integrally formed component in this embodiment. This need not be the case in every embodiment. Moreover, the deployment lumen 306 can have any desired length and, in some embodiments, may be just a through-hole formed in the housing 302 or distal-facing portion 303. The at least one mating element 304 is sandwiched between the proximal housing 302 and the distal-facing portion 303, and the deployment lumen 306 passes through the central lumen 503 formed therein. At a proximal end of the device, the end effector repository 308 is coupled to the housing 302. The illustrated repository 308 is in the form of a rotatable carousel having three end effector lumens formed therein. An advancer 310 is slidably positioned within each end effector lumen of the repository and can be used to move an end effector from within the end effector lumen into the deployment lumen 306 and, ultimately, out a distal end thereof into a patient's body. Each advancer 310 can include an actuator 701 coupled thereto that extends beyond an outer diameter of the end effector lumen and can be directly manipulated by a user to control advancement of an end effector. Finally, a button 702 is included in housing 302 that can be used to selectively block the deployment lumen 306 and prevent any end effector from being advanced therethrough.

Figure 7A:
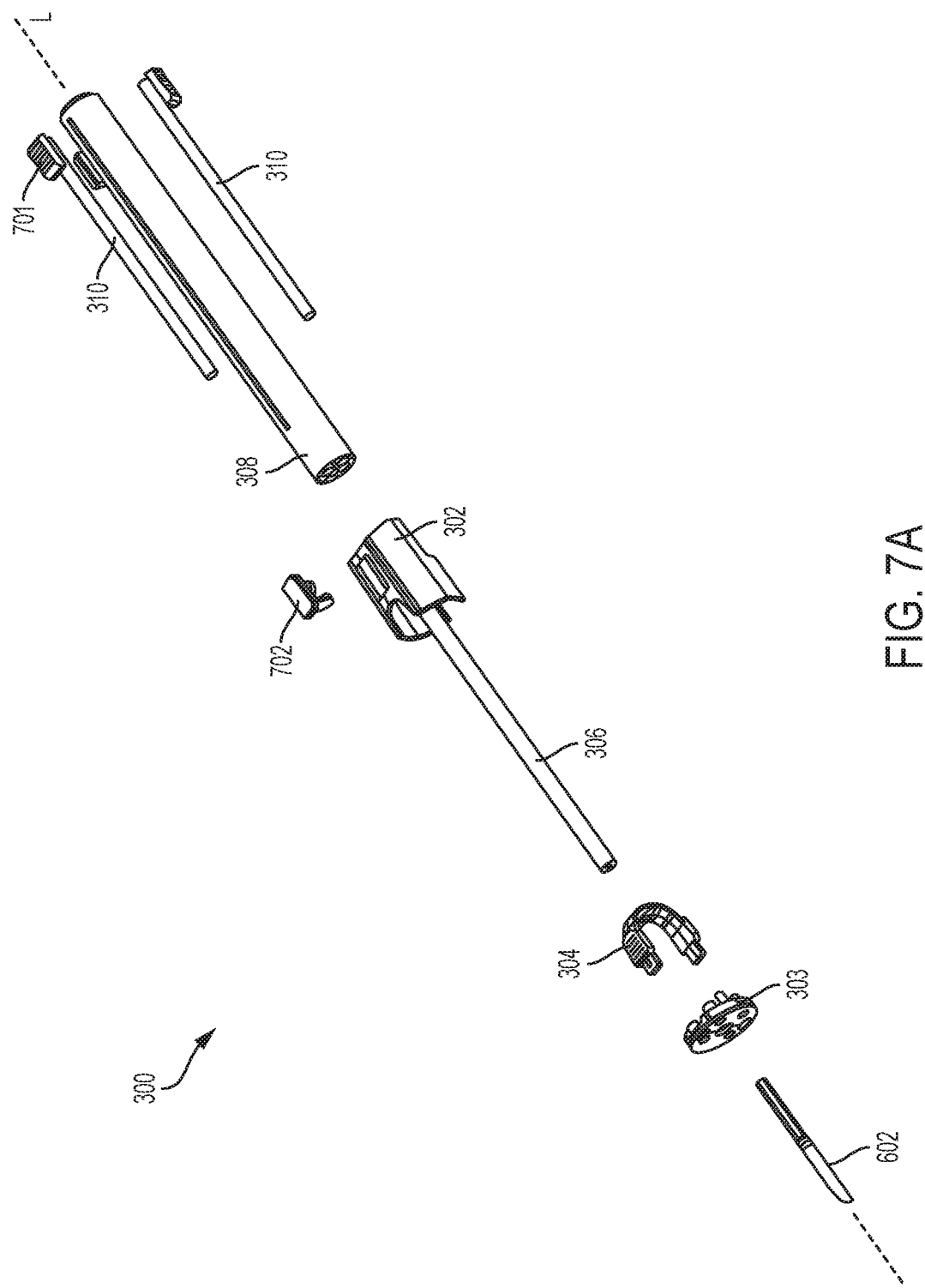
FIG. 7A is an exploded view of the device of FIG. 3A and one embodiment of a surgical end effector.
Figure 7B:
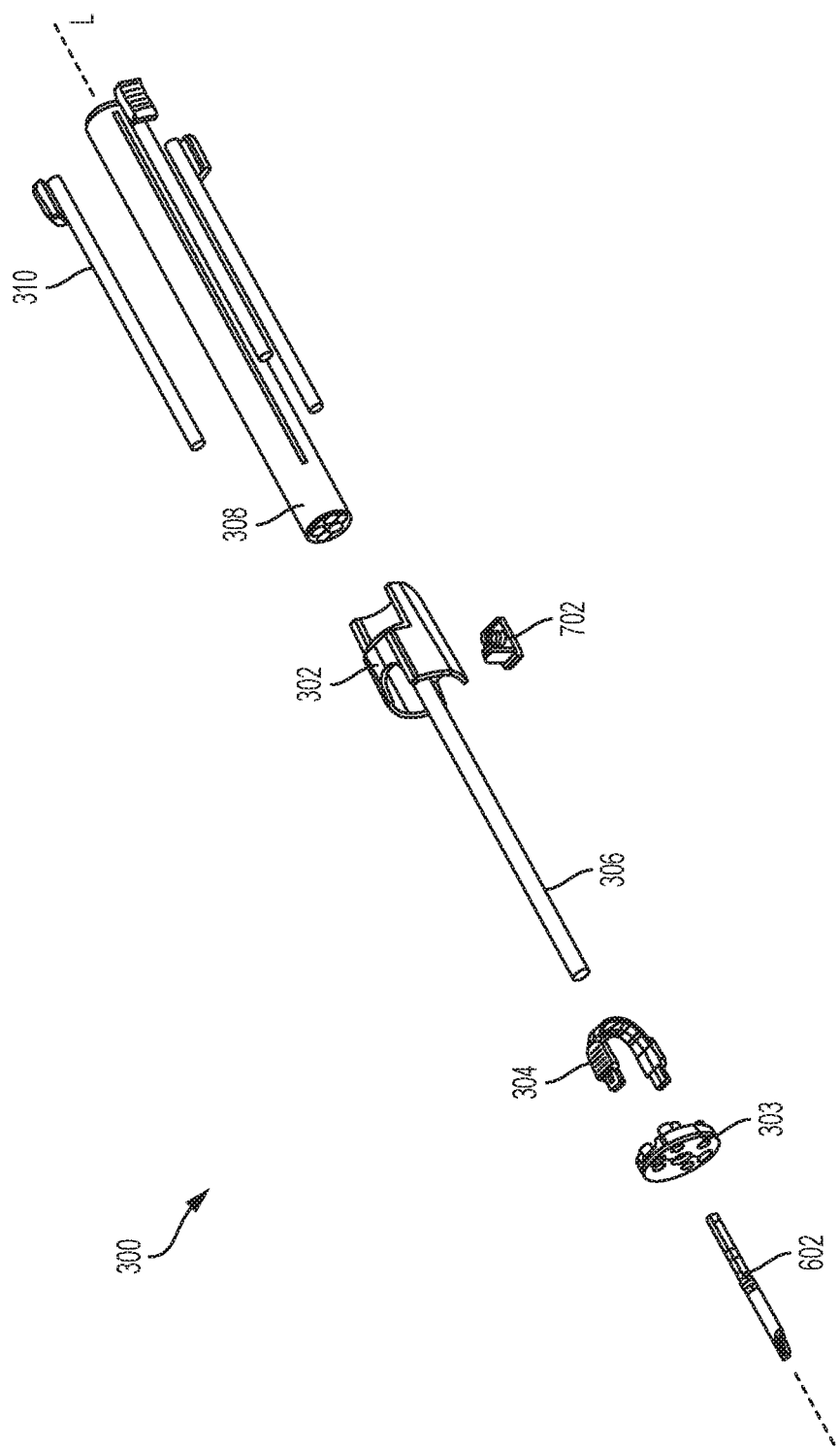
FIG. 7B is an alternative perspective exploded view of the device of FIG. 7A.
Figure 7C:
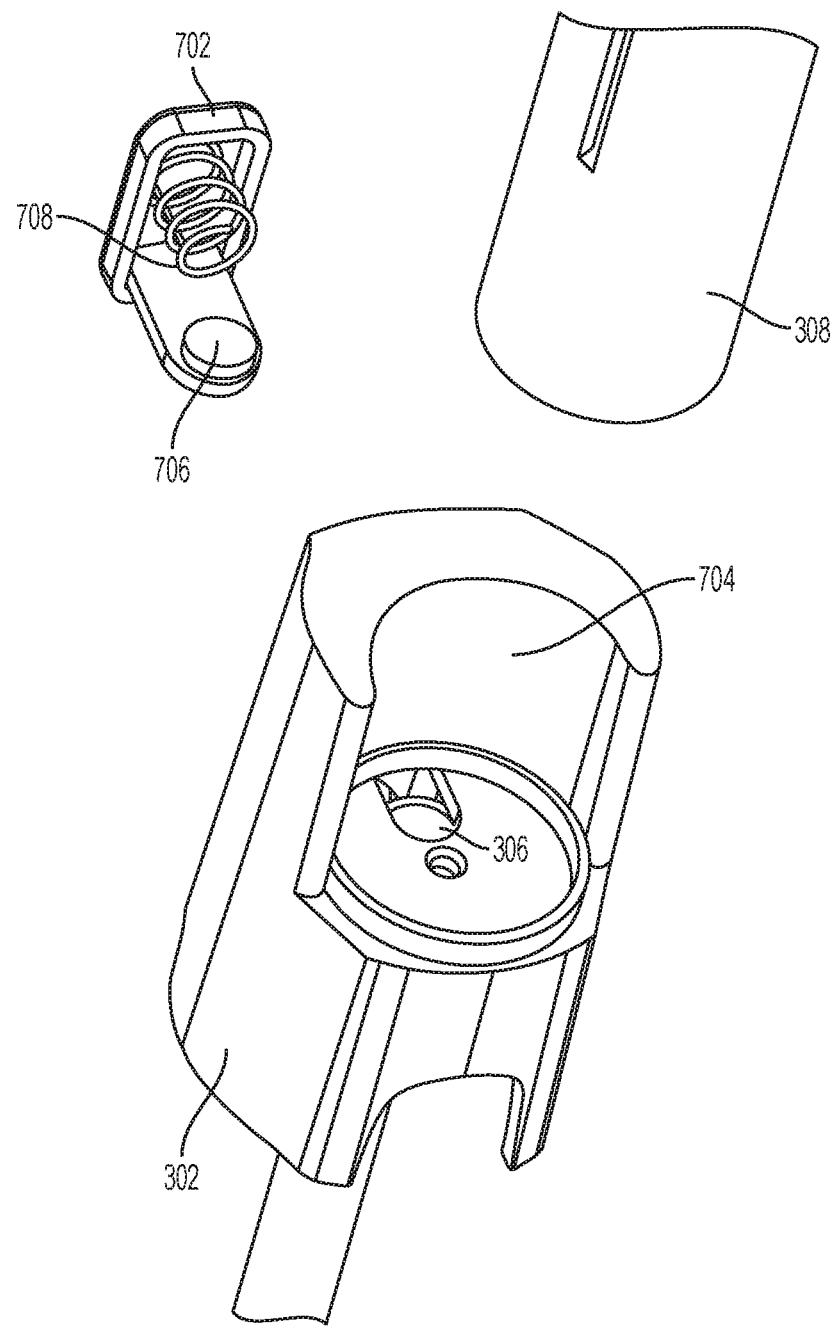
FIG. 7C is a detail view of a portion of the device of FIG. 7A.
Figure 7D:
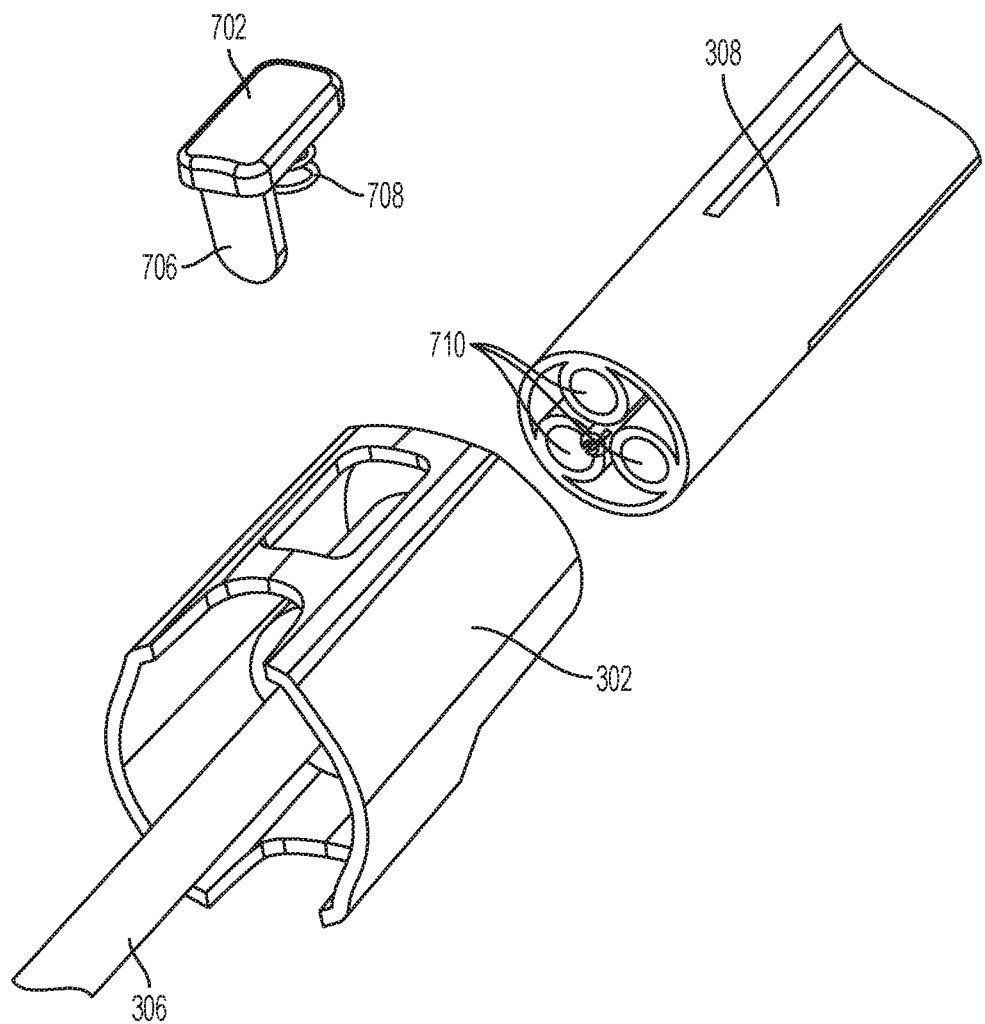
FIG. 7D is an alternative perspective view of the portion of the device shown in FIG. 7C.

FIGS. 7C and 7D illustrate the coupling between the housing 302 and the end effector repository 308 in greater detail. As shown in FIG. 7C, the housing 302 includes a cut-out 704 sized to receive the repository 308 and permit its rotation about a central axis. The deployment lumen 306 extends through the housing 302 such that it can be selectively aligned with any of the end effector lumens of the repository 308. Also illustrated in greater detail is the button 702, which includes a projection 706 that can fill the opening of the deployment lumen 306 to block the passage of any end effector therethrough. The button 702 is biased to an open position by biasing element 708 and, as a result, requires actuation to block the deployment lumen passage.

FIG. 7D illustrates the housing 302 and repository 308 from an alternative angle and shows the three end effector lumens 710 of the illustrated embodiment. As noted above, each lumen can have a longitudinal axis and can include a slidable advancer 310 configured to translate along the longitudinal axis of the lumen it is disposed within. Alternatively, a single advancer 310 can be configured to be used with all of the end effector lumens 710 by, for example, removably inserting the advancer into the desired end effector lumen. As noted above, the end effector repository 308 in the illustrated embodiment is in the form of a rotatable carousel having three end effector lumens 710. This is merely an exemplary embodiment, however, as repositories with a larger or smaller number of end effector lumens are possible. In addition, repositories with different shapes and mechanisms for selectively aligning a given end effector lumen with a deployment lumen are also possible. For example, an end effector repository with a rectangular shape can have a plurality of end effector lumens placed adjacent to one another along a single dimension thereof, and the repository could be configured to translate along that dimension to selectively align any of the end effector lumens with a deployment lumen.

Figure 8:
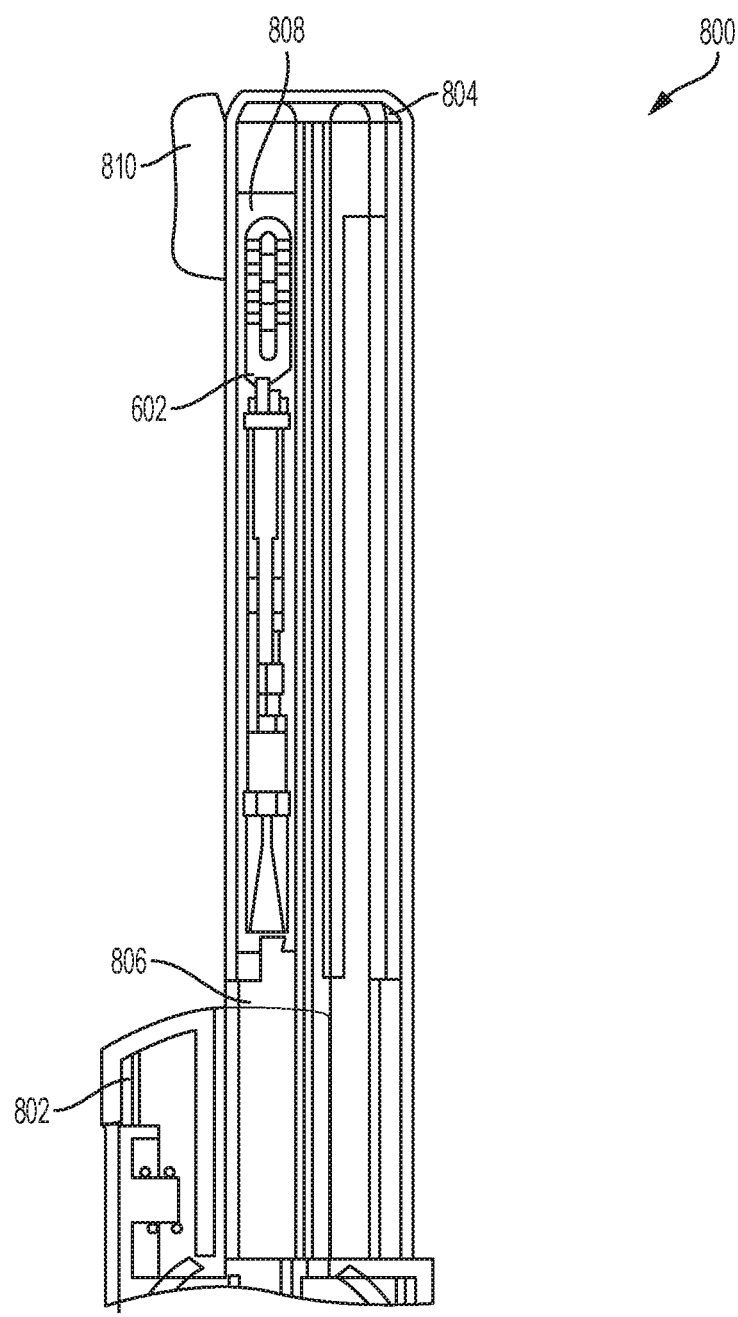
FIG. 8 is a side cross-sectional view of one embodiment of an end effector repository.
Figure 9A:
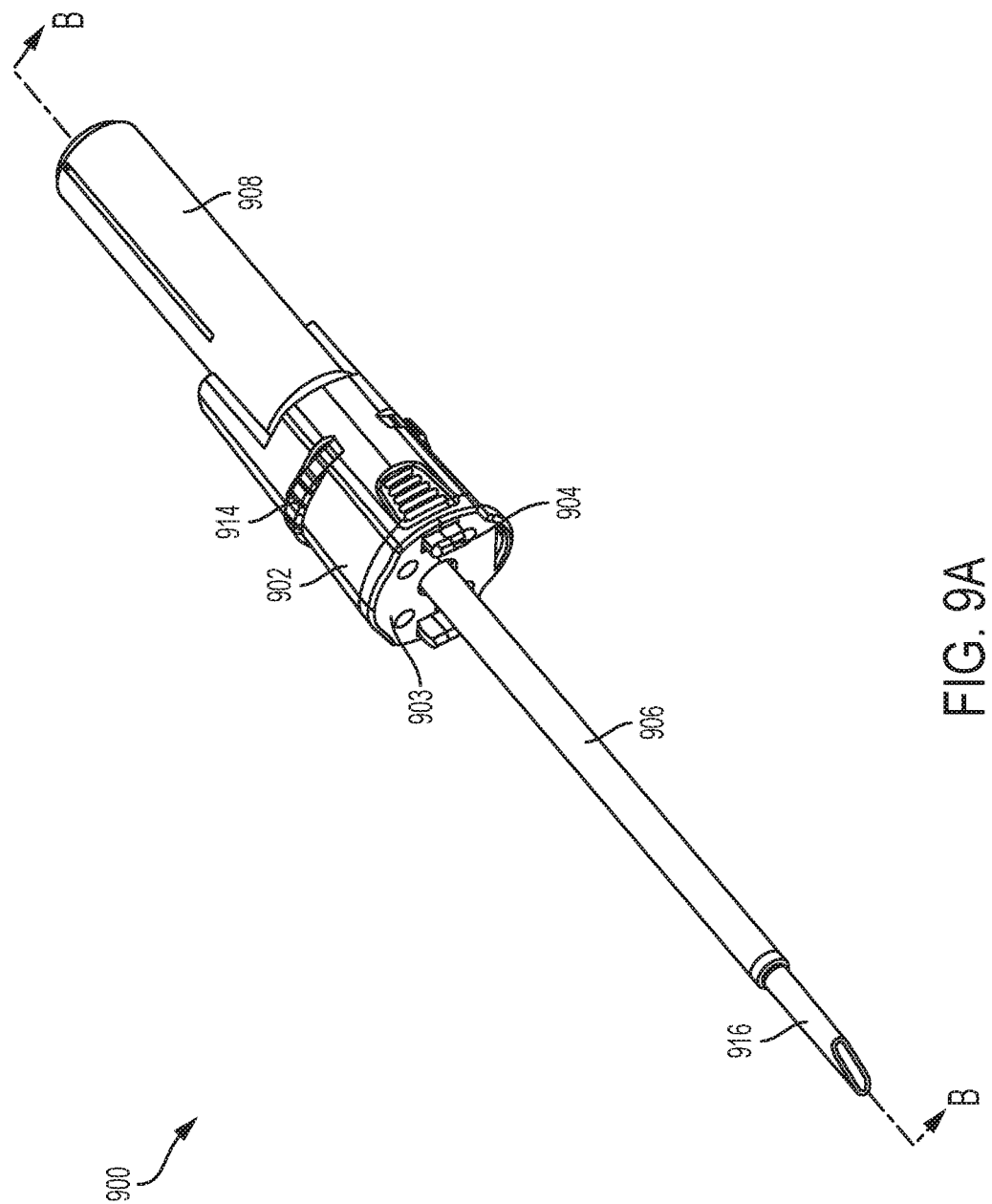
FIG. 9A is a perspective view of another embodiment of a surgical end effector loading device.
Figure 9B:
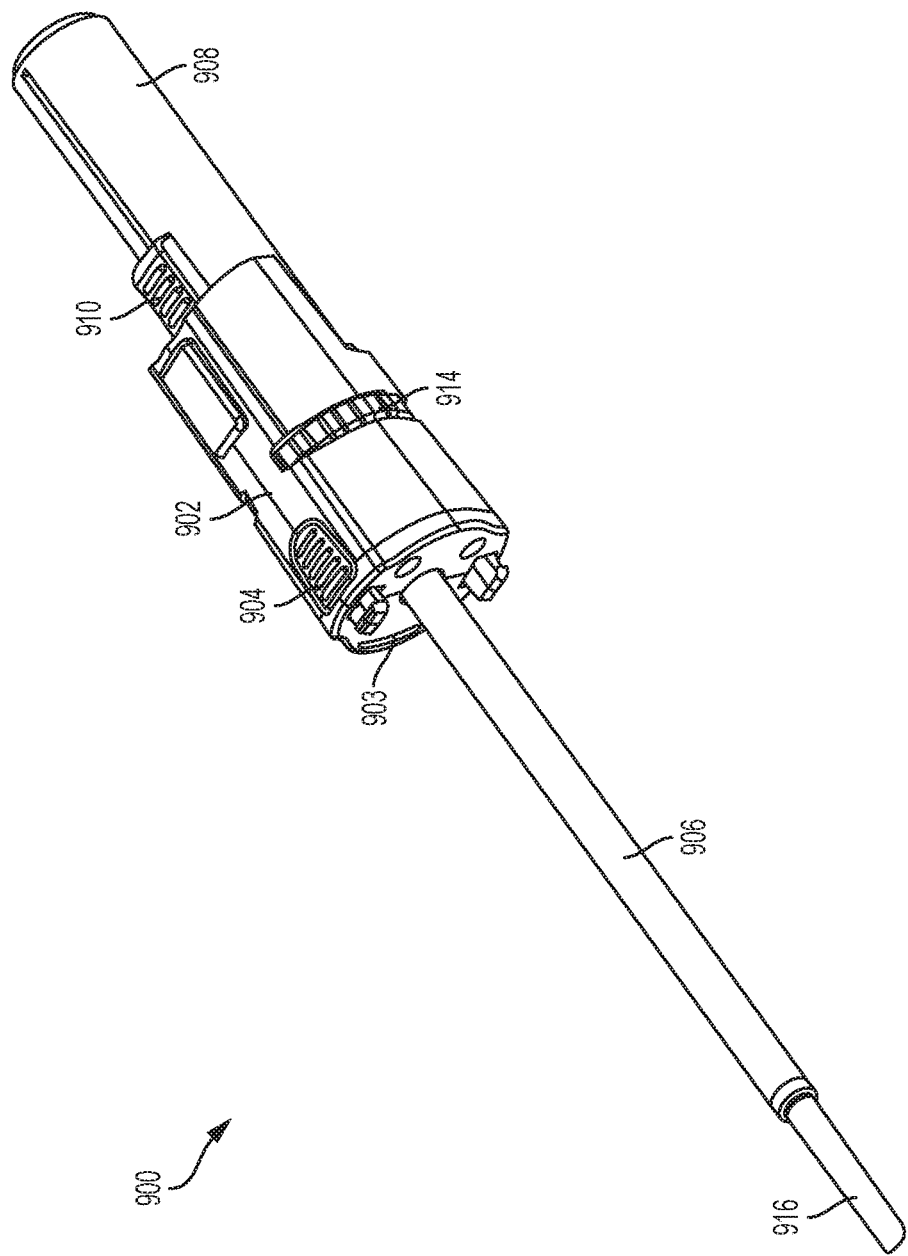
FIG. 9B is an alternative perspective view of the device of FIG. 9A.
Figure 10A:
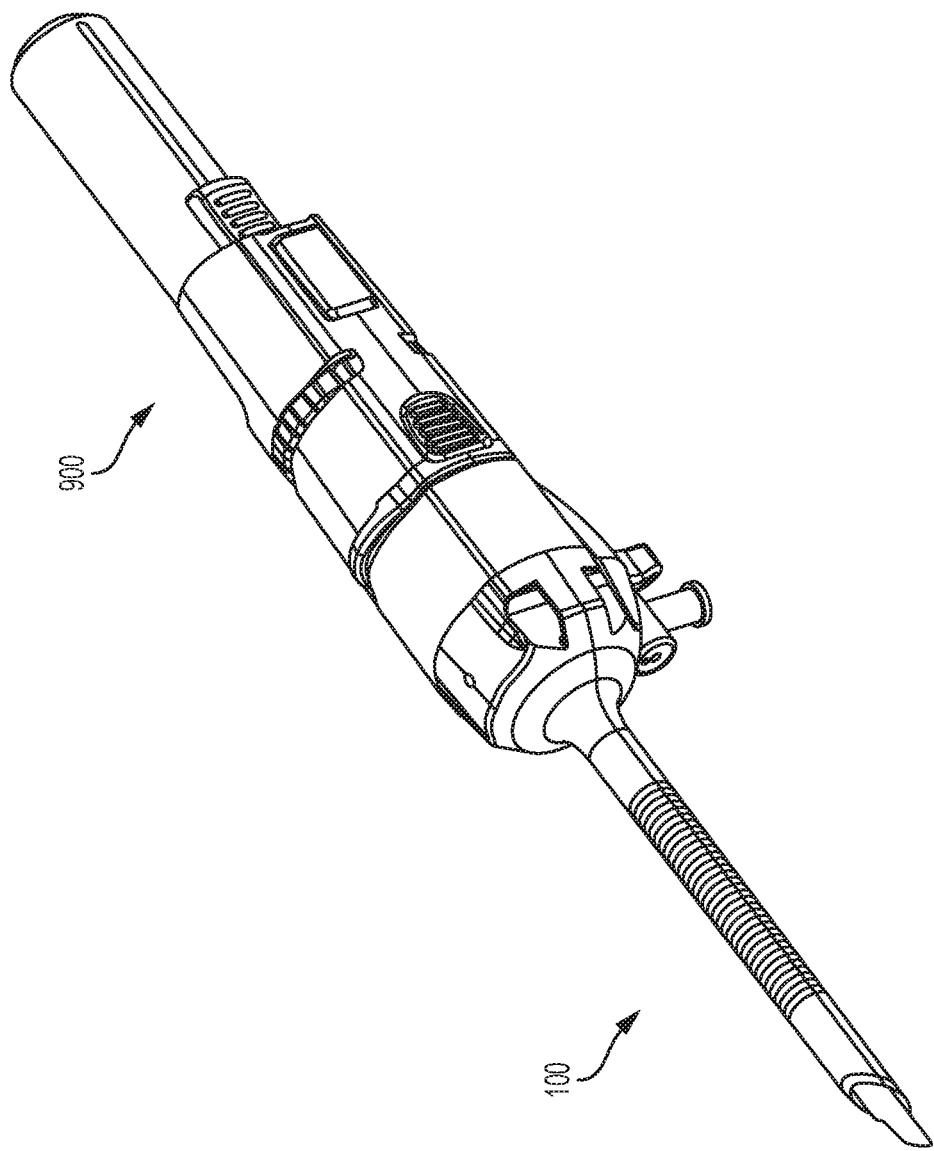
FIG. 10A is a perspective view of an assembly that includes the device of FIG. 9A coupled to the trocar of FIG. 1A.
Figure 10B:
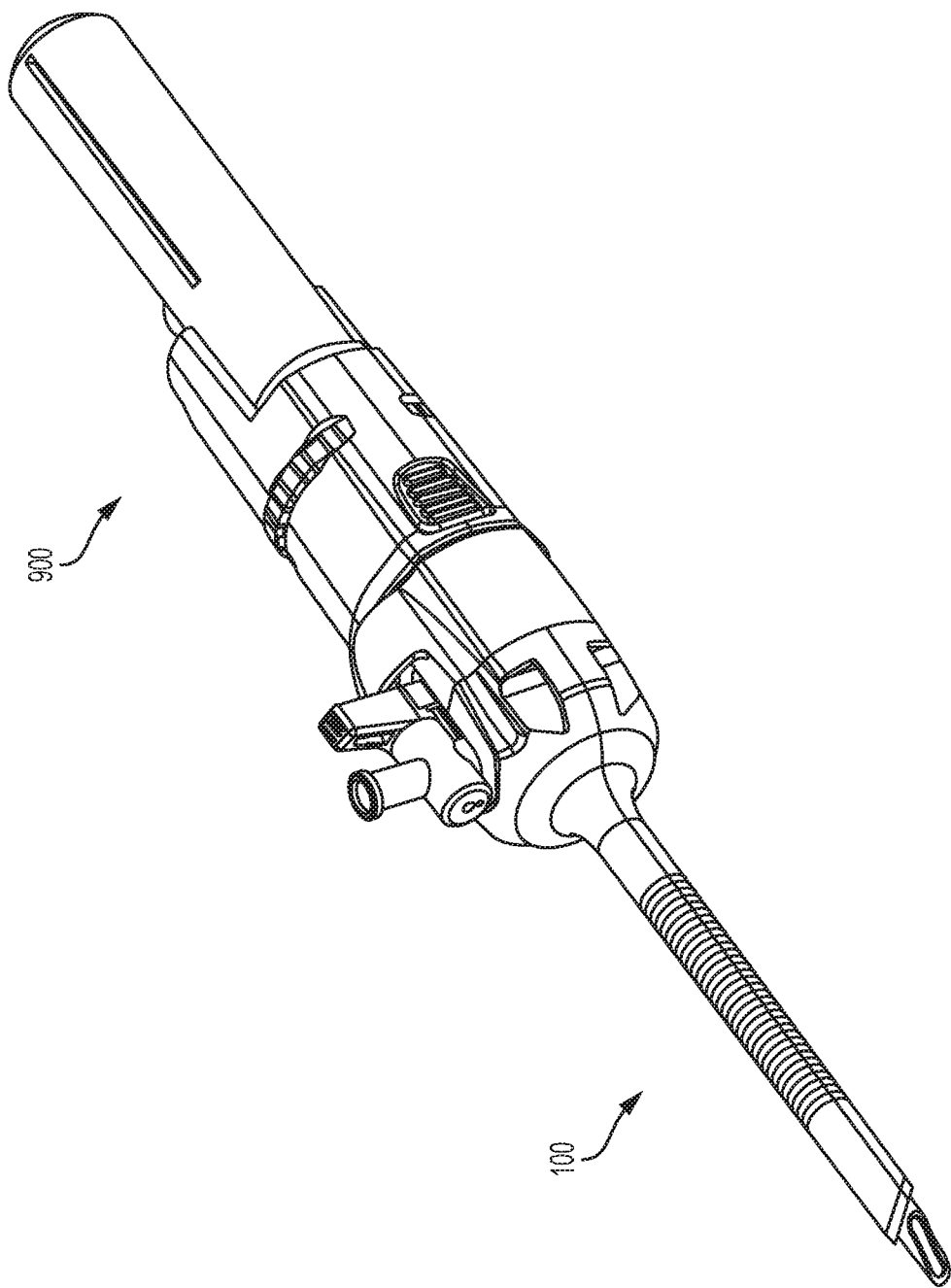
FIG. 10B is an alternative perspective view of the assembly of FIG. 10A.

The advancer 310 illustrated and described above includes an elongate shaft disposed within an end effector lumen 710 such that movement of the actuator 701 by a user can advance an end effector through the deployment lumen 306 to a distal end of the loading device 300. As noted above, however, the deployment lumen 306 can have any desired length, including a very short length. In such an embodiment, it can be desirable to include an advancer of much shorter length as well. In addition, some embodiments can employ a second advancer mechanism to control advancement of an end effector through the deployment lumen, as described in more detail below. In such embodiments, a shorter advancer within the end effector repository can also be desirable. FIG. 8 illustrates one embodiment of such a loading device and advancer. The loading device 800 can similarly include a housing 802 and end effector repository 804. Further, the repository 804 can include a plurality of end effector lumens 806 that can each receive a modular surgical end effector 602. In the illustrated embodiment, however, the advancer 808 is much shorter, such that the end effector 602 is closer to the actuator 810 that controls the position of the advancer 808. Accordingly, when the actuator 810 is moved to a distal-most position the end effector 602 will be positioned at a proximal end of the deployment lumen (not shown).

FIGS. 9A-17 illustrate another embodiment of an end effector loading device 900 that includes separate advancer mechanisms for controlling movement of an end effector within the end effector repository and within the deployment lumen. The device 900 includes several components that are similar to the devices described above, including a housing 902, distal-facing portion 903, at least one mating element 904, deployment lumen 906, end effector repository 908, and slidable advancer 910. In addition, the device 900 couples with a surgical trocar, such as trocar 100 described above, in a similar manner as the device 300. The device 900, however, also includes a worm drive mechanism 914 that controls advancement of an end effector 916 through the deployment lumen 906.

Figure 11:
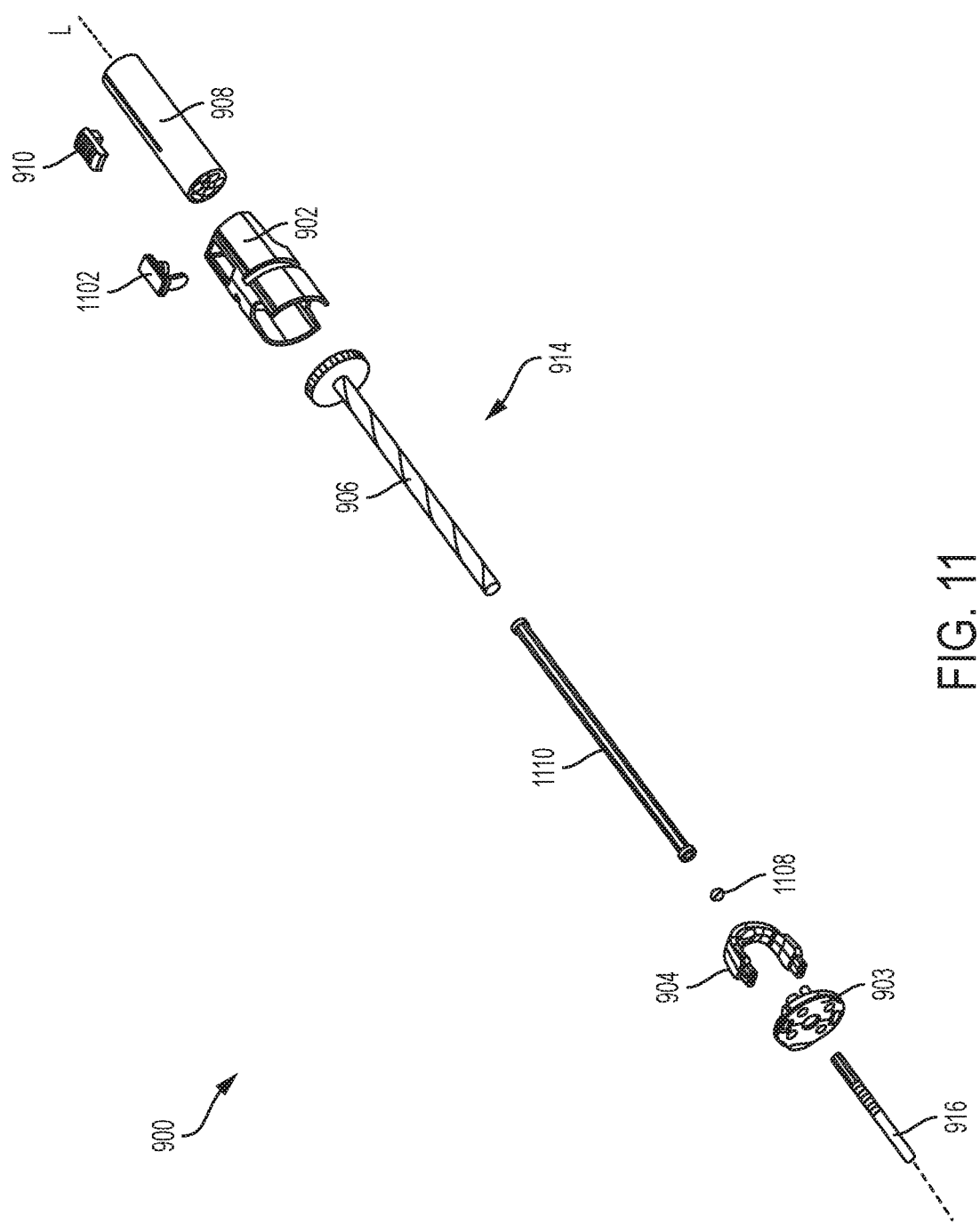
FIG. 11 is an exploded view of the device of FIG. 9A.

The exploded view of FIG. 11 illustrates the components of the device 900 in greater detail. The construction of the housing 902, 903, mating element 904, and end effector repository 908 are similar to the device 300 described above. In addition, the device 900 also includes a button 1102 for selectively blocking the passage of end effectors into the deployment lumen 906. Further, the advancer 910 is similar to the embodiment illustrated in FIG. 8 and described above. The worm drive mechanism 914 includes the deployment lumen 906, a translating end effector retainer 1108, and an end effector retainer guide 1110. The end effector retainer guide 1110 sits within the deployment lumen 906 and is rotationally fixed relative to the device 900, while the end effector retainer 1108 slides along the guide 1110 as the deployment lumen 906 is rotated. Moreover, female threads 1204 (see FIG. 12) can be formed on an inner sidewall of the deployment lumen 906 to guide movement of the end effector retainer 1108 as the deployment lumen is rotated.

Figure 12:
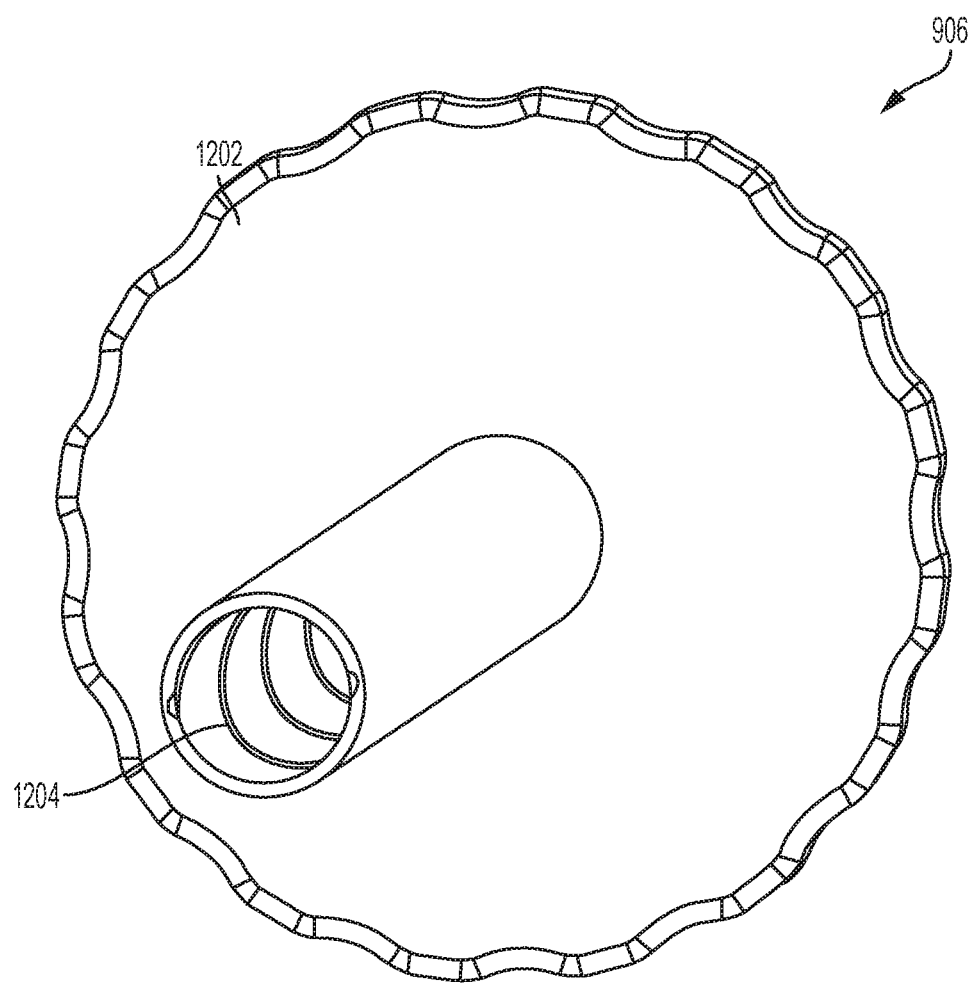
FIG. 12 is a perspective view of a worm tube of the device of FIG. 9A.

FIG. 12 illustrates the deployment lumen 906 in greater detail. The deployment lumen 906 of the device 900 can rotate freely with respect to the housing 902, and includes an enlarged flange 1202 to allow a user to grasp the deployment lumen and control its rotation. The flange 1202 can include features formed on an outer surface thereof to enhance a user's grip.

Figure 13A:
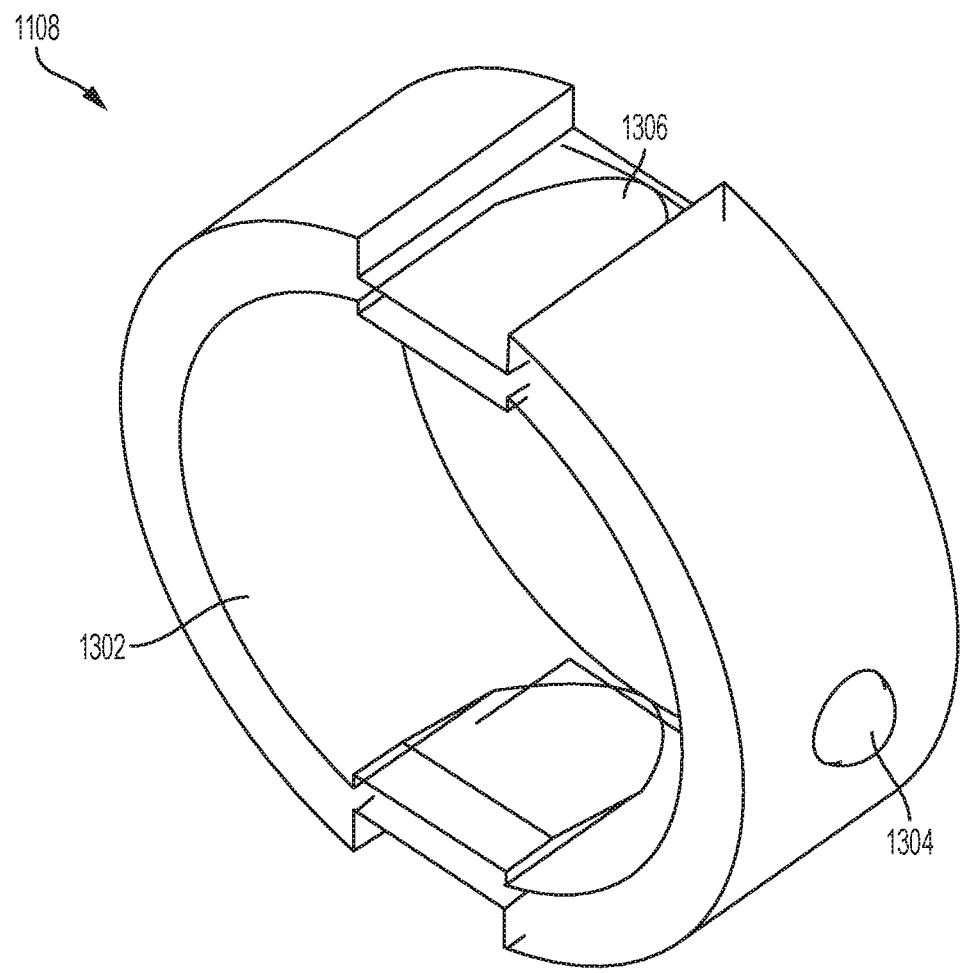
FIG. 13A is a perspective view of an end effector retainer of the device of FIG. 9A.
Figure 13B:
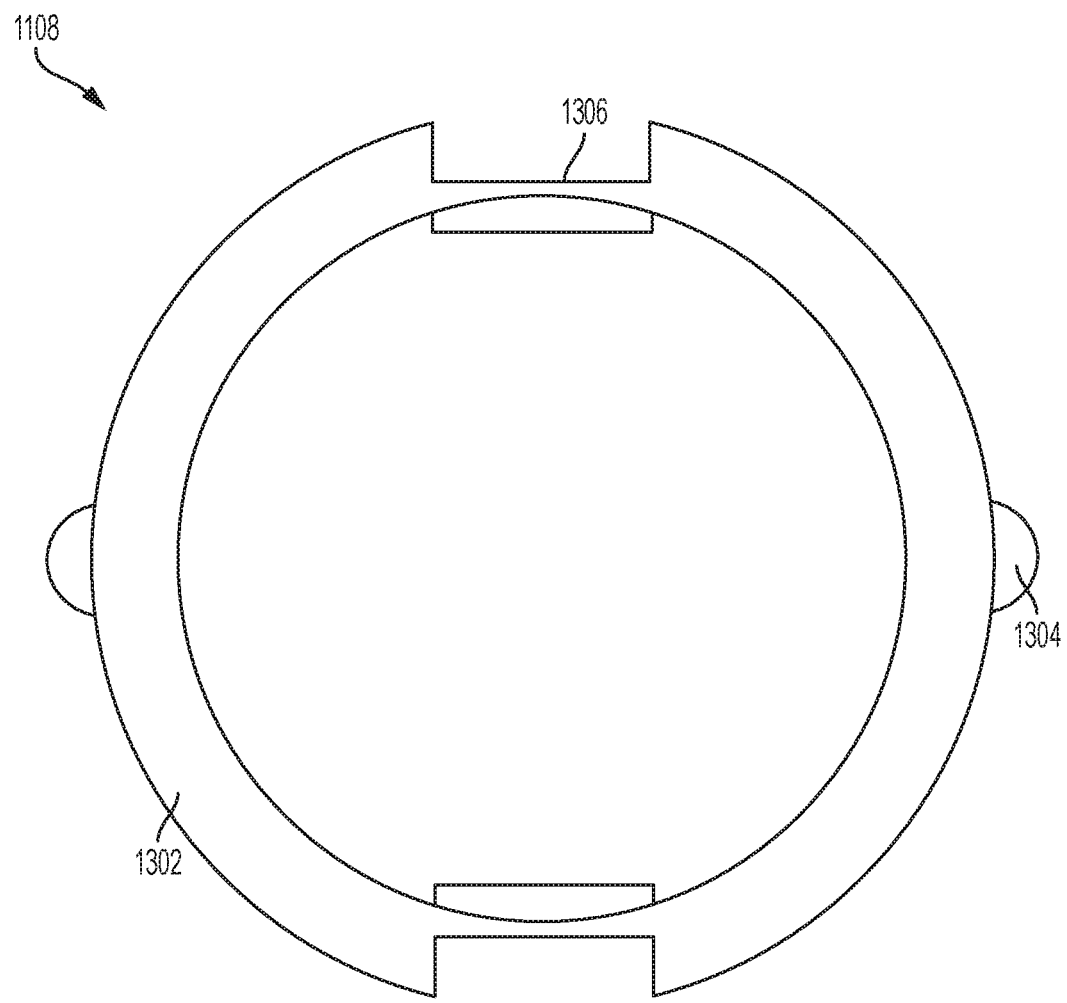
FIG. 13B is a front view of the end effector retainer of FIG. 13A.

FIGS. 13A and 13B illustrate the end effector guide 1108. The guide 1108 can be a generally ring-shaped component 1302 sized to slide within the deployment lumen and allow passage of an end effector through an inner lumen formed therein. The outer surface of the component 1302 can include one or more projections 1304 configured to be received by the female threads 1204 formed in the inner sidewalls of the deployment lumen 906, as well as one or more recesses 1306 configured to receive a portion of the end effector retainer guide 1110.

FIG. 14 illustrates the end effector retainer guide 1110 that can be rotationally fixed relative to the device 900 (e.g., fixed to the housing 902 at a proximal end thereof) and can guide the proximal/distal translation of the end effector retainer 1108 as the deployment lumen 906 is rotated. The guide 1110 can include a proximal retaining ring 1402 and a distal retaining ring 1404, as well as one or more longitudinally extending rails 1406. The rails 1406 can be fixed to the proximal and distal retaining rings 1402, 1404 and can be sized to be received within the one or more recesses 1306 formed in the end effector retainer 1108. Given that the guide 1110 cannot rotate relative to the housing 902, the interplay of the rails 1406 and the recesses 1306 can prevent the end effector retainer 1108 from rotating as well.

Figure 15:
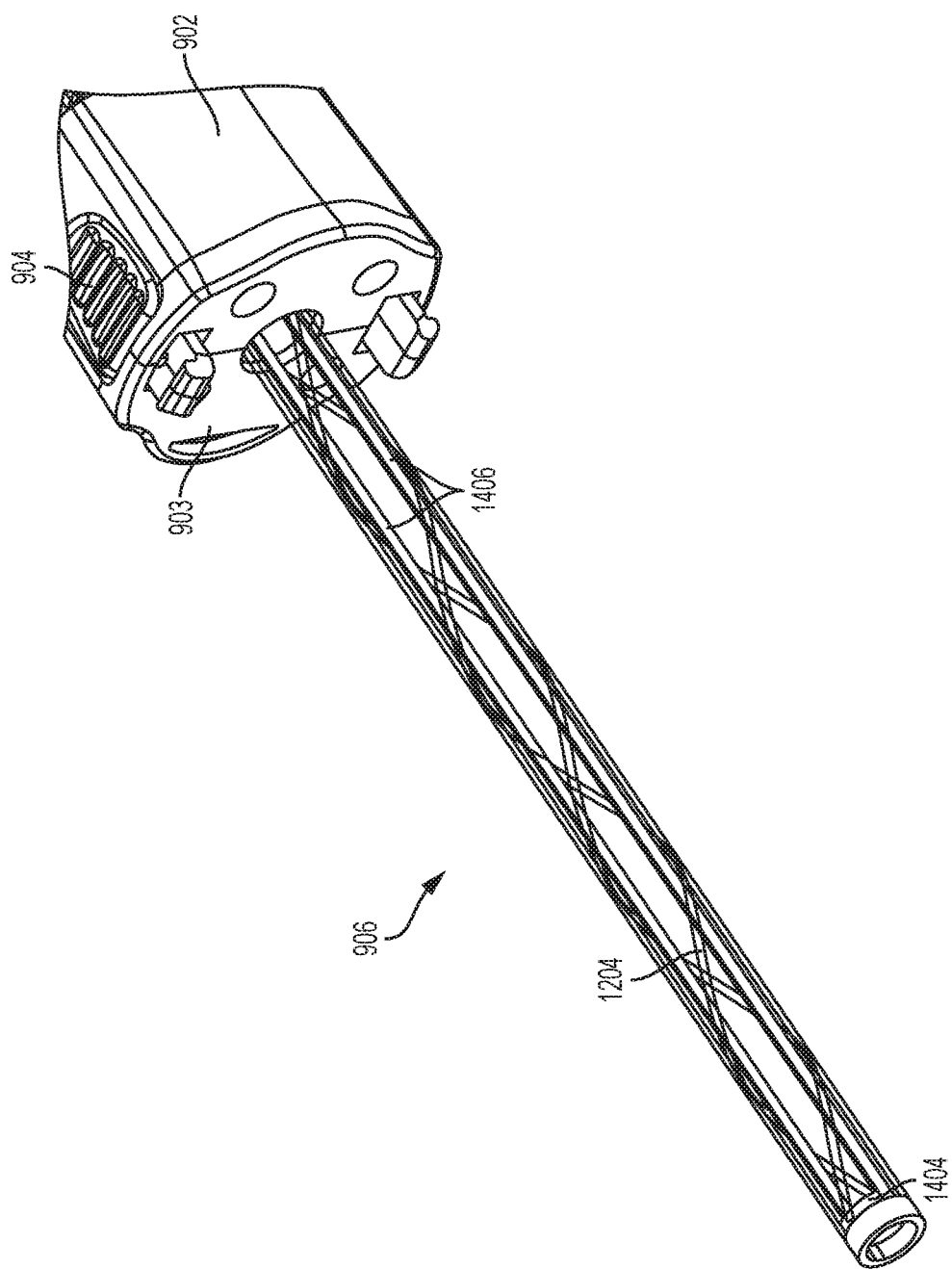
FIG. 15 is a partially-transparent perspective view of a distal portion of the device of FIG. 9A.

FIG. 15 illustrates the end effector retainer guide 1110 disposed within the deployment lumen 906. Visible in the figure is the distal retaining ring 1404 (the proximal retaining ring 1402 is not shown and can be affixed to the housing 902), longitudinally-extending rails 1406, and female threads 1204 formed on an inner sidewall of the deployment lumen 906. The end effector retainer 1108 can translate proximally and distally along the rails 1406 as the deployment lumen 906 is rotated because the projections 1304 will ride along the female threads 1204 formed in the deployment lumen sidewall while the rails prevent any rotation of the end effector retainer 1108.

Figure 16:
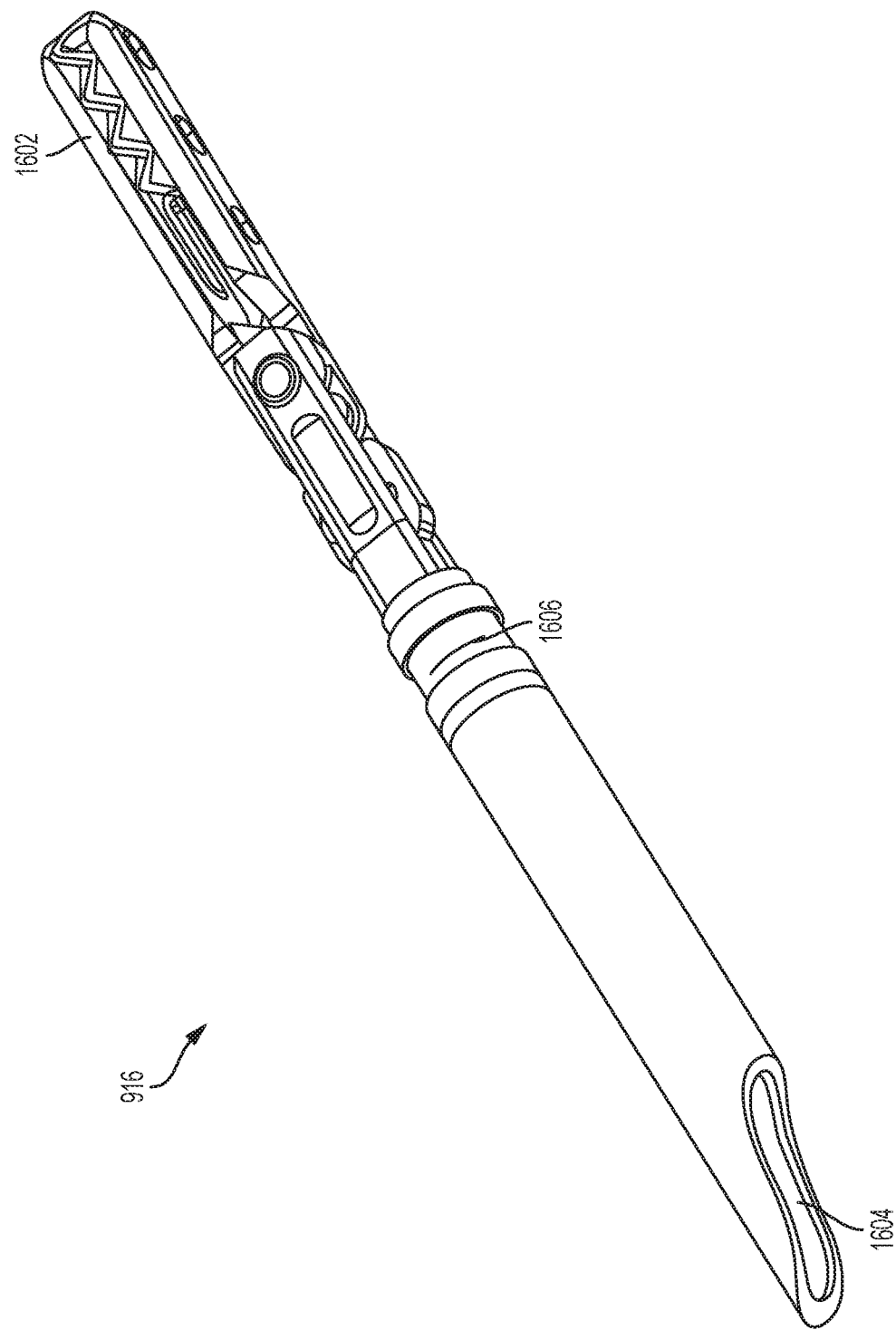
FIG. 16 is a perspective view of one embodiment of a surgical end effector.

FIG. 16 illustrates the end effector 916, sometimes referred to as an end effector assembly, in greater detail to show one embodiment of a mechanism for coupling the end effector to the end effector retainer 1108. The end effector 916 can include a distal portion 1602 configured to perform a particular task (e.g., opposed grasping jaws in the illustrated embodiment), as well as a socket 1604 formed at a proximal end thereof for receiving a distal end of a percutaneous surgical instrument shaft. In a middle portion of the end effector 916, one or more mating features 1606 can be formed that are configured to interface with the end effector retainer 1108. For example, in the illustrated embodiment a series of ridges define an annular-shaped depression around the end effector 916 that can receive the ring-shaped member 1302 of the end effector retainer 1108. The sizes of the mating features 1606 and end effector retainer 1108 can be controlled such that a desired interference fit is achieved that is sufficiently secure but also can be overcome when desired to either couple or decouple the end effector 916 from the end effector retainer 1108.

The illustrated end effector retainer 1108 is just one possible embodiment and a number of variations or alternatives can be employed. For example, the illustrated configuration can be reversed to provide an end effector mating feature 1606 having radially-outward-biased protrusions formed thereon that are configured to fit into recesses formed on an inner sidewall of the end effector retainer 1108. Alternatively, any of a variety of other latching mechanisms can be utilized to couple the end effector 916 to the end effector retainer 1108. Certain embodiments of an end effector retainer 1108 can allow for rotation of the end effector 916 when coupled (and permit coupling of the end effector in any rotational orientation), such as the illustrated annular depression, or can prevent such rotation (e.g., if separate hemispherical recesses were employed in place of the annular recess).

Figure 17:
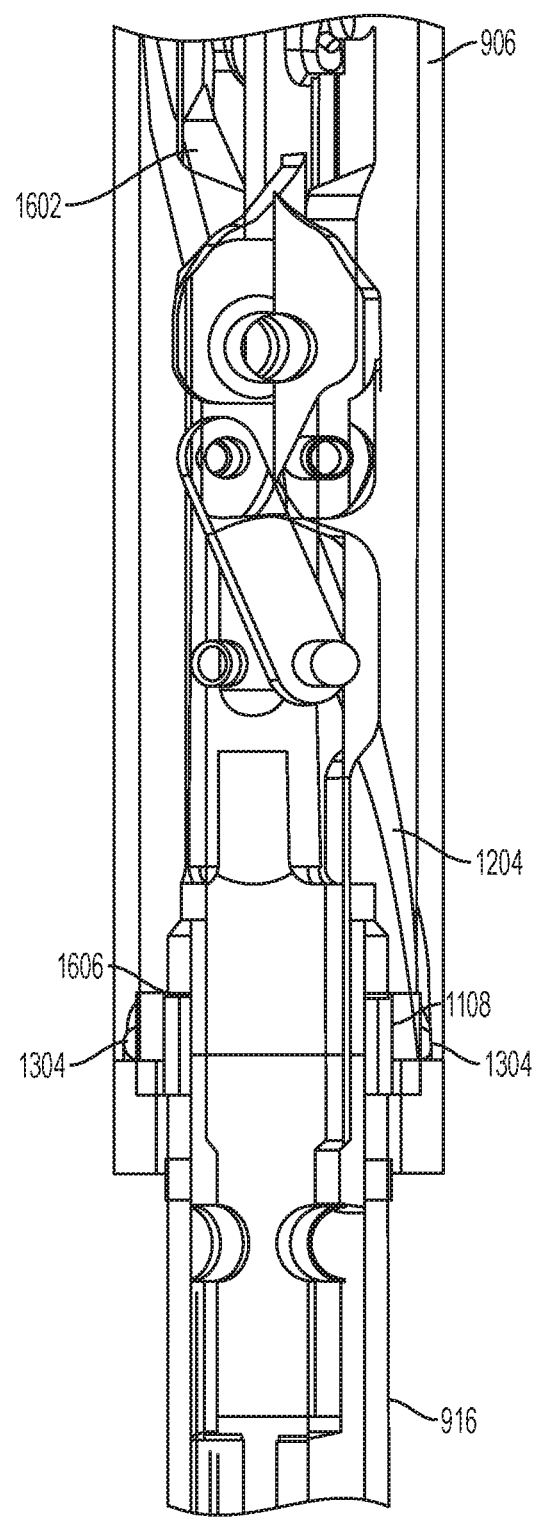
FIG. 17 is a side cross-sectional view of a distal portion of the device of FIG. 9A and the end effector of FIG. 16 taken along the line B-B.

FIG. 17 illustrates the interplay of the various components of the worm drive mechanism 914 in greater detail. In the cross-sectional view of the figure, the end effector retainer 1108 can be seen seated within the annular depression 1606 formed in the central portion of the end effector 916. This selectively locks the end effector 916 to the end effector retainer 1108. Moreover, the projections 1304 extending from an outer surface of the end effector retainer 1108 can be seen riding within the female threads 1204 formed on the inner sidewall of the deployment lumen 906. As a result of these interactions, along with the interaction between the end effector retainer 1108 and guide 1110, the end effector 916 can be carried along the length of the deployment lumen 906 by a user rotating the lumen via the flange 1202.

When the end effector 916 reaches a distal end of the deployment lumen 906, a percutaneous surgical instrument shaft can be inserted into the exposed socket 1604 at the proximal end of the end effector to couple the end effector to the instrument. The instrument can then be withdrawn and the force exerted on the end effector can overcome the interference fit between the end effector retainer 1108 and the end effector mating feature 1606, thereby freeing the end effector from the loading device 900. This procedure can be reversed to return the end effector 916 to the loading device 900 after the procedure is complete, or when one end effector needs to be exchanged for another.

In addition to providing the ability to manage and selectively deploy any of a plurality of modular end effectors from a single device, the devices and methods described herein also provide for easier alignment of an end effector with a percutaneous surgical instrument that is to be coupled thereto, as well as improved feedback regarding the status of such coupling. These features can be beneficial because they allow a surgeon or other user to perform an end effector coupling or decoupling in vivo with less difficulty.

Figure 18C:
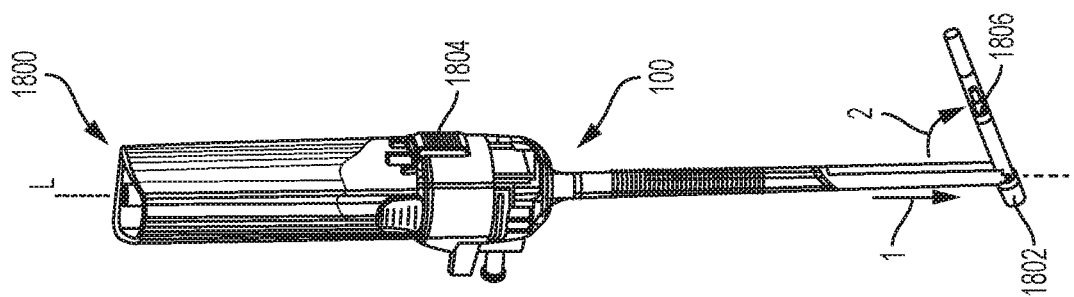
FIG. 18C is a perspective view of the device of FIG. 18A with the advancer in the second, deployed position.
Figure 18B:
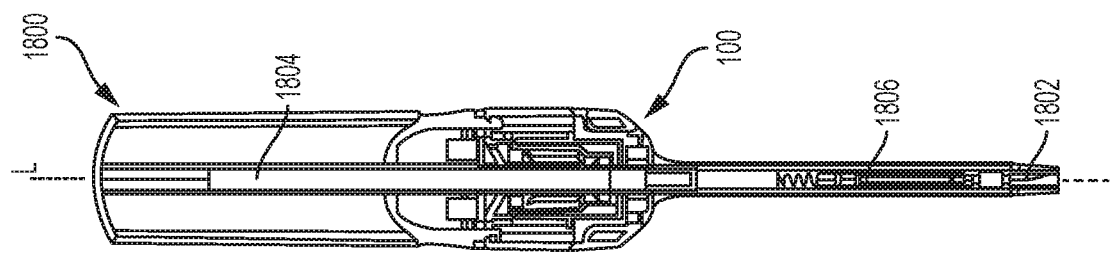
FIG. 18B is a side cross-sectional view of the device of FIG. 18A taken along the line C-C.
Figure 18A:
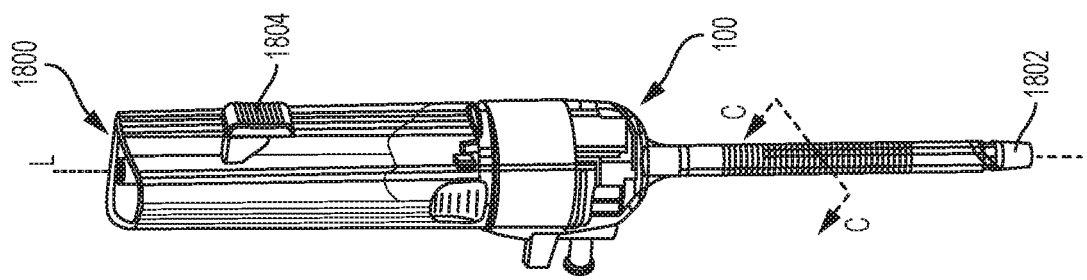
FIG. 18A is a perspective view of one embodiment of a surgical end effector loading device assembly having an advancer disposed at a location between a first, retracted position and a second, deployed position.
Figure 19:
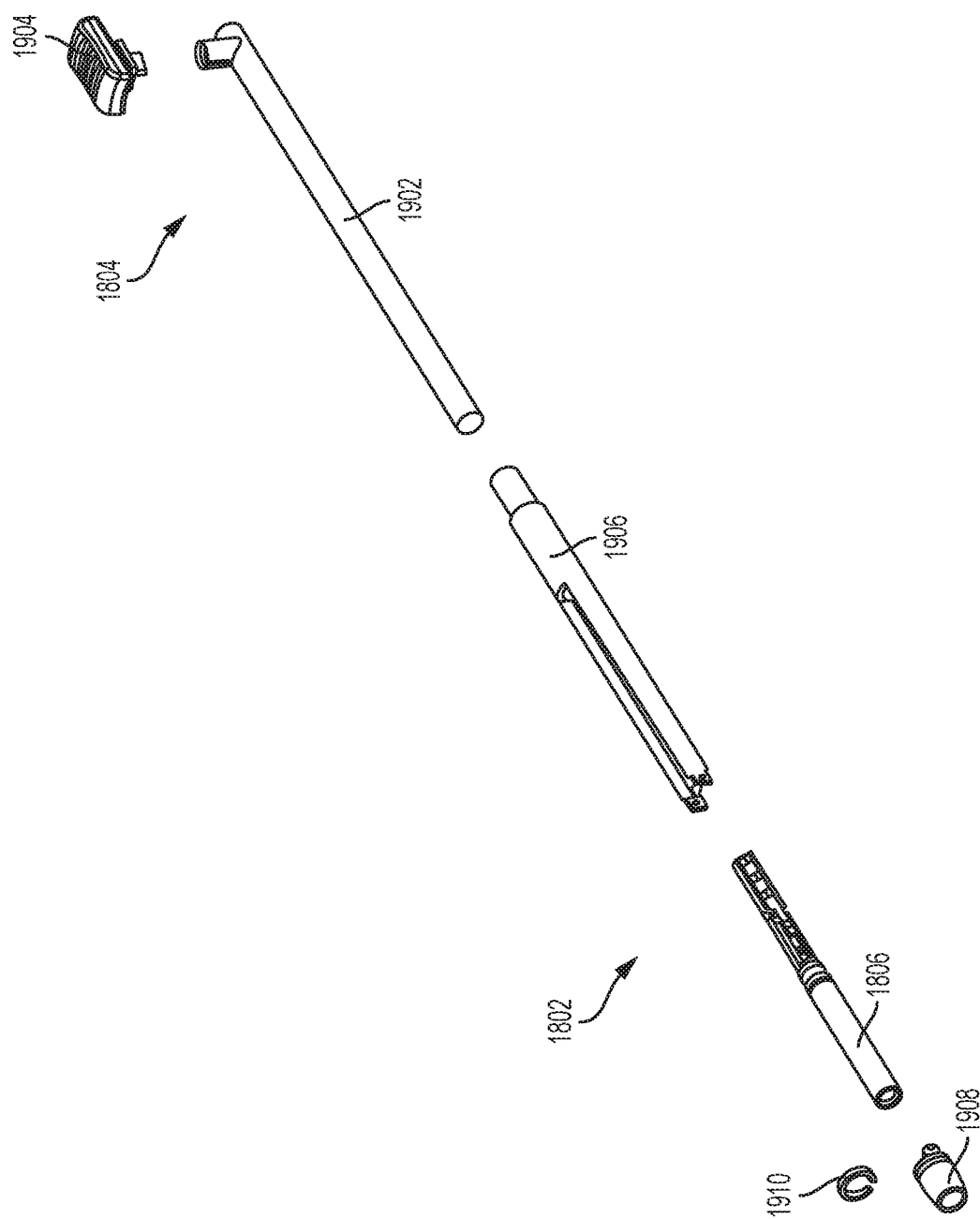
FIG. 19 is an exploded view of the advancer, end effector retainer, and surgical end effector of FIG. 18A.

Easier alignment of end effectors and surgical instruments can be accomplished in some embodiments by utilizing an end effector retainer that permits pivoting an end effector relative to a loading device once the end effector has been advanced through the working channel of a surgical trocar. FIGS. 18A-18C illustrate one embodiment of an end effector loading device 1800 with this type of end effector retainer 1802. In the perspective and cross-sectional views of FIGS. 18A and 18B, respectively, an advancer 1804 is positioned at an intermediate point between its proximal-most and distal-most positions, and the end effector retainer 1802 is accordingly partially extended from a distal end of the trocar 100. As the advancer 1804 continues to be moved distally relative to the device 1800, the end effector retainer 1802 will extend fully from the distal end of the trocar 100, as shown in FIG. 18C (indicated by arrow 1). Once the end effector retainer 1802 is fully extended, a portion thereof can pivot relative to a longitudinal axis L of the device 1800 to change the orientation of the end effector 1806 attached to the retainer 1802 (indicated by arrow 2). This change in orientation of the end effector 1806 can make it easier to align a percutaneously-inserted surgical instrument for coupling to the end effector. The pivoting motion can be controlled in a number of ways. For example, a control cable can be routed down the end effector retainer 1802 from a proximal end of the device and utilized to control pivoting motion. In other embodiments, the pivoting motion can be made part of the distal advancement of the end effector retainer 1802 using a cam mechanism, such that the final portion of distal travel of the advancer 1804 causes the pivoting motion. Such a configuration can have the advantage of minimizing complexity and ensuring that end effector 1806 is sufficiently advanced out of the distal end of the trocar 100 before beginning the pivoting motion. Regardless of configuration utilized, any desired amount of pivoting can be provided. In embodiments utilizing a cam mechanism, a maximum amount of pivoting can be, in some cases, about 100°.

FIGS. 19-22 illustrate the end effector retainer 1802 in more detail. As noted above, the end effector retainer 1802 can be disposed at a distal end of a plunger component 1902 of the advancer 1804 and can be configured to selectively couple to an end effector 1806. The end effector retainer can include a housing 1906, as well as a pivoting end cap 1908 and retention clip 1910. The illustrated end effector retainer 1802 can ease the process of aligning an end effector with a percutaneously-inserted surgical instrument by allowing the end effector to pivot relative to the retainer, in contrast to, for example, the end effector retainer 1108 that requires an instrument to align with a longitudinal axis L of the loading device 900.

Figure 20:
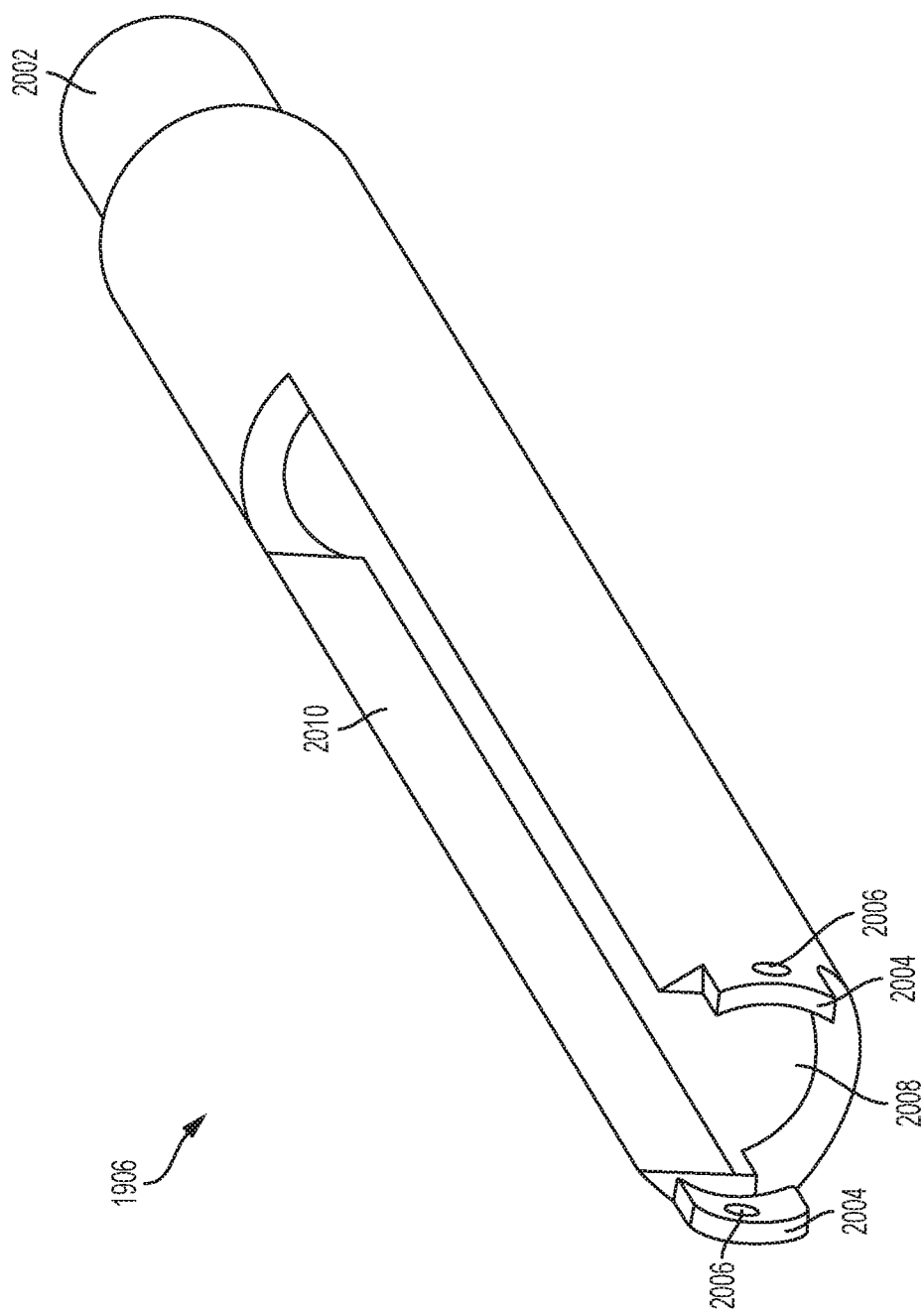
FIG. 20 is a perspective view of an end effector retainer housing of the device of FIG. 18A.

FIG. 20 illustrates the end effector retainer housing 1906 in greater detail. The housing 1906 can include a proximal end 2002 configured to be coupled to a distal end of the plunger component 1902 of the advancer 1804. A distal end of the housing 1906 can include opposed arms 2004 having recesses 2006 formed therein that are configured to couple with pivot pins 2102 (see FIG. 21) of the pivoting end cap 1908. The housing 1906 can have a lumen 2008 formed therein and can include a cut-out 2010 from a portion of a sidewall thereof. The lumen 2008 can be configured to receive an end effector 1806 and the sidewall cut-out 2010 can be sized to allow the end effector 1806 to pivot away from, or into, the housing 1906 when attached to the pivoting end cap (see FIG. 18C).

Figure 21:
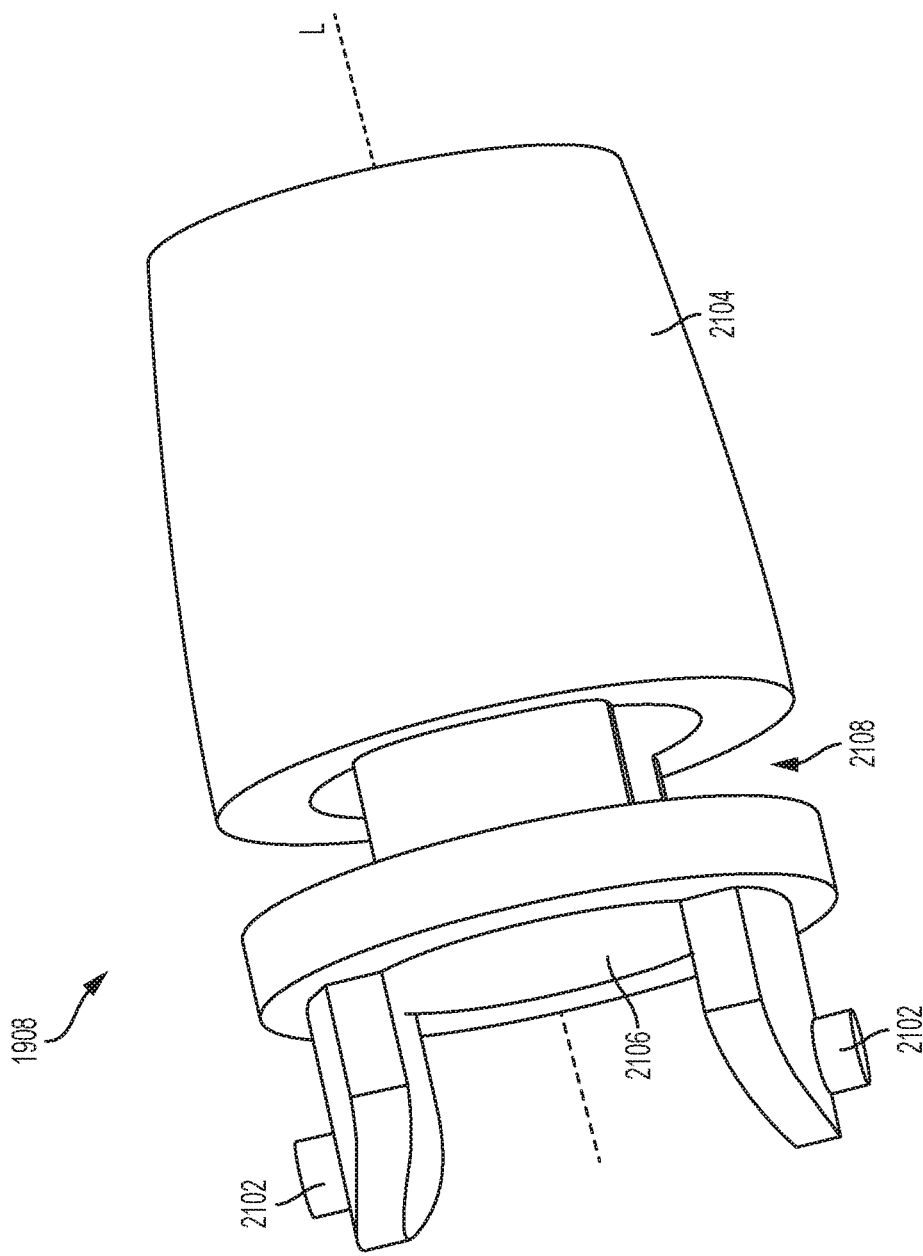
FIG. 21 is a perspective view of an end effector retainer pivoting end cap of the device of FIG. 18A.

The pivoting end cap 1908 can include, as mentioned above, a proximal end having opposed pivot pins 2102 configured to be received within recesses formed in a distal end of the end effector retainer housing 1906. As shown in FIG. 21, the pivoting end cap 1908 can have a generally cylindrical shape having an inner lumen 2106 formed therein for receiving an end effector 1806. A distal portion 2104 can include a sidewall cut-out 2108 sized to receive the retention clip 1910.

Figure 22:
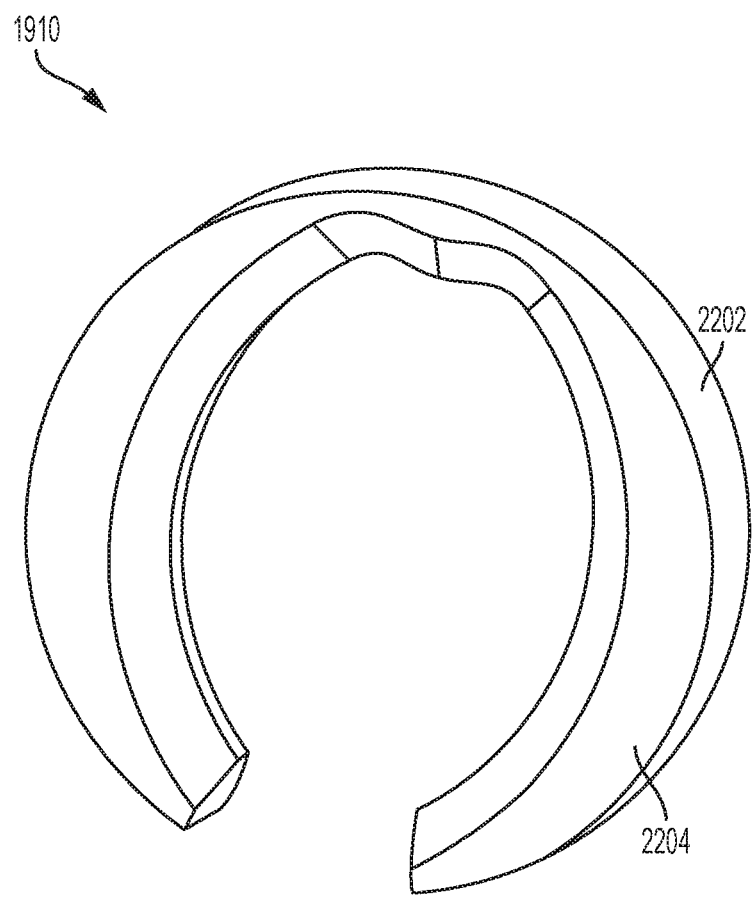
FIG. 22 is a perspective view of an end effector retainer retention clip of the device of FIG. 18A.

The retention clip 1910, as shown in FIG. 22, can be a resilient U-shaped component, such as a snap ring or spring clip. The retention clip 1910 can be configured to be received within the sidewall cut-out 2108 formed in the pivoting end cap 1908 such that it resiliently extends into the inner lumen 2106 of the pivoting end cap. The retention clip 1910 can have a variety of shapes, sizes, and rigidities, and in some embodiments can include a two-color body arranged to provide a visual indication of end effector coupling to a surgeon or other user, as described in more detail below. In one embodiment, for example, an outer circumference 2202 of the retention clip 1910 can have a different color from an inner portion 2204 thereof.

FIGS. 23A-24B illustrate one exemplary embodiment of coupling an end effector 1806 with the end effector retainer 1802. In FIGS. 23A and 23B, the end effector 1806 is aligned with, but a distance away from, the pivoting end cap 1908 of the end effector retainer 1802. As shown best in the side view of FIG. 23B, before the end effector 1806 is inserted into the pivoting end cap 1908, the resilient retention clip 1910 extends into the inner lumen 2106 of the pivoting end cap. To couple the end effector 1806 to the end effector retainer 1802, the end effector can be advanced into the configuration shown in FIGS. 24A and 24B. In this configuration, the insertion of the end effector 1806 into the lumen 2106 of the pivoting end cap 1908 can press the retention clip 1910 radially outward relative to a longitudinal axis L of the end cap. The biasing force of the retention clip 1910 can grasp the end effector 1806 and prevent it from falling away from the end effector retainer 1802. Further, in some embodiments the end effector 1806 can be inserted such that a recess or other feature, such as the annular depression 1606 described above, aligns with the retention clip 1910. Seating the retention clip 1910 in the depression 1606 can increase the strength of the coupling between the end effector 1806 and the retainer 1802.

In addition, the use of a multi-colored retention clip 1910 can provide a visual indication to a surgeon or other user when an end effector is sufficiently inserted into the end effector retainer 1802. For example, in the configuration of FIG. 23A, the retention clip 1910 is seated such that only the outer circumference surface 2202 is visible. However, in the configuration of FIG. 24A, wherein the end effector 1806 is grasped by the retention clip 1910, the different-colored inner portion 2204 is visible. Seeing this different-colored surface can serve as an indication that end effector 1806 is coupled to the end effector retainer 1802 and can be, for example, safely released from the distal end of a percutaneously-inserted surgical instrument.

Figure 25B:
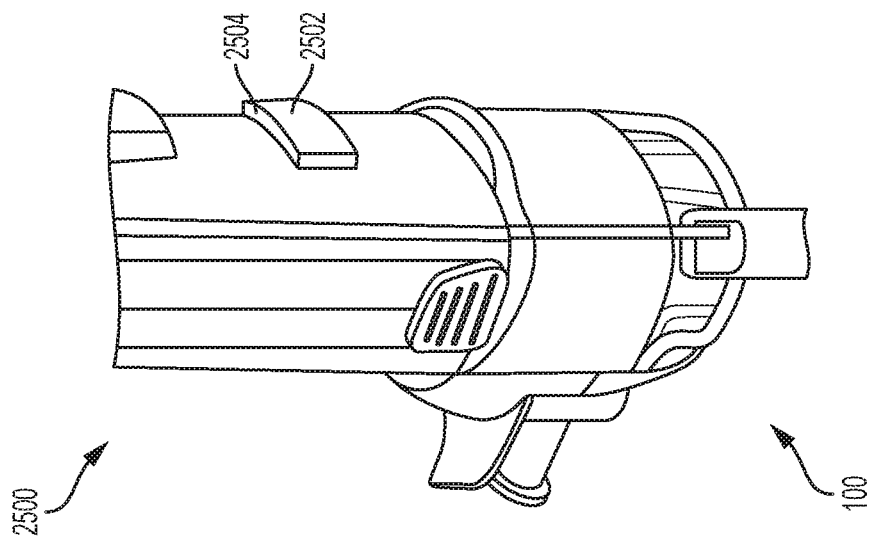
FIG. 25B is a perspective view of the assembly of FIG. 25A with the coupling indicator in a second position.
Figure 25A:
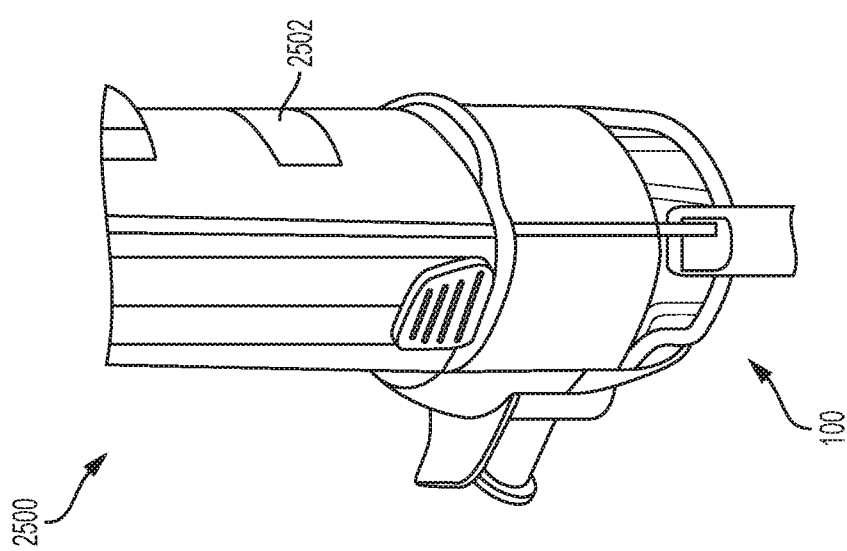
FIG. 25A is a perspective view of one embodiment of an assembly including a surgical end effector loading device having a coupling indicator in a first position.

In some embodiments, it can be desirable to provide an indication regarding the status of coupling between an end effector and a loading device at a location more easily visible by a user. In the embodiment of FIGS. 25A and 25B, for example, a loading device 2500 can include a button 2502 positioned along a proximal portion of the device (e.g., the device housing) to provide such an indication. The button 2500 can, for example, be connected to an end effector retainer, such as the retainer 1802 described above, via a mechanical linkage such that the button is pressed outward against a biasing force when an end effector is coupled to the retainer (as shown in FIG. 25B). Similar to the dual-color retention clip 1910 described above, the button 2502 can include a portion 2504 having a different color that is only visible when the button is urged outward against the biasing force. Accordingly, the position and visible color of the button can provide an easily observable indication of the coupling status of a retainer and an end effector.

Figure 26:
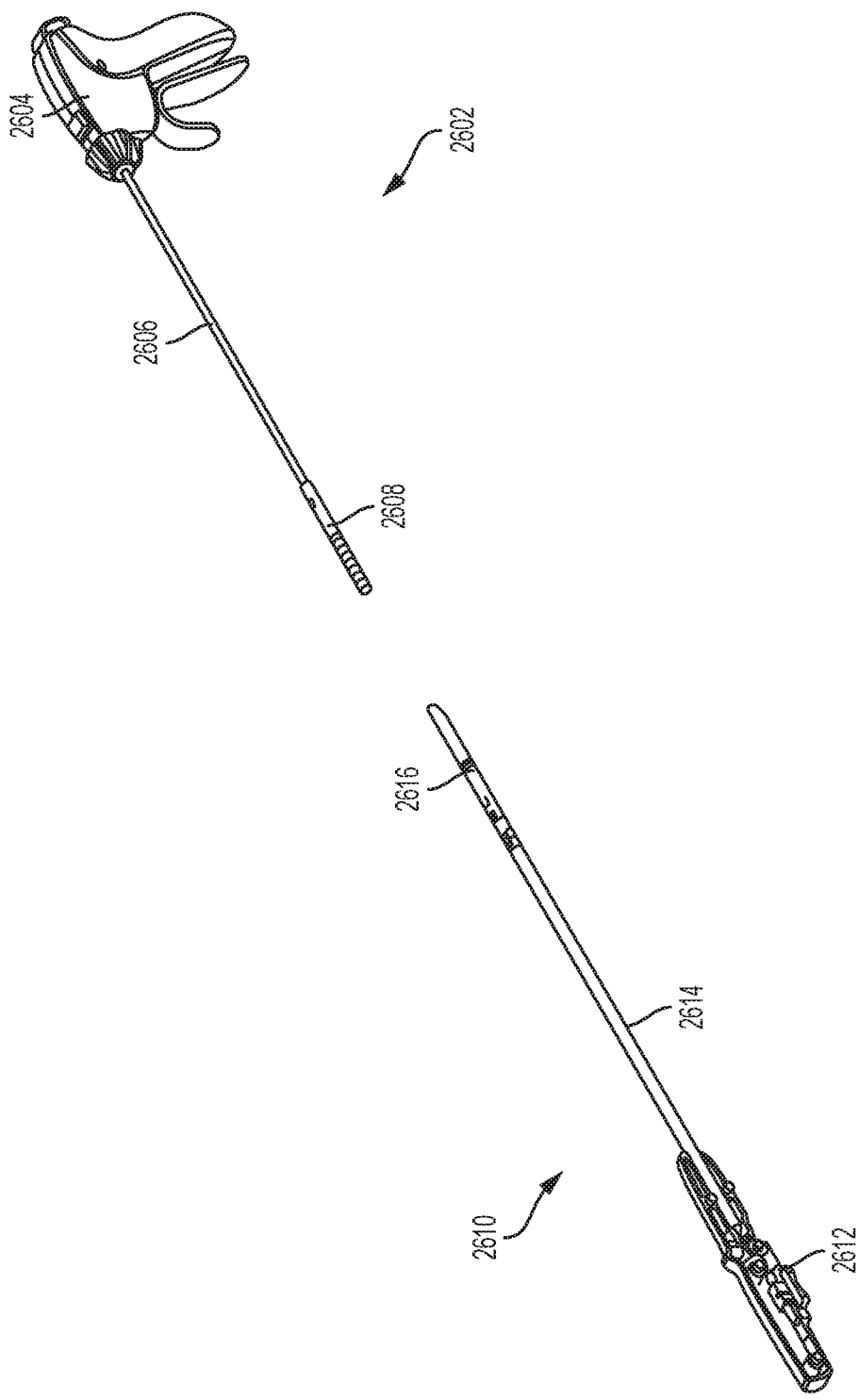
FIG. 26 is a perspective view of one embodiment of an assembly including a percutaneous surgical instrument and an end effector loading device with a portion of a handle of the end effector loading device removed for illustrative purposes.
Figure 27A:
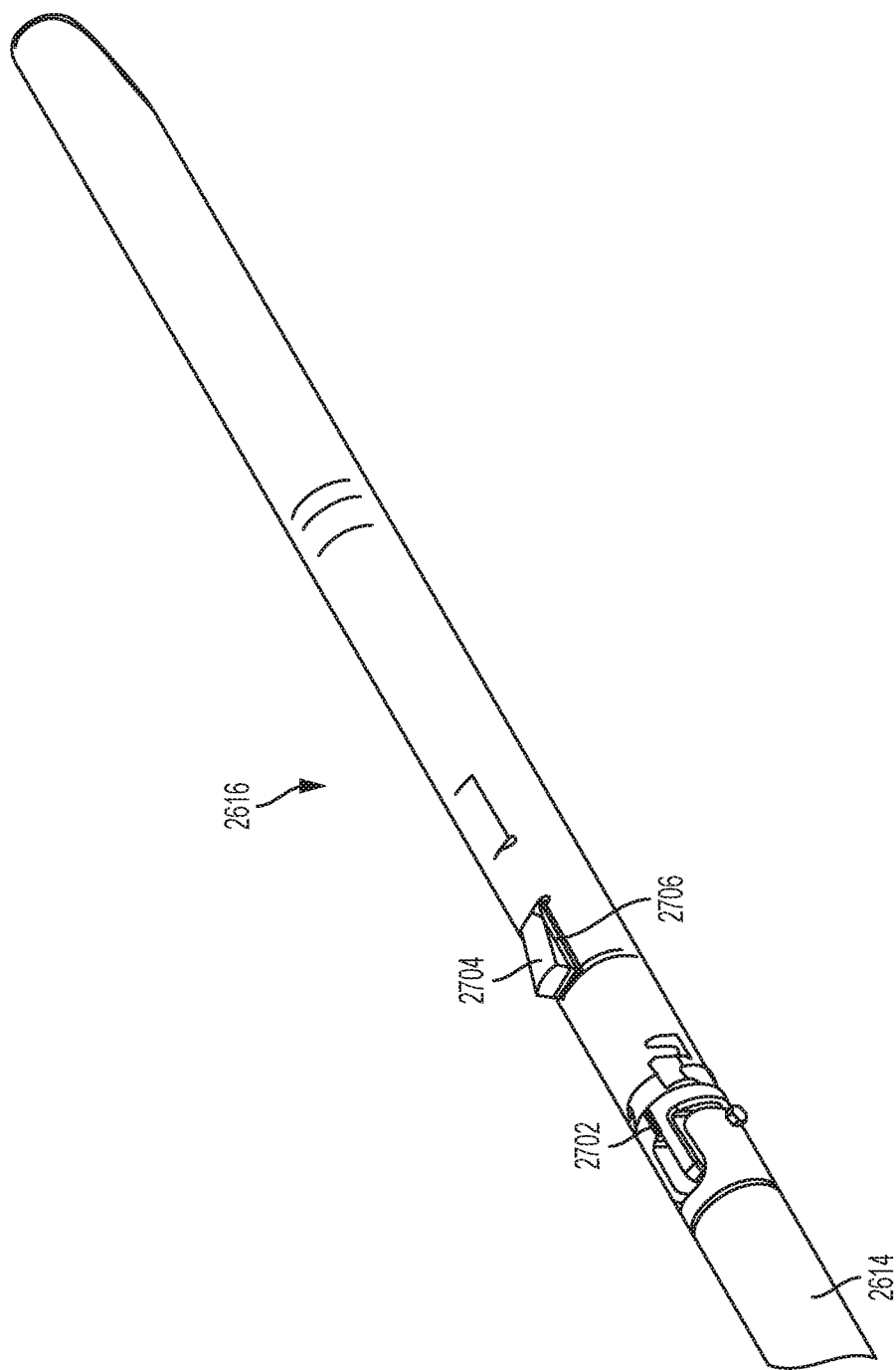
FIG. 27A is a detail view of a portion of the end effector loading device of FIG. 26.
Figure 27B:
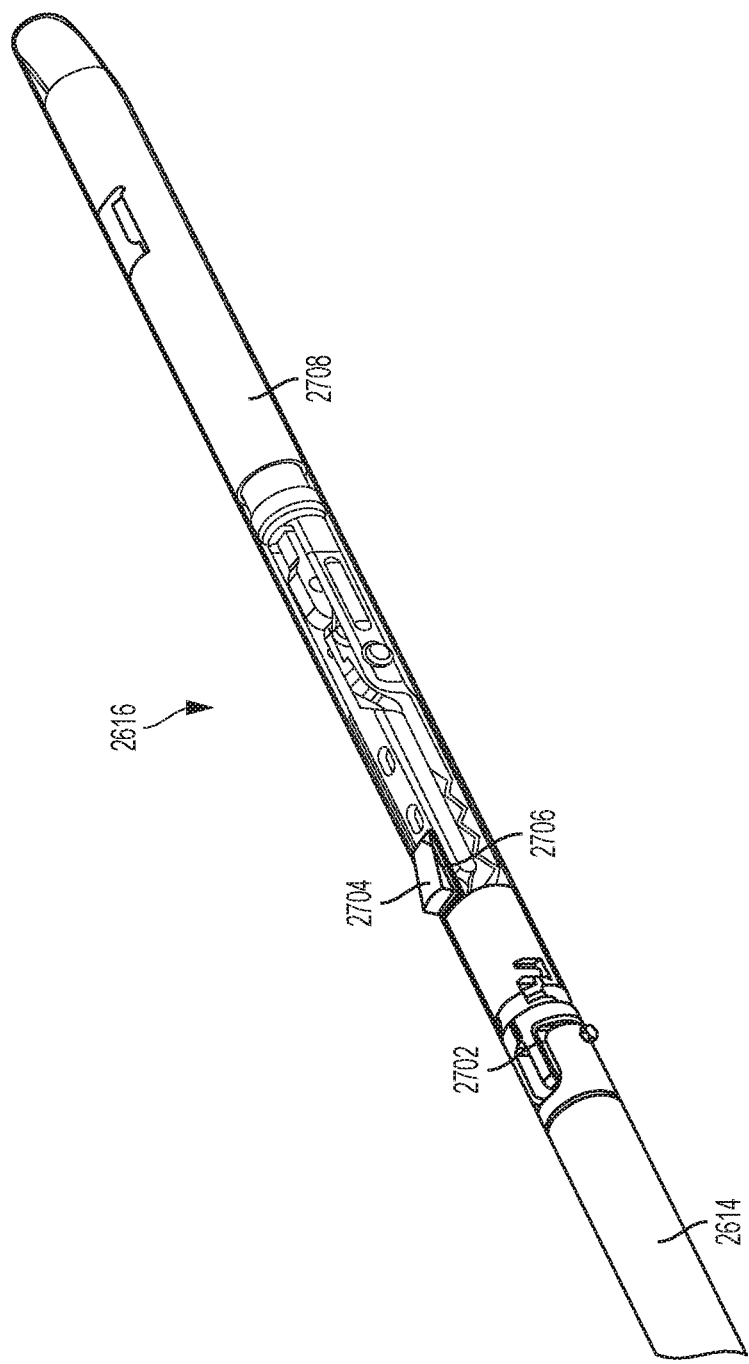
FIG. 27B is a partially-transparent view of the portion of the device of FIG. 27A.

FIGS. 26-30B illustrate still another embodiment of a coupling status indicator that can be employed on both the end effector (to indicate coupling status of an end effector and a percutaneous surgical instrument) and a loading device (to indicate coupling status of an end effector and the loading device). FIG. 26 illustrates the basic components of a percutaneous surgical instrument 2602 and a more traditional loading device 2610, though the same principles can be applied to the multi-head loading devices described herein. The percutaneous surgical instrument 2602 includes an actuator 2604 (e.g., a handle in the case of a hand-operated instrument), a shaft 2606 configured to percutaneous insertion through tissue, and an end effector 2608. The loading device 2610 similarly includes an actuator 2612 and shaft 2614, as well as an end effector retainer 2616.

FIGS. 27A-28B illustrate the end effector retainer 2616 of the loading device 2610 in greater detail. As shown in the figures, the end effector retainer 2616 can be coupled to the shaft 2614 by an articulating joint 2702 and the retainer can house a modular end effector 2708. The end effector retainer 2616 can also include a pivoting coupling indicator 2704 that extends upward from the outer surface of the end effector retainer 2616 when an end effector 2708 is coupled to the retainer. As with the retention clip 1910 and button 2502 described above, the indicator 2704 can include a portion 2706 that has a different color and is only visible when the indicator is popped up above the surface of the retainer 2616. The indicator 2704 can thereby provide the same type of easily observable indication of coupling status as the retention clip 1910 and button 2502 described above.

Figure 28A:
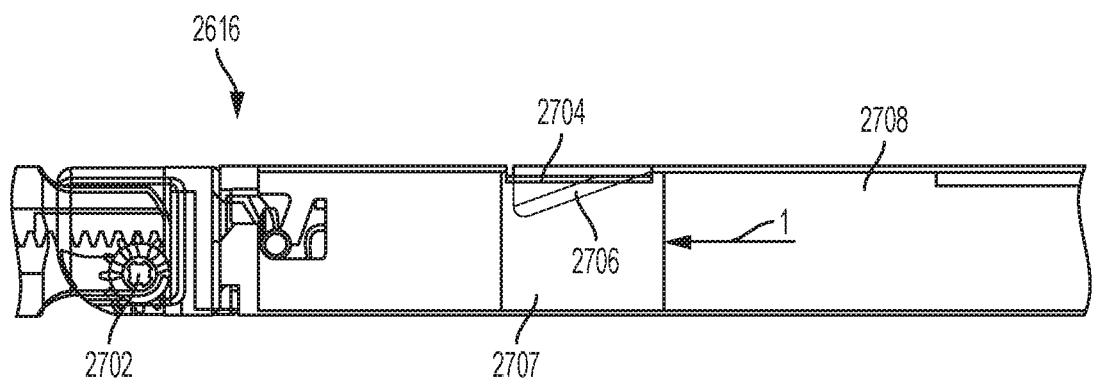
FIG. 28A is a partially-transparent view of a portion of the end effector loading device of FIG. 26 prior to end effector coupling.
Figure 28B:
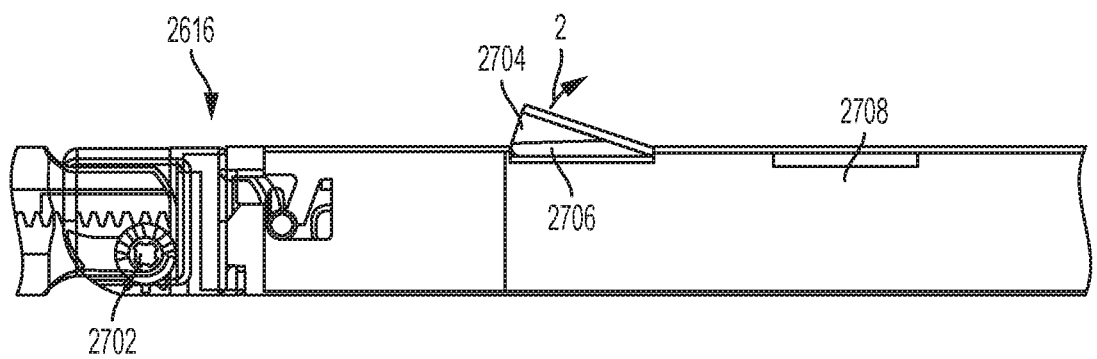
FIG. 28B is a partially-transparent view of the portion of the device of FIG. 28A after end effector coupling.
Figure 29A:
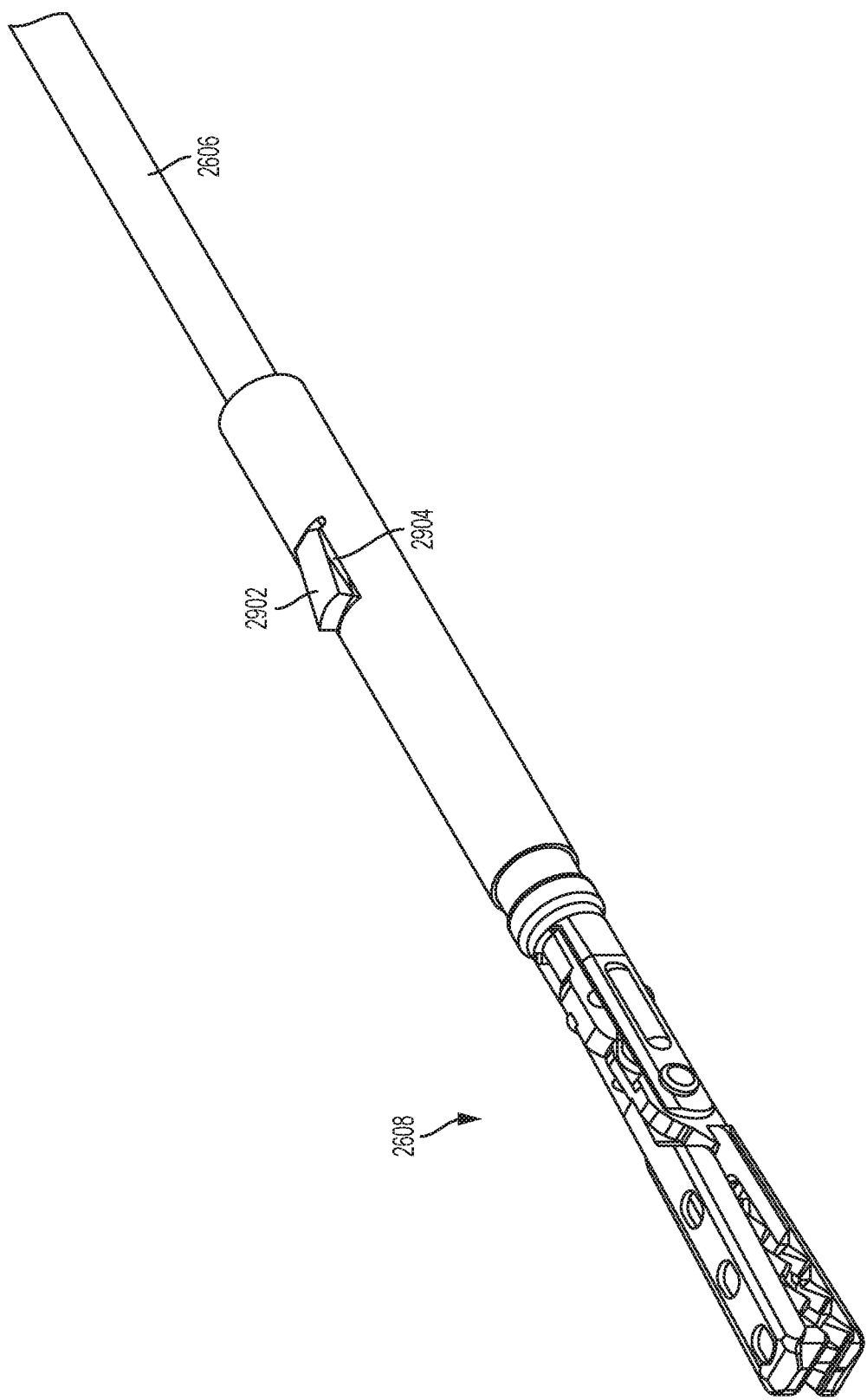
FIG. 29A is a detail view of a portion of the percutaneous surgical instrument of FIG. 26.

FIGS. 28A and 28B in particular illustrate the actuation of the indicator 2704 as an end effector 2708 is inserted into the end effector retainer 2616. In FIG. 28A, for example, the indicator 2704 remains in a retracted configuration as the end effector 2708 is initially inserted into the retainer 2616 (shown by arrow 1). This can be because the indicator 2704 is biased toward the configuration illustrated in FIG. 28A, i.e., biased toward an inner lumen 2707 of the end effector retainer 2616. As the end effector 2708 is fully inserted into the inner lumen 2707, however, it can urge the indicator 2704 outward into the configuration shown in FIG. 28B. In this extended configuration the differently-colored portion 2706 can be visible to a user (shown by arrow 2), thereby providing feedback of successfully coupling between the end effector 2708 and the end effector retainer 2616.

This same type of indicator can be utilized on the end effector itself to provide an indication of coupling status with a percutaneous surgical instrument 2602. As shown in FIGS. 29A-30B, for example, the end effector 2608 that couples to the shaft 2606 of the instrument 2602 can include a pivoting coupling indicator 2902 similar to the indicator 2704 described above. That is, the indicator 2704 can be configured to move between a retracted configuration when the instrument 2602 is not coupled (or only partially coupled) to the end effector 2608, and an extended configuration when the instrument and end effector are fully coupled. Further, the indicator 2902 can include a differently-colored portion 2904 that is only visible in the extended configuration to provide an easily observable indication of coupling status.

FIG. 29B illustrates one exemplary mechanism for coupling the end effector 2608 to the remainder of the instrument 2602. As noted above, the end effector 2608 can include a socket 2906 formed at a proximal end thereof that can receive a distal end of the instrument shaft 2606. The shaft 2606 can include multiple concentric shafts housed therein, including an inner shaft 2908 and an intermediate shaft 2910. With the inner shaft 2908 retracted proximally, opposed arms of the intermediate shaft 2910 can deflect inward to pass through a collar 2912 of the end effector 2608. The inner shaft 2908 can then be advanced distally to prevent the arms of the intermediate shaft 2910 from deflecting inward, thereby locking the end effector 2608 to the instrument. Further relative motion between the various shafts 2606, 2908, and 2910 can produce movement of, e.g., jaws or other implements of the end effector 2608. Further information on exemplary coupling mechanisms for an end effector and percutaneous instrument can be found in U.S. Patent Publication No. 2011/0087267 to Spivey et al., entitled "Method for Exchanging End Effectors In Vivo," which is hereby incorporated by reference.

Figure 30A:
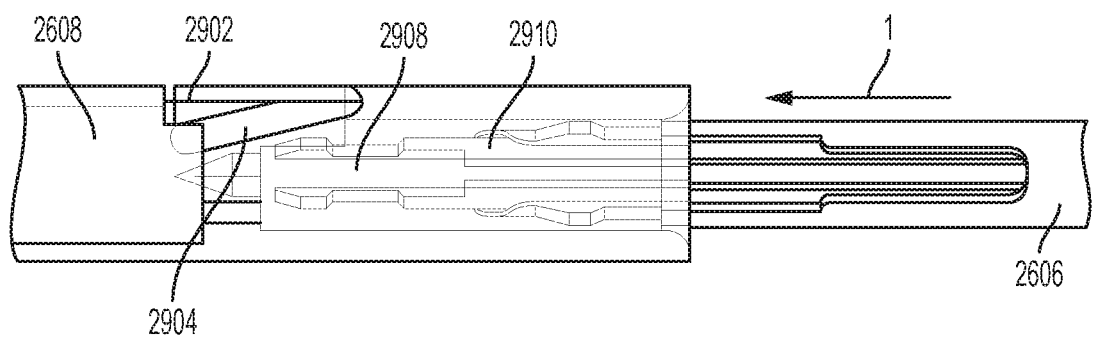
FIG. 30A is a partially-transparent view of a portion of the percutaneous surgical instrument of FIG. 26 prior to end effector coupling.
Figure 30B:
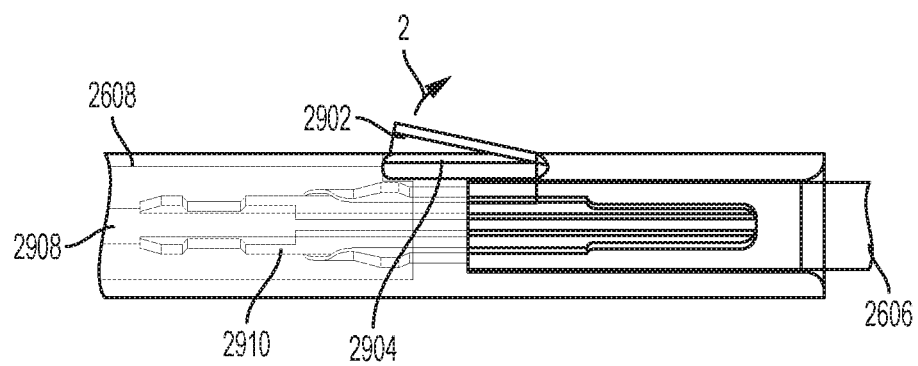
FIG. 30B is a partially-transparent view of the portion of the device of FIG. 30A after end effector coupling.

FIGS. 30A and 30B illustrate the operation of the indicator 2902, which is similar to the operation of the indicator 2704 shown in FIGS. 28A and 28B and described above. In particular, the indicator 2902 of the end effector 2608 can be biased inward toward an inner lumen of the socket 2906 such that it sits in the position shown in FIG. 30A. As the shafts 2606, 2908, and 2910 are inserted into the socket 2906 (as shown by the arrow 1 in FIG. 30A), they can contact the indicator 2902 and urge it into the extended configuration shown in FIG. 30B. In such a configuration, the differently-colored portion 2904 can be visible to a user, thereby providing feedback that the end effector 2608 has been coupled to the instrument 2602.

While the various embodiments described above may have only subset of the features described herein, the various components and functionalities described can be combined in a variety of manners, all of which are considered within the scope of the present invention. For example, a loading device could include both the translating advancer and worm drive mechanism of the device 900, as well as the pivoting end effector retainer of the device 1800.

The devices described herein can be utilized in a variety of surgical procedures. In general, a method of using the devices described herein can include coupling a loading device with a surgical trocar such that a deployment lumen formed in the loading device coaxially aligns with a working channel of the surgical trocar and complementary mating features on the loading device and the surgical trocar restrict relative motion therebetween. Coupling the loading device to the trocar can occur after loading one or more surgical end effectors into the loading device, or the loading device can come pre-installed with one or more surgical end effectors, or the loading device can be inserted without an end effector in anticipation of receiving one from a percutaneously-inserted surgical instrument (e.g., at the conclusion of a procedure). As mentioned above, the coupling of the loading device and the trocar can make use of pre-existing mating features formed on or in the trocar for attachment of other accessories, such as an obturator.

Methods of using the devices described herein can further include actuating an end effector repository of the loading device to align one of a plurality of end effector lumens formed therein with the deployment lumen of the loading device. Actuating the end effector repository can include, for example, rotating a carousel-type repository to align a desired end effector lumen with the deployment lumen. The desired end effector lumen can be determined in a number of manners, including by reading labels on the outside of the repository, observing the contents of each end effector lumen through a viewport formed therein, etc.

Methods of using the devices described herein can further include advancing a surgical end effector housed within the end effector lumen through the deployment lumen of the loading device and the working channel of the surgical trocar. Advancing the end effector can be accomplished using a variety of mechanisms, including slidable plunger-type advancers disposed in the end effector lumen, worm gear or other drive mechanisms coupled to the device, combinations thereof, etc.

Once an end effector is advanced through the deployment lumen, further steps can be performed, such as pivoting the end effector relative to the loading device, e.g., to better align with a percutaneous surgical instrument, and selectively releasing the end effector from the loading device, e.g., after the end effector has been coupled to a distal end of the percutaneous surgical instrument.

Any of the components and devices known in the art and/or described herein can be provided as part of a kit including any of a loading device, a trocar, and one or more surgical end effectors, as described herein, as well as other components with which such components are typically used, e.g., an obturator. The loading device can be configured to be removably coupled to the trocar using one or more complementary mating features or elements present on the trocar and the loading device. The trocar can be any particular model or configuration of trocar known in the art. Further, the end effectors provided in the kit can perform different functions, including but not limited to the functions described herein, and/or can be included together in a single kit to perform a particular function, such as a kit specifically tailored for stretching and stapling tissue. Further, one or more other ports or surgical instruments, including cameras and other viewing instruments, can be provided to assist in performing a given procedure.

The devices disclosed herein can be formed from a variety of materials and can have a variety of different sizes and shapes. For example, loading devices and trocars can be formed from various polymers and/or metals. Furthermore, particular components can be formed from a different material than other components. By way of further example, a loading device housing can be formed from a polymer material, (e.g., polycarbonate), while an end effector retainer (e.g., the pivoting end effector retainer 1206) can be formed from a metal, such as surgical grade stainless steel (e.g., 17-4), other 300 and 400 series stainless steels, titanium, and aluminum, perhaps to take advantage of greater rigidity. Of course, these are just non-limiting examples of possible material combinations. Device sizes can also vary greatly, depending on the intended use and surgical site anatomy. As mentioned above, the devices described herein can commonly be used in connection with trocar diameters on the order of 5 mm, though any particular size could be constructed. Further, a variety of lengths could be employed at any particular diameter to accommodate various end effector sizes, surgical site locations, etc.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical end effector loading device, comprising:
   at least one mating element configured to interface with at least one complementary mating element of a surgical trocar to restrict movement of the loading device relative to the trocar;
   a deployment lumen formed in a distal end of the loading device and positioned to align with a working channel of the surgical trocar when the at least one mating element is interfaced with the at least one complementary mating element of the trocar;
   an end effector repository having a plurality of end effector lumens formed therein that are each configured to receive a surgical end effector; and
   a plurality of advancers that are each slidably disposed within a respective one of the plurality of end effector lumens;
   wherein the end effector repository is configured to selectively align any of the plurality of end effector lumens and its respective advancer disposed therein with the deployment lumen such that axial translation of the respective advancer causes a surgical end effector to advance from its respective end effector lumen through the deployment lumen; and
   wherein the deployment lumen includes an end effector retainer disposed therein that is configured to engage to the surgical end effector and to selectively release the surgical end effector to allow the surgical end effector to be decoupled from the loading device and coupled to a separate surgical instrument.

2. The device of claim 1, wherein the end effector repository is a rotatable carousel.

3. The device of claim 2, wherein the end effector repository has three or more end effector lumens.

4. The device of claim 1, wherein the end effector repository includes a plurality of viewing ports positioned to permit visualization of the contents of each end effector lumen.

5. The device of claim 1, wherein at least one advancer of the plurality of advancers is coupled to an actuator that extends beyond an outer diameter of the end effector lumen.

6. The device of claim 1, wherein the plurality of advancers include a worm drive mechanism to effect movement of an end effector along a longitudinal axis of the device.

7. The device of claim 1, wherein the end effector retainer pivots relative to the device in order to pivot the surgical end effector relative to the device after the surgical end effector is advanced through the deployment lumen.

8. The device of claim 1, wherein the at least one mating element includes opposed actuating surfaces that are configured to be selectively depressed to decouple the device from the trocar.

9. A surgical instrument kit, comprising:
   a loading device comprising,
      at least one mating element,
      a deployment lumen formed in a distal end thereof, the deployment lumen having an end effector retainer disposed therein, and
      an end effector repository having a plurality of end effector lumens formed therein and a plurality of advancers that are each slidably disposed within a respective one of the plurality of end effector lumens, the end effector repository being configured to selectively align any of the plurality of end effector lumens and its respective advancer disposed therein with the deployment lumen;
   a trocar having a proximal end, a distal end, at least one mating element, and a working channel extending therethrough from the proximal end to the distal end; and
   a plurality of surgical end effectors;
   wherein the plurality of surgical end effectors are received within a respective one of the plurality of end effector lumens, the at least one mating element of the loading device interfaces with the at least one mating element of the trocar, and the deployment lumen of the loading device aligns with the working channel of the trocar; and
   wherein the end effector retainer is configured to allow each surgical end effector to be coupled to a separate surgical instrument and decoupled from the loading device.

10. The kit of claim 9, wherein the end effector repository is a rotatable carousel.

11. The kit of claim 9, wherein the end effector repository includes a plurality of viewing ports positioned to permit visualization of the contents of each end effector lumen.

12. The kit of claim 9, wherein at least one advancer of the plurality of advancers is coupled to an actuator that extends beyond an outer diameter of the end effector lumen.

13. The kit of claim 9, wherein the end effector retainer pivots relative to the loading device in order to pivot a surgical end effector coupled thereto relative to the loading device after the surgical end effector is advanced through the deployment lumen.

14. The kit of claim 9, wherein the at least one mating element of the loading device includes opposed actuating surfaces that are configured to be selectively depressed to decouple the loading device from the trocar.

15. A surgical method, comprising:
    coupling a loading device with a surgical trocar such that a deployment lumen formed in the loading device coaxially aligns with a working channel of the surgical trocar and complementary mating features on the loading device and the surgical trocar restrict relative motion therebetween;
    actuating an end effector repository of the loading device to align one of a plurality of end effector lumens formed therein with the deployment lumen of the loading device;
    translating a first advancer of a plurality of advancers to advance a surgical end effector housed within the aligned end effector lumen through the deployment lumen of the loading device and the working channel of the surgical trocar, wherein each advancer is slidably disposed within a respective one of the plurality of end effector lumens such that actuation of the end effector repository also aligns the first advancer with the deployment lumen; and
    coupling the advanced surgical end effector to a separate surgical instrument to allow the advanced surgical end effector to be removed from the loading device.

16. The method of claim 15, further comprising rotating a worm drive mechanism of the plurality of advancers to advance the surgical end effector through the deployment lumen.

17. The method of claim 15, further comprising pivoting the surgical end effector relative to the loading device after the surgical end effector has been advanced through the working channel of the surgical trocar.

18. The method of claim 15, wherein the mating feature of the loading device includes opposed actuating surfaces, and the method further comprises depressing the opposed actuating surfaces to decouple the loading device from the trocar.

* * * * *